United States Patent
Argyros et al.

(10) Patent No.: US 10,047,380 B2
(45) Date of Patent: *Aug. 14, 2018

(54) **GENETICALLY MODIFIED STRAIN OF *S. CEREVISIAE* ENGINEERED TO FERMENT XYLOSE AND ARABINOSE**

(71) Applicant: LALLEMAND HUNGARY LIQUIDITY MANAGEMENT LLC, Budapest (HU)

(72) Inventors: D. Aaron Argyros, Etna, NH (US); Nicky Caiazza, Rancho Santa Fe, CA (US); Trisha F. Barrett, Bradford, VT (US); Anne K. Warner, Lebanon, NH (US)

(73) Assignee: Lallemand Hungary Liquidity Management LLC, Budapest (HU)

( * ) Notice: Subject to any disclaimer, the term of this patent is extended or adjusted under 35 U.S.C. 154(b) by 0 days.

This patent is subject to a terminal disclaimer.

(21) Appl. No.: 15/454,275

(22) Filed: Mar. 9, 2017

(65) Prior Publication Data

US 2017/0191088 A1    Jul. 6, 2017

Related U.S. Application Data

(63) Continuation of application No. 14/356,510, filed as application No. PCT/US2012/064457 on Nov. 9, 2012, now Pat. No. 9,598,689.

(60) Provisional application No. 61/557,971, filed on Nov. 10, 2011.

(51) Int. Cl.
    *C12P 7/10*    (2006.01)
    *C12N 15/52*   (2006.01)
    *C12N 1/16*    (2006.01)

(52) U.S. Cl.
    CPC ........... *C12P 7/10* (2013.01); *C12N 1/16* (2013.01); *C12N 15/52* (2013.01); *C12P 2203/00* (2013.01); *Y02E 50/16* (2013.01)

(58) Field of Classification Search
    None
    See application file for complete search history.

(56) References Cited

U.S. PATENT DOCUMENTS

| | | | |
|---|---|---|---|
| 9,096,675 B2 | 8/2015 | Klaassen et al. | |
| 9,102,955 B2 | 8/2015 | McBride et al. | |
| 9,181,563 B2 | 11/2015 | Jessen et al. | |
| 9,598,689 B2 | 3/2017 | Argyros et al. | |
| 2007/0118916 A1 | 5/2007 | Puzio et al. | |
| 2010/0086965 A1 | 4/2010 | Van Maris et al. | |
| 2010/0143936 A1* | 6/2010 | Boles | C07K 14/39 435/7.1 |
| 2010/0304454 A1 | 12/2010 | De Bont | |
| 2012/0129229 A1 | 5/2012 | McBride et al. | |
| 2012/0129241 A1 | 5/2012 | Zhang et al. | |
| 2013/0040297 A1 | 2/2013 | Klaassen et al. | |
| 2014/0141473 A1 | 5/2014 | Klaassen et al. | |
| 2014/0295516 A1 | 10/2014 | Argyros et al. | |
| 2016/0002676 A1 | 1/2016 | Jessen et al. | |

FOREIGN PATENT DOCUMENTS

| | | |
|---|---|---|
| WO | 2008/041840 A1 | 4/2008 |
| WO | 2009/008756 A2 | 1/2009 |
| WO | 2010/060056 A2 | 5/2010 |
| WO | 2011/153516 A2 | 12/2011 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Accession P49374. Feb. 1, 1996.*
Accession D7IAX0. Aug. 10, 2010.*
Accession Q8AAW1. Jun. 1, 2003.*
Accession Q9P8C9. Oct. 1, 2000.*
Hong et al. J Biotechnol. Aug. 20, 2010;149(1-2):52-9. Epub Jun. 25, 2010.*
Accession Q8A9M2. Jun. 1, 2003.*
Zheng et al. Bioresour Technol. Feb. 2011;102(3):3020-7. Epub Oct. 8, 2010.*
Accession C6IEK6. Sep. 1, 2009.*
Becker, J., et al., "A modified *Saccharomyces cerevisiae* strain that consumes L-arabinose and produces ethanol," Appl. Environ. Microbiol. 2003, v. 69, pp. 4144-4150.
Chinese Office Action for Application No. 201280062514.9, dated Jul. 17, 2015 (15 pages).
International Search Report and Written Opinion for Application No. PCT/US2012/064457, dated Mar. 15, 2013 (11 pages).
Ladisch, M.R., et al., "Process considerations in the enzymatic hydrolysis of biomass," Enz. Microb. Technol.,1983, 5: 82-100.
van Walsum et al., "Allocation of ATP to synthesis of cells and hydrolytic enzymes in cellulolytic fermentative microorganisms: Bioenergetics, kinetics, and bioprocessing," Biotech. Bioeng., 58:316-320, (1998).

* cited by examiner

Primary Examiner — Christian Fronda
(74) Attorney, Agent, or Firm — Nutter McClennen & Fish LLP

(57) ABSTRACT

The present invention provides a microorganism capable of fermenting arabinose to a desired product such as ethanol. In some embodiments, the organism is also capable of fermenting xylose. In some embodiments, the organism is capable of fermenting arabinose and xylose, and expresses one or more cellulases.

25 Claims, 13 Drawing Sheets

SEQUENCE LISTING

```
<160> NUMBER OF SEQ ID NOS: 26

<210> SEQ ID NO 1
<211> LENGTH: 1530
<212> TYPE: DNA
<213> ORGANISM: Bacteroides thetaiotaomicron

<400> SEQUENCE: 1
atgaataacg tatttgatca gtatgaagta tggttcgtaa caggagcaca gctcttgtac      60
ggaggtgatg cagtaatcgc agtagacgca cactctaacg aaatggttaa cggtctgaat     120
gaatcgggca aacttcctgt taaagtagta tacaaaggaa cggccaactc ttctaaagag     180
gtggaagctg tattcaaagc agccaacaac gatgacaaat gtgtaggcgt catcacttgg     240
atgcatactt tctctcctgc taaaatgtgg attcatggtc tgcaacaatt aaagaaacca     300
ttgctgcacc tgcatactca attcaacaag gaaattcctt gggatacaat ggatatggac     360
tttatgaatc tgaaccagtc agctcacggc gaccgcgagt tcggacatat ctgtacccgt     420
atgcgcatcc gtcgcaaagt agtggtaggc tactggaaag aagaagaaac attgcataag     480
attgctgtct ggatgcgtgt ttgcgcaggt tgggcagact ctcaggatat gctgatcatc     540
cgtttcggcg atcagatgaa taatgtagcc gtaaccgatg gtgacaaggt agaagcagaa     600
caacgcatgg gctatcatgt agattattgc ccggcaagcg agctgatgga atatcacaaa     660
gatatcaaaa atgctgatgt agatgctttg gtagctactt acttcaatga ctacgatcat     720
gacgcttctc tggaagacaa atcaaccgaa gcttatcaga aagtatggaa tgctgccaaa     780
gccgagcttg ctctccgtgc tatcctcaaa gcgaaaggcg ccaaaggatt cactaccaac     840
tttgacgatc tgggtcagac tgacggtagc tatttcgatc agattccggg actggcttct     900
caacgcctga tggcagaagg ctacggattc ggtgctgaag gtgactggaa atcggctgct     960
ctttatcgta ctgtatgggt aatgaatcaa ggacttccga aaggctgttc attcctcgaa    1020
gactatacac tgaactttga tggtgccaac agttctatcc tacagtcaca tatgttggag    1080
atctgtccgc ttatcgcagc taacaagcct cgtctggaag tacacttcct cggcataggt    1140
atccgtaaga gccagactgc ccgtcttgtg ttcacttcaa agacaggaac aggctgcacc    1200
gcaactgtag tggatatggg taaccgtttc cgtctgatcg taaacgatgt agaatgtatc    1260
gaaccgaaac cacttccgaa attgccggtt gcttccgcac tctggattcc gatgcctaac    1320
ctcgaagtag gcgcaggcgc atggattctg gccggtggaa ctcaccactc ttgcttctca    1380
tacgacttga cagcagaata ctgggaagat tatgcagaaa tcgcaggcat cgaaatggta    1440
```

```
catatcaata aagatacgac tatcagctgc ttcaagaaag aactgcgcat gaatgaagta   1500
tattatatgc tgaacaaagc gctttgctaa                                   1530

<210> SEQ ID NO 2
<211> LENGTH: 1596
<212> TYPE: DNA
<213> ORGANISM: Bacteroides thetaiotaomicron

<400> SEQUENCE: 2
atgaaattag atgcaaaatc aaccatcgag acaggtaaag ctatccttgg catagaactc     60
ggttctacac gaataaaagc tgttctgatt gaccaggaaa acaaacctat cgctcaaggc    120
agccacacat gggaaaatca actggtcaac ggactttgga cttacagcat tgatgccatc    180
tggtccggac tgcaagattg ctacgccgac ctccgctcca acgtgaagaa attatacgac    240
acagagatcg aaacactggc agccatcggt gtcagcgcca tgatgcatgg ttacatgcct    300
ttcaatgaaa aagaagaaat cctcgtgcct tccgcactt ggagaaatac caatacaggc     360
cgtgctgcgg cagaattatc cgaattattt gtctataaca tcccttttgag atggagcatt    420 tctcatttgt accaggctat tctggacaac gaagcgcacg tcaaagacat caagttcctg    480
acaactcttg caggttatgt acattggcag ataacaggcg aaaaggtgtt gggcattggt    540
gacgcatcgg gtatgctccc catagatccg actaccaaca actattccgc cgaaatggtg    600
gccaaattca acaatctgat tgcttcgaaa gaatacagtt ggaaactgga agacattctg    660
cccaaagtat tgtcggctgg tgaaaatgcc ggtgtcctca caccggaagg ctgtaaaaaa    720
ctcgatgcat ccggtcatct gaaggcagga ataccggtct gcccaccgga aggagacgca    780
ggcaccggca tggtagcaac caacgccgtc aagcaacgca ccggcaacgt atcggcaggt    840
acttcttctt tctctatgat cgtattggaa aaagaattgt cgaagccata cgaaatgatc    900
gacatggtca ccactcccga cggaagcctc gtagccatgg tacattgcaa caactgtact    960
tcggatctta acgcatgggt caacctgttc aaagaatacc aggaacttct gggtatacct   1020
gtagatatgg atgaactcta tgcaaaactt tataacattg cccttaccgg tgataccgat   1080
tgcggtggtc tcctctccta caactacatt tcaggcgaac ctgttacggg acttgccgag   1140
ggaagacctt tgttcgtacg ttcggccaat gacaagttca accttgcaaa ctttatgcgg   1200
gctcatttgt acgcctcagt cggagttctc aagattggca cgacatcctt gttcaacgaa   1260
gaaaagatca agtcgacag aatcacaggt cacggaggat tgttcagaac caaaggagtc   1320
ggtcaaagag tacttgcagc agccatcaac tcgcccatat ctgttatgga acagccggt   1380 gaaggcggtg catggggaat tgccctgctg ggttcttacc tggtaaacaa taaaaagggt   1440
caatctcttg ccgatttcct ggatgaaagt gtatttgtca gcgatgctgg tgtcgaggta   1500
tcacccacac ccgaagatgt agccggcttc aacacataca tcgaaagcta caaggcaggt   1560
ttgcctatag aagaagcagc cgtcaaattc aaataa                             1596

<210> SEQ ID NO 3
<211> LENGTH: 684
<212> TYPE: DNA
<213> ORGANISM: Bacteroides thetaiotaomicron

<400> SEQUENCE: 3
atgctggaag aactgaaaga aaagtatttt catgccaatc tcgaattggt aaagcatgga     60
ttagtcatct ttacatgggg aaatgtttct gccatcgacc gtgaaacgga actggtagtc    120
```

| | |
|---|---|
| atcaaaccca gtggagtcag ttatgatgat atgaaagcgg aagatatggt agtagtggac | 180 |
| ctggatggca aagtcgtcga aggacggctg aagccatcct cagatactcc tactcacgtg | 240 |
| gtactctaca aagcattccc cgaaatcggc ggagtggtgc atacccactc tacttatgct | 300 |
| accgcatggg cgcaggccgg ttgtgatatt cccaatatcg ggacaactca cgctgactat | 360 |
| ttccatgatg caatcccctg cacagcggat atgacggaag ctgaagtaaa aggtgcctat | 420 |
| gaactggaaa ccgaaacgt gatcgtaaaa cgtttcgaag gcctgaaccc tgtacataca | 480 |
| ccgggagtat tggtcaagaa tcatggtcct ttctcttggg aaaagacgc acacgatgcc | 540 |
| gtacacaatg cagtagtgat ggaacaagtt gccaaaatgg caagcattgc ttatgccgtg | 600 |
| aatcccaatt taacaatgaa cccgctgctg gtagagaaac acttcagccg caagcatggt | 660 |
| ccgaacgctt actacggaca ataa | 684 |

<210> SEQ ID NO 4
<211> LENGTH: 1656
<212> TYPE: DNA
<213> ORGANISM: Kluyveromyces lactis

<400> SEQUENCE: 4

| | |
|---|---|
| atgtcattga aaaattggct tttgctacgt gatatccaat acgagggaac gttttataaa | 60 |
| aagttccccc atgtctacaa catttacgtc atcggttttca tagcatgtat ctccggtctt | 120 |
| atgttcggtt tgatatcgc atcgatgtct tctatgattg gtaccgatgt ttacaaggac | 180 |
| tatttcagta atcctgactc tttgacttac ggtggtatta ctgcttctat ggcaggtggt | 240 |
| tcattcttgg gttctttgat ctctccaaac ttttctgatg cttttggtag aaaagtctct | 300 |
| ttgcatatat gtgctgctct atggattatt ggtgccattc tacaatgtgc tgctcaagac | 360 |
| caagccatgt tgatcgtggg tcgtgttatt tctggtatgg gtattggttt cggttcctct | 420 |
| gctgcccctg tgtactgttc tgaaatctcc ccaccaaaga ttagaggtac catttctggt | 480 |
| cttttccaat tctctgttac cgttggtatc atggtcctat tctacatcgg ttacggttgt | 540 |
| cacttcattg atggcgctgc tgcctttaga atcacttggg ggttgcaaat ggttccaggt | 600 |
| ttgatcttaa tggtcggtgt attctttatc ccggaatccc cacgttggtt ggctaaccat | 660 |
| gatcgttggg aagaaacttc tctcatcgtt gctaacatcg ttgctaacgg tgacgttaac | 720 |
| aacgaacaag ttcgtttcca attggaagaa attaaggaac aagtcatcat cgattctgct | 780 |
| gccaagaact tcggttacaa agatttattc agaaagaaga ctttaccaaa acaatcgtt | 840 |
| ggtgttttctg ctcaaatgtg gcaacaacta tgtggtatga atgttatgat gtactacatt | 900 |
| gtctacattt tcaacatggc tggttacact ggtaacacta acttggttgc ctcgtccatt | 960 |
| caatatgtgc taaatgttgt tatgactatc ccagcattgt tcttgattga taaatttggt | 1020 |
| agaagacctg tgttgatcat tggtggtatc ttcatgttca cttggttgtt ctctgtcgct | 1080 |
| ggtatcttgg ctacttactc cgttccagcc ccaggcggtg tcaacggtga tgatactgtt | 1140 |
| actattcaaa ttccaagtga aaacacttcc gctgctaacg tgtcattgc atcctcatac | 1200 |
| ttgttcgtct gttctcttcgc tccaacttgg ggtattggta tctggattta ctgttctgaa | 1260 |
| attttcaaca acatggaaag agctaagggt tctgcccttt ctgcagcaac taactgggcc | 1320 |
| ttcaactttg ccttggctat gttcgttcca tctgccttca aaacatttc ctggaagacc | 1380 |
| tacatcatct tggtgtgtctt ctctgttgct ttgactattc aaactttctt catgttccca | 1440 |
| gaaactaagg ggaaaacttt agaagaaatc gaccaaatgt gggttgataa tattccagca | 1500 |
| tggaggactg ctaattacat tccacaacta cctatcgtta aagatgaaga aggtaacaag | 1560 |

```
ttgggcttgt tgggtaaccc acaacatttg gaagatgttc attctaatga aaagggtcta   1620
cttgaccgtt ccgactcagc aagcaactcc aattaa                              1656

<210> SEQ ID NO 5
<211> LENGTH: 1686
<212> TYPE: DNA
<213> ORGANISM: Kluyveromyces thermotolerans

<400> SEQUENCE: 5
atgtcgtcaa agtcgtataa ggacacgctg ctgctgcgca acgtcaagta ccgcggcgcg     60
ctgtacgacc ggttccctaa ggtgtacaac gtgtacgtgg tggcgatggt gtcgtgcatc   120
tcggggctga tgttcgggtt cgacatcagc tccatgtcat cgatgatcgg gactgacaaa   180
tacaaggagt acttcagcaa tccagactcg acgacgcagg gtggaatcac ggcgtcgatg   240
tccggcgggt cgctgctcgg gtcgctgata tcgccaaact tcacggacgc gttcgggcgg   300
cgtgtgtcgc tgcacatctg tgcggcgctg tggatcgcgg gcgcggtgct gcagtgcgcg   360
tcgcagaacc agggaatgct gattgtcggg cgtgtgatca gcggcatggg cgtcgggttc   420
ggctcgtcgg ccgcgcccgt gtactgctct gaggttgcgc cccccaacat ccgcggcacc   480
gtgtgcggcc tgttccagtt cagcgtcacc ctgggcatca tgatcatgtt ctacatcggc   540
tacggctgcc acttcatcga cggaacggcc tcgttccgca tcacctgggg gctgcagatg   600
gtgcccggct cgcgctgat gctgttcacc ttcttcctac ccgagtcgcc ccggtggctt   660
gccaaccacg accgctggga ggaggccagc gaggtggtcg cccgcatagg cgccaagggc   720
agcctcgaca acccacaggt gcgcctacag ctcgaggaga tccgcgagca ggtcatcatc   780
gaccagcagg ccgcgcactt tgggttccgc cagctgttcc gcaagaagac tattaacaaa   840
accattgtcg gcgtgtgcgc ccagatgtgg cagcagctgt gcggtatgaa cgtcatgatg   900
tactacatcg tgtacatctt ccagatggcc ggctactcgg gcaacacact gttggtgtcc   960
agttctattc agtacgtgct gaacgtggtg atgactatcc ccgccctgct ccttgtcgat  1020
aaaatcggca ggaggcccgt cctgatggtc ggcggcgtct tcatgtttat ctggctgttt  1080
gtcgtggcag gcttgttggc agactactcg gtccccgagc cagacgggtt tgagggtgac  1140
gacacagtga ggatcaggat ccctgacagt gaaaagtcgg ctgccaaggg tgtaatagct  1200
gcgtcctacc tgttcgtgtg ctccttcgca ccttcctggg gtgttggtat ttggatctac  1260
tgttccgaga ttttcaacaa cttcgaaaga gctagggat ccgctttctg tgcgtccgtc  1320
aactgggcct ttaacttcgc cctggcaatg tttgtgcctt ctgccttcaa gaacatcacc  1380
tggaagacat acattatctt tggcgtgttt tccatcgccc tgaccattca aaccttcttg  1440
atgttcccgg agacaaaggg caagacactg gaggaaattg accaaatgtg ggcagatcac  1500
attcctgcgt ggaagacagc ctcgtacgtg cctgacgttc ctgttgtaca ggacgaagag  1560
ggcaacaaat tggggctgat ggggagatct cagcacgttg aaaactcgtc aaatactcca  1620
gaagaaaagc ccatgtttga gcagcagagt agtgctgata acagtctcac gcgcgccgaa  1680
tcgtaa                                                              1686

<210> SEQ ID NO 6
<211> LENGTH: 509
<212> TYPE: PRT
<213> ORGANISM: Bacteroides thetaiotaomicron

<400> SEQUENCE: 6
```

```
Met Asn Asn Val Phe Asp Gln Tyr Glu Val Trp Phe Val Thr Gly Ala
1               5                   10                  15

Gln Leu Leu Tyr Gly Gly Asp Ala Val Ile Ala Val Asp Ala His Ser
            20                  25                  30

Asn Glu Met Val Asn Gly Leu Asn Glu Ser Gly Lys Leu Pro Val Lys
        35                  40                  45

Val Val Tyr Lys Gly Thr Ala Asn Ser Ser Lys Glu Val Glu Ala Val
    50                  55                  60

Phe Lys Ala Ala Asn Asp Asp Lys Cys Val Gly Val Ile Thr Trp
65                  70                  75                  80

Met His Thr Phe Ser Pro Ala Lys Met Trp Ile His Gly Leu Gln Gln
                85                  90                  95

Leu Lys Lys Pro Leu Leu His Leu His Thr Gln Phe Asn Lys Glu Ile
                100                 105                 110

Pro Trp Asp Thr Met Asp Met Asp Phe Met Asn Leu Asn Gln Ser Ala
            115                 120                 125

His Gly Asp Arg Glu Phe Gly His Ile Cys Thr Arg Met Arg Ile Arg
        130                 135                 140

Arg Lys Val Val Val Gly Tyr Trp Lys Glu Glu Thr Leu His Lys
145                 150                 155                 160

Ile Ala Val Trp Met Arg Val Cys Ala Gly Trp Ala Asp Ser Gln Asp
                165                 170                 175

Met Leu Ile Ile Arg Phe Gly Asp Gln Met Asn Asn Val Ala Val Thr
            180                 185                 190

Asp Gly Asp Lys Val Glu Ala Glu Gln Arg Met Gly Tyr His Val Asp
        195                 200                 205

Tyr Cys Pro Ala Ser Glu Leu Met Glu Tyr His Lys Asp Ile Lys Asn
    210                 215                 220

Ala Asp Val Asp Ala Leu Val Ala Thr Tyr Phe Asn Asp Tyr Asp His
225                 230                 235                 240

Asp Ala Ser Leu Glu Asp Lys Ser Thr Glu Ala Tyr Gln Lys Val Trp
                245                 250                 255

Asn Ala Ala Lys Ala Glu Leu Ala Leu Arg Ala Ile Leu Lys Ala Lys
            260                 265                 270

Gly Ala Lys Gly Phe Thr Thr Asn Phe Asp Asp Leu Gly Gln Thr Asp
        275                 280                 285

Gly Ser Tyr Phe Asp Gln Ile Pro Gly Leu Ala Ser Gln Arg Leu Met
    290                 295                 300

Ala Glu Gly Tyr Gly Phe Gly Ala Glu Gly Asp Trp Lys Ser Ala Ala
305                 310                 315                 320

Leu Tyr Arg Thr Val Trp Val Met Asn Gln Gly Leu Pro Lys Gly Cys
                325                 330                 335

Ser Phe Leu Glu Asp Tyr Thr Leu Asn Phe Asp Gly Ala Asn Ser Ser
            340                 345                 350

Ile Leu Gln Ser His Met Leu Glu Ile Cys Pro Leu Ile Ala Ala Asn
        355                 360                 365

Lys Pro Arg Leu Glu Val His Phe Leu Gly Ile Gly Ile Arg Lys Ser
    370                 375                 380

Gln Thr Ala Arg Leu Val Phe Thr Ser Lys Thr Gly Thr Gly Cys Thr
385                 390                 395                 400

Ala Thr Val Val Asp Met Gly Asn Arg Phe Arg Leu Ile Val Asn Asp
                405                 410                 415

Val Glu Cys Ile Glu Pro Lys Pro Leu Pro Lys Leu Pro Val Ala Ser
```

```
            420                 425                 430
Ala Leu Trp Ile Pro Met Pro Asn Leu Glu Val Gly Ala Gly Ala Trp
            435                 440                 445

Ile Leu Ala Gly Gly Thr His His Ser Cys Phe Ser Tyr Asp Leu Thr
            450                 455                 460

Ala Glu Tyr Trp Glu Asp Tyr Ala Glu Ile Ala Gly Ile Glu Met Val
465                 470                 475                 480

His Ile Asn Lys Asp Thr Thr Ile Ser Cys Phe Lys Lys Glu Leu Arg
            485                 490                 495

Met Asn Glu Val Tyr Tyr Met Leu Asn Lys Ala Leu Cys
            500                 505

<210> SEQ ID NO 7
<211> LENGTH: 531
<212> TYPE: PRT
<213> ORGANISM: Bacteroides thetaiotaomicron

<400> SEQUENCE: 7

Met Lys Leu Asp Ala Lys Ser Thr Ile Glu Thr Gly Lys Ala Ile Leu
1               5                   10                  15

Gly Ile Glu Leu Gly Ser Thr Arg Ile Lys Ala Val Leu Ile Asp Gln
            20                  25                  30

Glu Asn Lys Pro Ile Ala Gln Gly Ser His Thr Trp Glu Asn Gln Leu
        35                  40                  45

Val Asn Gly Leu Trp Thr Tyr Ser Ile Asp Ala Ile Trp Ser Gly Leu
    50                  55                  60

Gln Asp Cys Tyr Ala Asp Leu Arg Ser Asn Val Lys Lys Leu Tyr Asp
65                  70                  75                  80

Thr Glu Ile Glu Thr Leu Ala Ala Ile Gly Val Ser Ala Met Met His
            85                  90                  95

Gly Tyr Met Pro Phe Asn Glu Lys Glu Ile Leu Val Pro Phe Arg
            100                 105                 110

Thr Trp Arg Asn Thr Asn Thr Gly Arg Ala Ala Ala Glu Leu Ser Glu
            115                 120                 125

Leu Phe Val Tyr Asn Ile Pro Leu Arg Trp Ser Ile Ser His Leu Tyr
    130                 135                 140

Gln Ala Ile Leu Asp Asn Glu Ala His Val Lys Asp Ile Lys Phe Leu
145                 150                 155                 160

Thr Thr Leu Ala Gly Tyr Val His Trp Gln Ile Thr Gly Glu Lys Val
            165                 170                 175

Leu Gly Ile Gly Asp Ala Ser Gly Met Leu Pro Ile Asp Pro Thr Thr
            180                 185                 190

Asn Asn Tyr Ser Ala Glu Met Val Ala Lys Phe Asn Asn Leu Ile Ala
        195                 200                 205

Ser Lys Glu Tyr Ser Trp Lys Leu Glu Asp Ile Leu Pro Lys Val Leu
    210                 215                 220

Ser Ala Gly Glu Asn Ala Gly Val Leu Thr Pro Glu Gly Cys Lys Lys
225                 230                 235                 240

Leu Asp Ala Ser Gly His Leu Lys Ala Gly Ile Pro Val Cys Pro Pro
            245                 250                 255

Glu Gly Asp Ala Gly Thr Gly Met Val Ala Thr Asn Ala Val Lys Gln
            260                 265                 270

Arg Thr Gly Asn Val Ser Ala Gly Thr Ser Ser Phe Ser Met Ile Val
        275                 280                 285
```

```
Leu Glu Lys Glu Leu Ser Lys Pro Tyr Glu Met Ile Asp Met Val Thr
    290                 295                 300
Thr Pro Asp Gly Ser Leu Val Ala Met Val His Cys Asn Asn Cys Thr
305                 310                 315                 320
Ser Asp Leu Asn Ala Trp Val Asn Leu Phe Lys Glu Tyr Gln Glu Leu
                325                 330                 335
Leu Gly Ile Pro Val Asp Met Asp Glu Leu Tyr Gly Lys Leu Tyr Asn
            340                 345                 350
Ile Ala Leu Thr Gly Asp Thr Asp Cys Gly Gly Leu Leu Ser Tyr Asn
        355                 360                 365
Tyr Ile Ser Gly Glu Pro Val Thr Gly Leu Ala Glu Gly Arg Pro Leu
    370                 375                 380
Phe Val Arg Ser Ala Asn Asp Lys Phe Asn Leu Ala Asn Phe Met Arg
385                 390                 395                 400
Ala His Leu Tyr Ala Ser Val Gly Val Leu Lys Ile Gly Asn Asp Ile
                405                 410                 415
Leu Phe Asn Glu Glu Lys Ile Lys Val Asp Arg Ile Thr Gly His Gly
            420                 425                 430
Gly Leu Phe Arg Thr Lys Gly Val Gly Gln Arg Val Leu Ala Ala Ala
        435                 440                 445
Ile Asn Ser Pro Ile Ser Val Met Glu Thr Ala Gly Glu Gly Gly Ala
    450                 455                 460
Trp Gly Ile Ala Leu Leu Gly Ser Tyr Leu Val Asn Asn Lys Lys Gly
465                 470                 475                 480
Gln Ser Leu Ala Asp Phe Leu Asp Glu Ser Val Phe Val Ser Asp Ala
                485                 490                 495
Gly Val Glu Val Ser Pro Thr Pro Glu Asp Val Ala Gly Phe Asn Thr
            500                 505                 510
Tyr Ile Glu Ser Tyr Lys Ala Gly Leu Pro Ile Glu Glu Ala Ala Val
        515                 520                 525
Lys Phe Lys
    530

<210> SEQ ID NO 8
<211> LENGTH: 227
<212> TYPE: PRT
<213> ORGANISM: Bacteroides thetaiotaomicron

<400> SEQUENCE: 8

Met Leu Glu Glu Leu Lys Glu Lys Val Phe His Ala Asn Leu Glu Leu
1               5                   10                  15
Val Lys His Gly Leu Val Ile Phe Thr Trp Gly Asn Val Ser Ala Ile
            20                  25                  30
Asp Arg Glu Thr Glu Leu Val Val Ile Lys Pro Ser Gly Val Ser Tyr
        35                  40                  45
Asp Asp Met Lys Ala Glu Asp Met Val Val Asp Leu Asp Gly Lys
    50                  55                  60
Val Val Glu Gly Arg Leu Lys Pro Ser Ser Asp Thr Pro Thr His Val
65                  70                  75                  80
Val Leu Tyr Lys Ala Phe Pro Glu Ile Gly Gly Val Val His Thr His
                85                  90                  95
Ser Thr Tyr Ala Thr Ala Trp Ala Gln Ala Gly Cys Asp Ile Pro Asn
            100                 105                 110
Ile Gly Thr Thr His Ala Asp Tyr Phe His Asp Ala Ile Pro Cys Thr
        115                 120                 125
```

```
Ala Asp Met Thr Glu Ala Glu Val Lys Gly Ala Tyr Glu Leu Glu Thr
        130                 135                 140

Gly Asn Val Ile Val Lys Arg Phe Glu Gly Leu Asn Pro Val His Thr
145                 150                 155                 160

Pro Gly Val Leu Val Lys Asn His Gly Pro Phe Ser Trp Gly Lys Asp
                165                 170                 175

Ala His Asp Ala Val His Asn Ala Val Val Met Glu Gln Val Ala Lys
            180                 185                 190

Met Ala Ser Ile Ala Tyr Ala Val Asn Pro Asn Leu Thr Met Asn Pro
        195                 200                 205

Leu Leu Val Glu Lys His Phe Ser Arg Lys His Gly Pro Asn Ala Tyr
210                 215                 220

Tyr Gly Gln
225

<210> SEQ ID NO 9
<211> LENGTH: 551
<212> TYPE: PRT
<213> ORGANISM: Kluyveromyces lactis

<400> SEQUENCE: 9

Met Ser Leu Lys Asn Trp Leu Leu Arg Asp Ile Gln Tyr Glu Gly
1               5                   10                  15

Thr Phe Tyr Lys Lys Phe Pro His Val Tyr Asn Ile Tyr Val Ile Gly
                20                  25                  30

Phe Ile Ala Cys Ile Ser Gly Leu Met Phe Gly Phe Asp Ile Ala Ser
            35                  40                  45

Met Ser Ser Met Ile Gly Thr Asp Val Tyr Lys Asp Tyr Phe Ser Asn
        50                  55                  60

Pro Asp Ser Leu Thr Tyr Gly Ile Thr Ala Ser Met Ala Gly Gly
65                  70                  75                  80

Ser Phe Leu Gly Ser Leu Ile Ser Pro Asn Phe Ser Asp Ala Phe Gly
                85                  90                  95

Arg Lys Val Ser Leu His Ile Cys Ala Ala Leu Trp Ile Ile Gly Ala
                100                 105                 110

Ile Leu Gln Cys Ala Ala Gln Asp Gln Ala Met Leu Ile Val Gly Arg
            115                 120                 125

Val Ile Ser Gly Met Gly Ile Gly Phe Gly Ser Ser Ala Ala Pro Val
        130                 135                 140

Tyr Cys Ser Glu Ile Ser Pro Pro Lys Ile Arg Gly Thr Ile Ser Gly
145                 150                 155                 160

Leu Phe Gln Phe Ser Val Thr Val Gly Ile Met Val Leu Phe Tyr Ile
                165                 170                 175

Gly Tyr Gly Cys His Phe Ile Asp Gly Ala Ala Ala Phe Arg Ile Thr
            180                 185                 190

Trp Gly Leu Gln Met Val Pro Gly Leu Ile Leu Met Val Gly Val Phe
        195                 200                 205

Phe Ile Pro Glu Ser Pro Arg Trp Leu Ala Asn His Asp Arg Trp Glu
210                 215                 220

Glu Thr Ser Leu Ile Val Ala Asn Ile Val Ala Asn Gly Asp Val Asn
225                 230                 235                 240

Asn Glu Gln Val Arg Phe Gln Leu Glu Glu Ile Lys Glu Gln Val Ile
                245                 250                 255

Ile Asp Ser Ala Ala Lys Asn Phe Gly Tyr Lys Asp Leu Phe Arg Lys
```

```
            260                 265                 270
Lys Thr Leu Pro Lys Thr Ile Val Gly Val Ser Ala Gln Met Trp Gln
            275                 280                 285

Gln Leu Cys Gly Met Asn Val Met Tyr Tyr Ile Val Tyr Ile Phe
        290                 295                 300

Asn Met Ala Gly Tyr Thr Gly Asn Thr Asn Leu Val Ala Ser Ser Ile
305                 310                 315                 320

Gln Tyr Val Leu Asn Val Val Met Thr Ile Pro Ala Leu Phe Leu Ile
                325                 330                 335

Asp Lys Phe Gly Arg Arg Pro Val Leu Ile Ile Gly Gly Ile Phe Met
            340                 345                 350

Phe Thr Trp Leu Phe Ser Val Ala Gly Ile Leu Ala Thr Tyr Ser Val
            355                 360                 365

Pro Ala Pro Gly Gly Val Asn Gly Asp Asp Thr Val Thr Ile Gln Ile
            370                 375                 380

Pro Ser Glu Asn Thr Ser Ala Ala Asn Gly Val Ile Ala Ser Ser Tyr
385                 390                 395                 400

Leu Phe Val Cys Phe Phe Ala Pro Thr Trp Gly Ile Gly Ile Trp Ile
                405                 410                 415

Tyr Cys Ser Glu Ile Phe Asn Asn Met Glu Arg Ala Lys Gly Ser Ala
                420                 425                 430

Leu Ser Ala Ala Thr Asn Trp Ala Phe Asn Phe Ala Leu Ala Met Phe
            435                 440                 445

Val Pro Ser Ala Phe Lys Asn Ile Ser Trp Lys Thr Tyr Ile Ile Phe
            450                 455                 460

Gly Val Phe Ser Val Ala Leu Thr Ile Gln Thr Phe Phe Met Phe Pro
465                 470                 475                 480

Glu Thr Lys Gly Lys Thr Leu Glu Glu Ile Asp Gln Met Trp Val Asp
                485                 490                 495

Asn Ile Pro Ala Trp Arg Thr Ala Asn Tyr Ile Pro Gln Leu Pro Ile
            500                 505                 510

Val Lys Asp Glu Glu Gly Asn Lys Leu Gly Leu Leu Gly Asn Pro Gln
            515                 520                 525

His Leu Glu Asp Val His Ser Asn Glu Lys Gly Leu Leu Asp Arg Ser
            530                 535                 540

Asp Ser Ala Ser Asn Ser Asn
545                 550

<210> SEQ ID NO 10
<211> LENGTH: 561
<212> TYPE: PRT
<213> ORGANISM: Kluyveromyces thermotolerans

<400> SEQUENCE: 10

Met Ser Ser Lys Ser Tyr Lys Asp Thr Leu Leu Leu Arg Asn Val Lys
1               5                   10                  15

Tyr Arg Gly Ala Leu Tyr Asp Arg Phe Pro Lys Val Tyr Asn Val Tyr
            20                  25                  30

Val Val Ala Met Val Ser Cys Ile Ser Gly Leu Met Phe Gly Phe Asp
        35                  40                  45

Ile Ser Ser Met Ser Ser Met Ile Gly Thr Asp Lys Tyr Lys Glu Tyr
    50                  55                  60

Phe Ser Asn Pro Asp Ser Thr Gln Gly Gly Ile Thr Ala Ser Met
65                  70                  75                  80
```

-continued

```
Ser Gly Gly Ser Leu Leu Gly Ser Leu Ile Ser Pro Asn Phe Thr Asp
             85                  90                  95

Ala Phe Gly Arg Arg Val Ser Leu His Ile Cys Ala Ala Leu Trp Ile
        100                 105                 110

Ala Gly Ala Val Leu Gln Cys Ala Ser Gln Asn Gln Gly Met Leu Ile
            115                 120                 125

Val Gly Arg Val Ile Ser Gly Met Gly Val Gly Phe Gly Ser Ser Ala
130                 135                 140

Ala Pro Val Tyr Cys Ser Glu Val Ala Pro Asn Ile Arg Gly Thr
145                 150                 155                 160

Val Cys Gly Leu Phe Gln Phe Ser Val Thr Leu Gly Ile Met Ile Met
                165                 170                 175

Phe Tyr Ile Gly Tyr Gly Cys His Phe Ile Asp Gly Thr Ala Ser Phe
            180                 185                 190

Arg Ile Thr Trp Gly Leu Gln Met Val Pro Gly Phe Ala Leu Met Leu
        195                 200                 205

Phe Thr Phe Phe Leu Pro Glu Ser Pro Arg Trp Leu Ala Asn His Asp
    210                 215                 220

Arg Trp Glu Glu Ala Ser Glu Val Val Ala Arg Ile Gly Ala Lys Gly
225                 230                 235                 240

Ser Leu Asp Asn Pro Gln Val Arg Leu Gln Leu Glu Glu Ile Arg Glu
                245                 250                 255

Gln Val Ile Ile Asp Gln Gln Ala Ala His Phe Gly Phe Arg Gln Leu
            260                 265                 270

Phe Arg Lys Lys Thr Ile Asn Lys Thr Ile Val Gly Val Cys Ala Gln
        275                 280                 285

Met Trp Gln Gln Leu Cys Gly Met Asn Val Met Met Tyr Tyr Ile Val
    290                 295                 300

Tyr Ile Phe Gln Met Ala Gly Tyr Ser Gly Asn Thr Leu Leu Val Ser
305                 310                 315                 320

Ser Ser Ile Gln Tyr Val Leu Asn Val Val Met Thr Ile Pro Ala Leu
                325                 330                 335

Leu Leu Val Asp Lys Ile Gly Arg Arg Pro Val Leu Met Val Gly Gly
            340                 345                 350

Val Phe Met Phe Ile Trp Leu Phe Val Val Ala Gly Leu Leu Ala Asp
        355                 360                 365

Tyr Ser Val Pro Glu Pro Asp Gly Phe Glu Gly Asp Asp Thr Val Arg
    370                 375                 380

Ile Arg Ile Pro Asp Ser Glu Lys Ser Ala Ala Lys Gly Val Ile Ala
385                 390                 395                 400

Ala Ser Tyr Leu Phe Val Cys Ser Phe Ala Pro Ser Trp Gly Val Gly
                405                 410                 415

Ile Trp Ile Tyr Cys Ser Glu Ile Phe Asn Asn Phe Glu Arg Ala Arg
            420                 425                 430

Gly Ser Ala Phe Cys Ala Ser Val Asn Trp Ala Phe Asn Phe Ala Leu
        435                 440                 445

Ala Met Phe Val Pro Ser Ala Phe Lys Asn Ile Thr Trp Lys Thr Tyr
    450                 455                 460

Ile Ile Phe Gly Val Phe Ser Ile Ala Leu Thr Ile Gln Thr Phe Leu
465                 470                 475                 480

Met Phe Pro Glu Thr Lys Gly Lys Thr Leu Glu Glu Ile Asp Gln Met
                485                 490                 495

Trp Ala Asp His Ile Pro Ala Trp Lys Thr Ala Ser Tyr Val Pro Asp
```

```
            500                 505                 510
Val Pro Val Val Gln Asp Glu Glu Gly Asn Lys Leu Gly Leu Met Gly
            515                 520                 525

Arg Ser Gln His Val Glu Asn Ser Ser Asn Thr Pro Glu Glu Lys Pro
        530                 535                 540

Met Phe Glu Gln Gln Ser Ser Ala Asp Asn Ser Leu Thr Arg Ala Glu
545                 550                 555                 560

Ser

<210> SEQ ID NO 11
<211> LENGTH: 571
<212> TYPE: PRT
<213> ORGANISM: Zygosaccharomyces rouxii

<400> SEQUENCE: 11

Met Lys Ile Asp Lys Lys Gln Ile Gly Cys Ala Leu Met Gly Lys Arg
1               5                   10                  15

Ile Asn Tyr Arg Val Thr Ile Tyr Asp Lys Phe Pro Lys Ile Tyr Asn
            20                  25                  30

Ile Phe Val Ile Gly Phe Thr Ser Cys Ile Ser Gly Leu Met Phe Gly
        35                  40                  45

Phe Asp Val Ser Ser Met Ser Ser Met Ile Gly Thr Asp Gly Tyr Lys
    50                  55                  60

Glu Tyr Phe Gly Thr Pro Gly Pro Thr Glu Gln Gly Gly Ile Thr Ala
65                  70                  75                  80

Cys Met Pro Ala Gly Ser Phe Val Ala Ser Leu Ile Ala Pro Tyr Phe
                85                  90                  95

Ser Asp Asn Phe Gly Arg Arg Val Ser Leu His Leu Cys Ala Ile Phe
            100                 105                 110

Trp Met Ile Gly Ala Val Leu Gln Cys Ala Ser Gln Asp Leu Ala Met
        115                 120                 125

Leu Cys Val Gly Arg Val Val Ser Gly Leu Gly Ile Gly Phe Gly Ser
    130                 135                 140

Ser Val Ala Pro Val Tyr Cys Ser Glu Ile Ala Pro Pro Lys Ile Arg
145                 150                 155                 160

Gly Ala Ile Gly Gly Leu Phe Gln Phe Ser Val Thr Leu Gly Ile Met
                165                 170                 175

Ile Leu Phe Phe Ile Gly Tyr Gly Ala His Phe Ile Asn Gly Ala Gly
            180                 185                 190

Ser Phe Arg Leu Thr Trp Gly Ile Glu Leu Val Pro Gly Ala Cys Leu
        195                 200                 205

Leu Ile Ala Val Phe Phe Leu Pro Glu Ser Pro Arg Trp Leu Ala Leu
    210                 215                 220

His Asp Tyr Trp Glu Glu Ala Glu Asp Ile Val Ile Arg Val Ala Ala
225                 230                 235                 240

Lys Gly Asn Arg Glu Asn Glu Gln Val Met Ile Gln Leu Glu Glu Ile
                245                 250                 255

Arg Glu Gln Val Glu Ile Asp Lys Glu Ala Glu Ala Phe Gln Leu Lys
            260                 265                 270

Asp Leu Phe Arg Pro Lys Thr Arg Val Lys Thr Met Val Gly Met Met
        275                 280                 285

Ala Gln Met Trp Gln Gln Met Cys Gly Met Asn Val Met Met Tyr Tyr
    290                 295                 300

Ile Val Tyr Ile Phe Thr Met Ala Gly Phe Lys Gly Gly Ala Val Leu
```

```
            305                 310                 315                 320
Val Ser Gly Ser Ile Gln Tyr Val Leu Asn Val Val Met Thr Ile Pro
                325                 330                 335

Ala Leu Phe Leu Met Asp Lys Cys Gly Arg Arg Pro Val Leu Leu Ile
                340                 345                 350

Gly Gly Leu Leu Met Cys Ala Trp Leu Phe Ala Val Gly Gly Leu Leu
                355                 360                 365

Ala Thr Tyr Ser Asp Pro Tyr Pro His Gly Phe Glu Gly Asp Glu Thr
                370                 375                 380

Val Arg Ile Ala Ile Pro Gln Ser Asn Lys Pro Ala Ala Asn Gly Val
385                 390                 395                 400

Ile Ala Cys Ser Tyr Leu Phe Val Cys Ser Tyr Ala Pro Thr Trp Gly
                405                 410                 415

Val Cys Ile Trp Ile Tyr Cys Ala Glu Ile Phe Asn Asn Thr Glu Arg
                420                 425                 430

Ala Lys Gly Ser Gly Leu Cys Thr Ala Val Asn Trp Ile Phe Asn Phe
                435                 440                 445

Ala Leu Ala Leu Phe Val Pro Ser Ala Phe Lys Asn Leu Thr Trp Lys
                450                 455                 460

Thr Tyr Ile Met Phe Gly Val Phe Cys Val Ala Leu Thr Ile Asn Thr
465                 470                 475                 480

Phe Leu Leu Phe Pro Glu Thr Lys Gly Lys Thr Leu Glu Glu Ile Asp
                485                 490                 495

Gln Met Trp Glu Ala His Ile Pro Ala Trp Lys Thr His Ser Trp Val
                500                 505                 510

Pro Thr Ile Pro Ser Ala Ser Lys Phe Asp Gln Glu Met His Lys Thr
                515                 520                 525

Asp Leu Glu His Val Glu Asp Thr Gly Asp Ser Asp Arg Ile Ser Pro
                530                 535                 540

Lys Asp Asp Ser Glu Lys Gly Ser Val Thr Gly Leu Glu Glu Val Ala
545                 550                 555                 560

Lys Ser Asn Pro Asn Ser Thr Ser Leu Ser Glu
                565                 570

<210> SEQ ID NO 12
<211> LENGTH: 556
<212> TYPE: PRT
<213> ORGANISM: Vanderwaltozyma polyspora

<400> SEQUENCE: 12

Met Gly Ser Phe Lys Asp Thr Ile Leu Met Lys Asn Ile Lys Tyr Glu
1               5                   10                  15

Gly Lys Leu Tyr Glu Arg Phe Pro Lys Ile Tyr Asn Ile Tyr Val Ile
                20                  25                  30

Gly Phe Val Ser Cys Ile Ser Gly Leu Met Phe Gly Phe Asp Ile Ser
                35                  40                  45

Ser Met Ser Ser Met Ile Gly Thr Asp Ala Tyr Lys Gln Tyr Phe Gly
                50                  55                  60

Ser Pro Asp Ala Thr Lys Gln Gly Gly Ile Thr Ser Ser Met Ala Ala
65                  70                  75                  80

Gly Ser Phe Val Gly Ser Leu Leu Ser Pro Leu Phe Ser Asp Val Phe
                85                  90                  95

Gly Arg Arg Val Ser Leu His Ile Cys Ser Thr Phe Trp Leu Ile Gly
                100                 105                 110
```

```
Ala Thr Leu Gln Cys Ala Ser Gln Asp Leu Ala Met Leu Val Val Gly
115                 120                 125

Arg Leu Val Ser Gly Ile Gly Ile Gly Phe Gly Ser Ala Val Ala Pro
    130                 135                 140

Val Tyr Cys Ser Glu Val Ala Pro Pro Lys Ile Arg Gly Ala Ile Ala
145                 150                 155                 160

Gly Leu Phe Gln Leu Ser Val Thr Leu Gly Ile Leu Ile Leu Tyr Tyr
                165                 170                 175

Val Gly Tyr Gly Ala His Phe Ile Thr Ser Ala Ser Ser Phe Arg Leu
            180                 185                 190

Thr Trp Gly Ile Gln Leu Val Pro Gly Phe Val Leu Leu Val Ala Thr
        195                 200                 205

Phe Phe Leu Pro Glu Ser Pro Arg Trp Leu Ala Asn Lys Gly Phe Trp
    210                 215                 220

Glu Lys Ala Thr Tyr Asn Ile Cys Arg Ile Asn Asn Thr Asp Pro Asp
225                 230                 235                 240

Asn Ile Ser Glu Glu Val Ala Ile Gln Leu Glu Glu Met Asn Thr Gln
                245                 250                 255

Val Met Asp Asp Lys Glu Ala Asp Ser Phe Thr Tyr Ala Asn Leu Phe
            260                 265                 270

Arg Lys Lys Thr Ile Lys Lys Thr Ile Val Gly Met Ser Ala Gln Met
        275                 280                 285

Trp Gln Gln Leu Ser Gly Ile Asn Val Met Met Tyr Tyr Ile Val Tyr
    290                 295                 300

Ile Phe Gln Met Ala Gly Tyr Ser Gly Asn Ala Val Leu Val Ser Gly
305                 310                 315                 320

Ser Ile Asn Tyr Ile Leu Asn Val Ala Met Thr Ile Pro Ala Leu Phe
                325                 330                 335

Val Ile Asp Lys Leu Gly Arg Arg Pro Ile Leu Ile Val Gly Gly Ile
            340                 345                 350

Leu Met Phe Val Trp Leu Phe Ala Val Ala Gly Leu Leu Ser Val Tyr
        355                 360                 365

Ser Val Pro Val Pro Gly Gly Val Gly Gly Asn Glu Thr Val Asn Ile
    370                 375                 380

Met Ile Pro Asp Asn His Lys His Ala Ala Lys Gly Val Ile Ala Cys
385                 390                 395                 400

Cys Tyr Leu Phe Val Cys Thr Phe Ala Pro Thr Trp Gly Ile Gly Ile
                405                 410                 415

Trp Ile Tyr Cys Ser Glu Ile Phe Asn Asn Ser Glu Arg Ala Lys Gly
            420                 425                 430

Ser Ser Leu Ser Ala Ala Val Asn Trp Ile Phe Asn Phe Ala Leu Gly
        435                 440                 445

Leu Phe Val Pro Ser Ala Phe Gln Asn Ile Thr Trp Lys Thr Tyr Leu
    450                 455                 460

Met Phe Gly Ile Phe Ser Val Ala Leu Thr Ile His Thr Phe Leu Met
465                 470                 475                 480

Phe Pro Glu Thr Lys Gly Lys Thr Leu Glu Glu Ile Asp Gln Met Trp
                485                 490                 495

Glu Ala Asn Ile Pro Ala Trp Arg Ser Ala Ser Trp Lys Pro Thr Leu
            500                 505                 510

Pro Ser His Leu His Asp Asp Phe Lys Asn Leu His Thr Gly Glu Ser
        515                 520                 525

Ser Ser Asn Phe Val Glu Asp Asp Gly Lys Ala Glu Met Glu Lys Pro
```

```
              530                 535                 540
Val Val Asp His Ile Glu Ser Thr Asp Lys Ser Leu
545                 550                 555

<210> SEQ ID NO 13
<211> LENGTH: 557
<212> TYPE: PRT
<213> ORGANISM: Debaryomyces hansenii

<400> SEQUENCE: 13

Met Asn Ser Ile Phe Asn Tyr Ser Gly Phe Val Met Lys Phe Thr Ile
1               5                   10                  15

Pro Glu Lys Tyr Leu Leu Glu Asn Lys Val Lys Gly Lys Lys Leu Thr
                20                  25                  30

His Cys Val Val Ala Leu Ser Ala Leu Ala Ile Phe Phe Phe Gly Tyr
            35                  40                  45

Asp Gln Gly Met Met Ala Gly Val Asn Thr Ser Pro Asp Tyr Val Glu
        50                  55                  60

Lys Met Lys Tyr Gly Tyr Phe Asn Glu Asn Gly Asp Val Thr Val Thr
65                  70                  75                  80

Asn Ser Thr Arg Gln Gly Gly Ile Val Ala Ile Tyr Tyr Phe Gly Thr
                85                  90                  95

Leu Val Gly Cys Val Phe Gly Gly Leu Phe Ser Asp Arg His Gly Arg
            100                 105                 110

Ile Lys Ala Ile Ala Leu Gly Ala Leu Ile Ala Ile Phe Gly Ala Ala
        115                 120                 125

Leu Gln Cys Ala Ala Gln Gln Met Ser Trp Met Cys Gly Ala Arg Phe
130                 135                 140

Val Asn Gly Ile Gly Thr Gly Ile Leu Asn Ala Val Val Pro Val Tyr
145                 150                 155                 160

Ser Ser Glu Thr Ala Glu His Thr Ser Arg Gly Ala Phe Ile Ala Ile
                165                 170                 175

Glu Phe Thr Leu Asn Ile Phe Gly Val Cys Val Ala Tyr Trp Leu Glu
            180                 185                 190

Tyr Gly Leu Ser Tyr Ile Asp Ser Gly Phe Ser Ala Phe Gln Trp Arg
        195                 200                 205

Phe Pro Ile Ala Phe Gln Ile Ile Pro Leu Leu Val Leu Leu Gly Ile
210                 215                 220

Val Trp Phe Phe Pro Glu Ser Pro Arg Trp Leu Val Lys Asn Gly Glu
225                 230                 235                 240

Glu Asp His Ala Lys Arg Ile Leu Leu Asn Met Arg Gly Val Glu Arg
                245                 250                 255

Gly Asn Gln Glu Phe Ala Glu Ile Val Gly Ala Met Arg Phe Glu Gln
            260                 265                 270

Glu Ser Ala Leu Ser Ser Ser Tyr Trp Arg Met Phe Leu Gly Tyr Phe
        275                 280                 285

Pro Asp Lys Asp Ser Lys Lys Ser Ala Lys Ala Thr Leu His Ile
290                 295                 300

Ala Arg Arg Val Gln Ile Val Ile Trp Met Gln Ile Phe Gln Glu Trp
305                 310                 315                 320

Val Gly Ile Ala Gly Val Thr Val Tyr Gln Pro Glu Ile Phe Lys Gln
                325                 330                 335

Ala Gly Phe Gly Thr Arg Lys Ser Ala Trp Leu Ser Gly Val Asn Asn
            340                 345                 350
```

```
Ile Phe Tyr Cys Leu Ser Thr Leu Ile Asn Phe Phe Thr Val Asp Arg
            355                 360                 365

Phe Gly Arg Arg Phe Thr Leu Phe Trp Gly Ala Ile Gly Gln Gly Ile
370                 375                 380

Ser Met Phe Leu Ala Gly Gly Phe Ser Lys Leu Gln Gln Lys Asn Pro
385                 390                 395                 400

Lys Asn Ser Ser Tyr Gly Ala Ala Ala Ser Phe Val Phe Ile Tyr
            405                 410                 415

Thr Ser Ile Phe Gly Ala Thr Trp Leu Ala Val Pro Trp Leu Tyr Pro
            420                 425                 430

Thr Glu Ile Phe Pro Leu Lys Val Arg Ala Gln Gly Asn Ala Phe Gly
            435                 440                 445

Val Val Gly Trp Ser Ile Gly Asn Gly Trp Leu Thr Leu Leu Cys Pro
            450                 455                 460

Ile Met Phe Ser Lys Ile Gly Glu Lys Thr Leu Tyr Ile Phe Gly Ala
465                 470                 475                 480

Cys Asn Phe Ile Ser Leu Ala Leu Val Tyr Leu Phe Cys Pro Glu Thr
            485                 490                 495

Ala Asn Arg Thr Leu Glu Asp Ile Asp Tyr Leu Phe Ala Asn Asp Ser
            500                 505                 510

Trp Leu Ala Ser Lys Ser Glu Ala Asp Phe Lys Arg Ile Lys Ile Glu
            515                 520                 525

Gln Val Asp Lys Gln Val Gly Arg Glu Lys Gln Ile Ile Asp Ile Asp
            530                 535                 540

Ser Ser Glu Lys Glu Asn Phe Ser Thr Glu His Phe Glu
545                 550                 555

<210> SEQ ID NO 14
<211> LENGTH: 513
<212> TYPE: PRT
<213> ORGANISM: Aspergillus niger

<400> SEQUENCE: 14

Met Tyr Arg Ile Ser Asn Ile Tyr Val Leu Ala Gly Phe Gly Thr Ile
1               5                   10                  15

Gly Gly Ala Leu Phe Gly Phe Asp Val Ser Ser Met Ser Ala Trp Ile
            20                  25                  30

Gly Thr Asp Gln Tyr Leu Glu Tyr Phe Asn His Pro Asp Ser Asp Leu
        35                  40                  45

Gln Gly Gly Ile Thr Ala Ser Met Ser Ala Gly Ser Phe Ala Gly Ala
    50                  55                  60

Leu Ala Ala Gly Phe Ile Ser Asp Arg Ile Gly Arg Arg Tyr Ser Leu
65                  70                  75                  80

Met Leu Ala Cys Cys Ile Trp Val Ile Gly Ala Ile Gln Cys Ser
                85                  90                  95

Ala Gln Asn Val Ala His Leu Val Ala Gly Arg Val Ile Ser Gly Leu
            100                 105                 110

Ser Val Gly Ile Thr Ser Ser Gln Val Cys Val Tyr Leu Ala Glu Leu
        115                 120                 125

Ala Pro Ala Arg Ile Arg Gly Arg Ile Val Gly Ile Gln Gln Trp Ala
    130                 135                 140

Ile Glu Trp Gly Met Leu Ile Met Tyr Leu Ile Ser Tyr Gly Cys Gly
145                 150                 155                 160

Gln Gly Leu Ala Gly Ala Ala Ser Phe Arg Val Ser Trp Gly Val Gln
                165                 170                 175
```

```
Gly Ile Pro Ala Leu Ile Leu Ala Ala Leu Pro Phe Phe Pro Glu
            180                 185                 190

Ser Pro Arg Trp Leu Ala Ser Lys Glu Arg Trp Glu Glu Ala Leu Asp
        195                 200                 205

Thr Leu Ala Leu Leu His Ala Lys Gly Asp Arg Asn Asp Pro Val Val
    210                 215                 220

Gln Val Glu Tyr Glu Glu Val Gln Ala Ala Arg Ile Ala Gln Glu
225                 230                 235                 240

Ala Lys Asp Ile Ser Phe Phe Ser Leu Phe Gly Pro Lys Ile Trp Lys
                245                 250                 255

Arg Thr Leu Cys Gly Val Ser Ala Gln Val Trp Gln Gln Leu Leu Gly
            260                 265                 270

Gly Asn Val Ala Met Tyr Tyr Val Val Tyr Ile Phe Asn Met Ala Gly
        275                 280                 285

Met Ser Gly Asn Thr Thr Leu Tyr Ser Ser Ala Ile Gln Tyr Val Ile
    290                 295                 300

Phe Leu Val Thr Thr Gly Thr Ile Leu Pro Phe Val Asp Arg Ile Gly
305                 310                 315                 320

Arg Arg Leu Leu Leu Leu Thr Gly Ser Val Leu Cys Met Ala Cys His
                325                 330                 335

Phe Ala Ile Ala Gly Leu Met Ala Ser Arg Gly His His Val Asp Ser
            340                 345                 350

Val Asp Gly Asn Ala Asn Leu Lys Trp Ser Ile Thr Gly Pro Pro Gly
        355                 360                 365

Lys Gly Val Ile Ala Cys Ser Tyr Ile Phe Val Ala Val Tyr Gly Phe
    370                 375                 380

Thr Trp Ala Pro Val Ala Trp Ile Tyr Ala Ser Glu Val Phe Pro Leu
385                 390                 395                 400

Lys Tyr Arg Ala Lys Gly Val Gly Leu Ser Ala Ala Gly Asn Trp Ile
                405                 410                 415

Phe Asn Phe Ala Leu Ala Tyr Phe Val Ala Pro Ala Phe Thr Asn Ile
            420                 425                 430

Gln Trp Lys Thr Tyr Ile Ile Phe Gly Val Phe Cys Thr Val Met Thr
        435                 440                 445

Phe His Val Phe Phe Tyr Pro Glu Thr Ala Arg Arg Ser Leu Glu
    450                 455                 460

Asp Ile Asp Leu Met Phe Glu Thr Asp Met Lys Pro Trp Lys Thr His
465                 470                 475                 480

Gln Ile His Asp Arg Phe Gly Glu Glu Val Glu Arg His Lys His Lys
                485                 490                 495

Asp Met Ala Asp Gln Glu Lys Gly Val Val Ser Thr His Asp Glu Met
            500                 505                 510

Ala

<210> SEQ ID NO 15
<211> LENGTH: 511
<212> TYPE: PRT
<213> ORGANISM: Penicillium chrysogenum

<400> SEQUENCE: 15

Met Tyr Thr Ile Thr Asn Ile Tyr Val Leu Ala Ala Phe Gly Thr Ile
1               5                   10                  15

Gly Gly Ala Leu Phe Gly Phe Asp Val Ser Ser Met Ser Ala Trp Ile
            20                  25                  30
```

```
Gly Val Asp Thr Tyr Thr Asp Tyr Phe Asp Ser Pro Asp Ser Asn Leu
        35                  40                  45

Gln Gly Gly Ile Thr Ala Ser Met Ser Ala Gly Ser Phe Ala Gly Ser
        50                  55                  60

Ile Ala Ala Gly Trp Leu Ala Asp Ile Leu Gly Arg Arg Tyr Ala Leu
65                  70                  75                  80

Met Ile Ala Ser Leu Val Trp Ile Val Gly Ala Val Val Gln Cys Ser
                85                  90                  95

Ala Gln Asn Val Thr His Leu Val Ala Gly Arg Val Val Ser Gly Leu
            100                 105                 110

Ala Val Gly Val Thr Ser Ser Gln Thr Cys Val Tyr Leu Ser Glu Leu
            115                 120                 125

Ala Pro Ala Arg Ile Arg Gly Arg Ile Val Gly Ile Gln Gln Trp Ala
            130                 135                 140

Ile Glu Trp Gly Ile Leu Ile Met Tyr Leu Ile Ala Tyr Gly Cys Val
145                 150                 155                 160

Val Gly Val Ser Gly Pro Ala Ala Phe Arg Ile Cys Trp Gly Val Gln
                165                 170                 175

Ala Val Pro Gly Leu Ile Leu Phe Ile Ala Leu Phe Phe Pro Glu
            180                 185                 190

Ser Pro Arg Trp Leu Ala Ser Gln Glu Arg Trp Glu Glu Ala Leu Asp
            195                 200                 205

Thr Leu Ala Ile Ile His Ala Asn Gly Asp Arg His Asp Pro Val Val
            210                 215                 220

Gln Val Glu Phe Glu Glu Val Gln Glu Ala Val Arg Val Ala His Glu
225                 230                 235                 240

Ser Arg Asp Val Ser Phe Met Ala Leu Phe Gly Pro Arg Val Trp Lys
                245                 250                 255

Arg Thr Met Cys Gly Met Ser Val Gln Met Trp Gln Gln Leu Leu Gly
            260                 265                 270

Gly Asn Val Ala Met Tyr Tyr Val Val Tyr Ile Phe Glu Met Ala Gly
            275                 280                 285

Met Thr Gly Asn Thr Thr Leu Trp Ser Ser Ala Ile Gln Tyr Val Ile
            290                 295                 300

Phe Leu Val Thr Thr Gly Cys Met Leu Pro Phe Ile Asp Arg Val Gly
305                 310                 315                 320

Arg Arg Asn Leu Leu Leu Ile Gly Ser Val Thr Cys Met Val Val His
                325                 330                 335

Tyr Ile Ile Ala Ala Val Met Ala Ser Lys Gly Lys Pro Val Pro Asp
            340                 345                 350

Val Asn Gly Asn Ala Asn Leu Thr Trp Glu Ile Lys Gly Ser Ala Gly
            355                 360                 365

Met Thr Val Ile Ala Phe Ser Tyr Ile Phe Thr Gly Ile Tyr Gly Leu
            370                 375                 380

Thr Trp Ala Pro Thr Ala Trp Ile Tyr Ala Ala Glu Val Phe Pro Leu
385                 390                 395                 400

Lys Phe Arg Ala Lys Gly Val Gly Leu Ser Ala Ala Thr Asn Trp Ile
                405                 410                 415

Phe Asn Phe Ala Leu Ala Tyr Phe Val Ala Pro Ala Phe His Asn Ile
            420                 425                 430

Gln Trp Lys Thr Tyr Ile Ile Phe Gly Val Phe Cys Thr Val Met Thr
            435                 440                 445
```

Phe His Val Phe Phe Met Tyr Pro Glu Thr Val Gly Arg Ser Leu Glu
450                         455                     460

Glu Ile Asp Leu Val Phe Glu Thr Asp Val Lys Pro Trp Arg Thr His
465                     470                  475                 480

Lys Ile Gly Asp Ile Phe Gly Glu Glu Ile Glu Arg Arg Lys Glu Leu
                    485                  490                 495

Gly Ala Lys Thr Glu Thr Gly Gly Ala Thr His Glu Glu Val Val
500                      505                  510

<210> SEQ ID NO 16
<211> LENGTH: 538
<212> TYPE: PRT
<213> ORGANISM: Pichia guilliermondii

<400> SEQUENCE: 16

Met Gly Tyr Glu Asp Lys Leu Val Ala Pro Ala Leu Lys Phe Arg Asn
1               5                   10                  15

Phe Ile Asp Arg Thr Pro Asn Thr Tyr Asn Val Tyr Val Ile Ala Ser
                20                  25                  30

Ile Ser Cys Ile Ser Gly Ala Met Phe Gly Phe Asp Ile Ser Ser Met
            35                  40                  45

Ser Val Phe Val Gly Gln Thr Pro Tyr Leu Asn Phe Phe His Ser Pro
50                      55                  60

Lys Ser Asp Leu Gln Gly Phe Ile Thr Ala Ala Met Ser Leu Gly Ser
65                  70                  75                  80

Phe Phe Gly Ser Leu Leu Ser Ser Phe Val Ser Glu Pro Phe Gly Arg
                85                  90                  95

Arg Ala Ser Leu Leu Ile Cys Gly Phe Leu Trp Cys Val Gly Ala Ala
                100                 105                 110

Ile Gln Cys Ser Ser Gln Asn Val Ala Gln Leu Ile Ile Gly Arg Ile
            115                 120                 125

Ile Ser Gly Phe Gly Val Gly Phe Gly Ser Ser Val Ala Pro Val Tyr
            130                 135                 140

Gly Ser Glu Met Ala Pro Arg Lys Ile Arg Gly Thr Ile Gly Gly Phe
145                 150                 155                 160

Phe Gln Phe Ser Val Thr Leu Gly Ile Phe Ile Met Phe Leu Ile Gly
                165                 170                 175

Tyr Gly Cys Ser Lys Ile Asp Ala Val Gly Ser Phe Arg Ile Pro Trp
            180                 185                 190

Gly Val Gln Ile Val Pro Gly Leu Phe Leu Leu Gly Cys Phe Phe
            195                 200                 205

Ile Pro Glu Ser Pro Arg Trp Leu Ala Lys Gln Gly Tyr Trp Glu Glu
210                 215                 220

Ala Glu Ile Ile Val Ala Asn Ile Gln Ala Lys Gly Asn Arg Glu Asp
225                 230                 235                 240

Pro Asp Val Leu Ile Glu Ile Ser Glu Ile Lys Glu Gln Leu Leu Leu
                245                 250                 255

Asp Glu His Ala Lys Ala Phe Thr Tyr Ala Asp Leu Phe Ser Lys Lys
            260                 265                 270

Tyr Leu Pro Arg Thr Ile Thr Ala Ile Ser Ala Gln Ile Trp Gln Gln
            275                 280                 285

Leu Thr Gly Met Asn Val Met Met Tyr Tyr Ile Val Tyr Ile Phe Gln
290                 295                 300

Met Ala Gly Tyr Glu Gly Asp Thr Asn Leu Ile Pro Ser Leu Ile Gln
305                 310                 315                 320

Tyr Ile Ile Asn Thr Val Val Thr Ile Pro Ser Leu Tyr Leu Leu Asp
                325                 330                 335

Arg Val Gly Arg Arg Lys Met Leu Leu Phe Gly Ala Ala Met Met
            340                 345                 350

Ala Trp Gln Phe Gly Val Ala Gly Ile Leu Ala Thr Tyr Ser Glu Pro
            355                 360                 365

Tyr Asp Leu Asn Asp Thr Val Lys Ile Thr Ile Pro Asp Lys His Lys
        370                 375                 380

Ser Ala Ala Lys Gly Val Ile Ala Cys Cys Tyr Leu Phe Val Ala Ser
385                 390                 395                 400

Phe Ala Ser Thr Trp Gly Val Gly Ile Trp Val Tyr Cys Ser Glu Val
            405                 410                 415

Trp Gly Asp Ser Gln Ser Arg Gln Arg Gly Ala Ala Val Ala Thr Ala
            420                 425                 430

Ala Asn Trp Ile Phe Asn Phe Ala Ile Gly Met Phe Thr Pro Ser Ser
            435                 440                 445

Phe Lys Asn Ile Thr Trp Lys Thr Tyr Cys Ile Tyr Ala Thr Phe Cys
    450                 455                 460

Gly Cys Met Phe Ile His Val Phe Phe Phe Pro Glu Thr Lys Gly
465                 470                 475                 480

Lys Arg Leu Glu Glu Ile Ala Gln Ile Trp Glu Glu Lys Val Pro Ala
                485                 490                 495

Trp Lys Thr Ser Lys Trp Gln Pro His Val Pro Leu Leu Ser Asp His
            500                 505                 510

Glu Leu Ala Glu Lys Met Ser Thr Lys His Asp Glu Asn Met Leu Gln
            515                 520                 525

Ser Gln Ser Ser Glu Glu Lys Pro Thr Val
            530                 535

<210> SEQ ID NO 17
<211> LENGTH: 555
<212> TYPE: PRT
<213> ORGANISM: Aspergillus flavus

<400> SEQUENCE: 17

Met Cys Asp Gln Ile Pro Lys Trp Asn Val Val His Arg Leu Glu Lys
1               5                   10                  15

Arg Lys Leu Leu Ile Gly Ile Asn Ser Val Ala Ala Leu Ser Ile Leu
                20                  25                  30

Phe Phe Gly Tyr Asp Gln Gly Met Met Ala Gly Val Asn Asn Ser Lys
            35                  40                  45

Asp Tyr Ile Asp Leu Met Gly Phe Gly Tyr Thr Glu Met Lys Asp Gly
        50                  55                  60

Tyr Leu Thr Pro Val Val Thr Asp Ser Leu Leu Gln Gly Gly Ile Val
65                  70                  75                  80

Ser Val Tyr Tyr Leu Gly Thr Leu Phe Gly Ala Leu Leu Gly Gly Trp
                85                  90                  95

Ile Gly Asp Arg Ile Gly Arg Ile Lys Thr Ile Ala Ala Gly Ala Leu
            100                 105                 110

Trp Ala Ile Leu Gly Ala Ala Leu Gln Cys Ser Ala Gln Asn His Asn
            115                 120                 125

Trp Met Ile Cys Ser Arg Phe Ile Asn Gly Ile Gly Thr Gly Ile Leu
            130                 135                 140

Asn Ala Ile Val Pro Val Trp Ala Thr Glu Thr Ala Glu His Thr Ser 145                 150                 155                 160

Arg Gly Gln Phe Ile Ala Ile Glu Phe Thr Leu Asn Ile Phe Gly Val
                165                 170                 175

Val Leu Ala Tyr Trp Leu Glu Phe Gly Leu Ser Phe Ile Asp Gly Gly
                180                 185                 190

Arg Ser Pro Phe Arg Trp Arg Pro Ile Ala Phe Gln Ile Ile Phe
                195                 200                 205

Leu Val Leu Leu Phe Val Val Trp Phe Phe Pro Glu Ser Pro Arg
    210                 215                 220

Trp Leu Val Lys Val Gly Arg Glu Gln Glu Ala Arg Tyr Ile Leu Gly
225                 230                 235                 240

Arg Leu Arg Gly Ser Ser Asp Glu Asp Ala Val Arg Ala Glu Ala Glu
                245                 250                 255

Phe Arg Asp Ile Gln Asn Val Ala Glu Met Glu Lys Ser Met Asn His
                260                 265                 270

Ser Thr Ser Tyr Leu Ala Met Leu Phe Gly Tyr Lys Thr Gly Lys Leu
                275                 280                 285

His Leu Gly Arg Arg Val Gln Leu Val Ile Trp Leu Gln Ile Met Gln
                290                 295                 300

Glu Trp Val Gly Ile Ala Gly Val Thr Val Tyr Ala Pro Thr Ile Phe
305                 310                 315                 320

Ser Ile Ala Gly Phe Asp Ser Met Lys Ser Gln Trp Ile Ser Gly Leu
                325                 330                 335

Asn Asn Val Phe Tyr Met Phe Ala Thr Leu Val Cys Val Phe Thr Leu
                340                 345                 350

Asp Arg Ile Gly Arg Arg Trp Thr Leu Tyr Trp Gly Ser Ile Ala Gln
                355                 360                 365

Gly Ile Ala Met Phe Leu Ala Gly Gly Phe Ser Arg Leu Ala Ile Asp
                370                 375                 380

Ala Arg Ala Asp Gly Asn Ile Ser Arg Ala Asn Ser Phe Gly Ala Ala
385                 390                 395                 400

Ala Ala Ser Met Val Phe Ile Phe Thr Ser Val Phe Gly Ala Thr Trp
                405                 410                 415

Leu Thr Val Val Pro Trp Ile Tyr Pro Ala Glu Ile Tyr Pro Leu Ala
                420                 425                 430

Val Arg Ala Lys Gly Asn Ala Trp Gly Val Val Gly Trp Ser Ile Gly
                435                 440                 445

Asn Gly Trp Leu Thr Leu Leu Cys Pro Val Met Phe Glu Ala Ile Gly
                450                 455                 460

Glu Lys Thr Leu Tyr Val Phe Ala Ala Ser Asn Val Ile Thr Ile Pro
465                 470                 475                 480

Met Val Trp Ala Leu Tyr Pro Glu Ser Asn Gln Arg Thr Leu Glu Asp
                485                 490                 495

Met Asp Leu Leu Phe Ala Ala Glu Thr Pro Trp Val Trp Asp Ala Glu
                500                 505                 510

Arg Thr Phe Ala Arg Leu Lys Ala Glu Asn Pro Gly Tyr Ile Glu Thr
                515                 520                 525

Ala Asn Arg Lys Asn Ser Ala Val Asp Pro Glu Met Gly Lys Pro Thr
                530                 535                 540

Asp Ala His Glu Glu His Ala Ser Ser Ala Ser
545                 550                 555

<210> SEQ ID NO 18

<211> LENGTH: 544
<212> TYPE: PRT
<213> ORGANISM: Candida lusitaniae

<400> SEQUENCE: 18

```
Met Gly Tyr Glu Glu Lys Leu Val Ala Pro Ala Leu Lys Leu Arg Arg
1               5                   10                  15

Phe Leu Asp Arg Thr Pro Asn Thr Tyr Asn Val Tyr Phe Ile Ala Ser
            20                  25                  30

Ile Ser Cys Ile Ser Gly Met Phe Gly Phe Asp Ile Ser Ser Met
        35                  40                  45

Ser Val Phe Val Ser Asp Lys Pro Tyr Leu Asn Tyr Phe Asp His Pro
    50                  55                  60

Ser Ser Val Met Gln Gly Phe Ile Thr Ala Ala Met Ser Leu Gly Ser
65                  70                  75                  80

Phe Phe Gly Ser Leu Ser Ser Phe Val Ser Glu Pro Phe Gly Arg
                85                  90                  95

Arg Ala Ser Leu Leu Ile Cys Gly Phe Leu Trp Cys Val Gly Ala Ala
            100                 105                 110

Ile Gln Cys Ser Ala Gln Asn Arg Ala Gln Leu Ile Ile Gly Arg Ile
        115                 120                 125

Ile Ser Gly Trp Gly Val Gly Phe Gly Ser Ser Val Ser Pro Val Tyr
    130                 135                 140

Gly Ser Glu Leu Ser Pro Arg Lys Ile Arg Gly Phe Val Gly Gly Met
145                 150                 155                 160

Phe Gln Phe Ser Val Thr Phe Gly Ile Leu Ile Met Phe Leu Ile Ala
                165                 170                 175

Tyr Gly Met Ser His Val His Gly Lys Ala Ser Phe Arg Val Ser Trp
            180                 185                 190

Gly Val Gln Ile Val Pro Gly Leu Val Leu Leu Ile Gly Leu Phe Phe
        195                 200                 205

Ile Pro Glu Ser Pro Arg Trp Leu Ala Lys Gln Gly Tyr Trp Asp Glu
    210                 215                 220

Ala Glu Phe Ile Val Ala Lys Ile Gln Ala Lys Gly Asn Arg Glu Asp
225                 230                 235                 240

Pro Glu Val Gln Ile Glu Leu Ser Glu Ile Lys Glu Gln Leu Leu Leu
                245                 250                 255

Glu Glu His Ala Lys Asn Phe Thr Tyr Ala Asp Leu Phe Ser Pro Lys
            260                 265                 270

Tyr Arg Val Arg Thr Val Thr Ala Val Phe Ala Gln Ile Trp Gln Gln
        275                 280                 285

Leu Thr Gly Met Asn Val Met Met Tyr Ile Val Tyr Ile Phe Glu
    290                 295                 300

Met Ala Gly Tyr Glu Gly Asn Thr Asn Leu Ile Pro Ser Leu Ile Gln
305                 310                 315                 320

Tyr Ile Ile Asn Ser Ala Val Thr Val Pro Ser Leu Tyr Leu Leu Asp
                325                 330                 335

Lys Val Gly Arg Arg Thr Leu Leu Leu Phe Gly Ala Ala Gly Met Met
            340                 345                 350

Ala Phe Gln Phe Ala Val Ala Gly Leu Leu Ala Thr Tyr Ser Ile Pro
        355                 360                 365

His Glu Tyr Lys Gly Asn Asp Thr Val Arg Ile Thr Ile Pro Lys Lys
    370                 375                 380

Asn Lys Pro Ala Ala Arg Gly Val Ile Ala Cys Cys Tyr Leu Phe Val
```

```
                385                 390                 395                 400
Val Cys Phe Ala Ser Thr Trp Gly Val Gly Ile Trp Val Tyr Cys Ser
                    405                 410                 415

Glu Val Trp Gly Asp Asn Arg Ser Arg Gln Arg Gly Ala Ser Leu Ser
            420                 425                 430

Thr Ser Ala Asn Trp Ile Phe Asn Phe Ala Ile Ala Met Phe Thr Pro
                435                 440                 445

Ser Ser Phe Lys Asn Ile Thr Trp Lys Thr Tyr Ile Ile Tyr Ala Val
        450                 455                 460

Phe Cys Cys Cys Met Phe Val His Val Phe Cys Phe Pro Glu Thr
465                 470                 475                 480

Arg Gly Lys Arg Leu Glu Ile Ala Gln Ile Trp Asp Glu Lys Val
                485                 490                 495

Pro Ala Trp Lys Thr Arg Asn Trp Gln Pro His Val Pro Leu Leu Ser
            500                 505                 510

Asp Ala Gln Leu Glu Glu Lys Leu Asn Val Asn His Ala Glu Asn Ala
        515                 520                 525

Gly Glu Asp Lys Ala Val Gln Ser His Ser Ser Asp Gly Gln Val
530                 535                 540
```

<210> SEQ ID NO 19
<211> LENGTH: 545
<212> TYPE: PRT
<213> ORGANISM: Candida albicans

<400> SEQUENCE: 19

```
Met Lys Ser Pro Leu Glu Leu Ala Leu Gly Thr Ala Leu Lys Ile
1               5                   10                  15

Ser Thr Phe Leu Asp Lys Leu Pro Lys Ile Tyr Asn Val Tyr Phe Ile
            20                  25                  30

Ala Ser Ile Ser Thr Ile Ala Gly Met Met Phe Gly Phe Asp Ile Ser
                35                  40                  45

Ser Met Ser Ala Phe Ile Gly Thr Glu Thr Tyr Met Asp Phe Phe Asn
        50                  55                  60

Ser Pro Gly Ser Asp Ile Gln Gly Phe Ile Thr Ser Ser Met Ala Leu
65                  70                  75                  80

Gly Ser Phe Phe Gly Ser Ile Ala Ser Ser Phe Ile Ser Glu Pro Phe
                85                  90                  95

Gly Arg Arg Leu Ser Leu Ile Ile Cys Ala Phe Phe Trp Met Val Gly
            100                 105                 110

Ala Ala Ile Gln Ser Ser Val Gln Asn Arg Ala Gln Leu Ile Ile Gly
        115                 120                 125

Arg Ile Ile Ser Gly Val Gly Val Gly Phe Gly Ser Ser Val Ala Thr
    130                 135                 140

Ile Tyr Gly Ala Glu Leu Ala Pro Arg Lys Ile Arg Gly Phe Ile Gly
145                 150                 155                 160

Gly Met Phe Gln Phe Phe Val Thr Leu Gly Ile Leu Ile Met Phe Tyr
                165                 170                 175

Leu Ser Phe Gly Leu Gly His Ile Lys Gly Val Ala Ser Phe Arg Ile
            180                 185                 190

Ala Trp Gly Leu Gln Ile Val Pro Gly Leu Met Leu Phe Ile Gly Cys
        195                 200                 205

Phe Phe Ile Pro Glu Ser Pro Arg Trp Leu Ala Lys Gln Asn Arg Trp
    210                 215                 220
```

-continued

```
Glu Gln Ala Glu Tyr Ile Val Ser Arg Ile Gln Ala Lys Gly Asn Arg
225                 230                 235                 240

Glu Asp Pro Asp Val Leu Ile Glu Ile Ser Glu Ile Lys Asp Gln Leu
            245                 250                 255

Leu Ile Glu Glu Ala Ala Lys Ser Val Ser Tyr Ala Thr Leu Phe Arg
        260                 265                 270

Lys Lys Tyr Leu Leu Arg Thr Phe Thr Ala Ile Phe Ala Gln Ile Trp
    275                 280                 285

Gln Gln Leu Thr Gly Met Asn Val Met Met Tyr Tyr Ile Val Tyr Ile
290                 295                 300

Phe Gln Met Ala Gly Tyr Ser Gly Asn Ala Asn Leu Val Ala Ser Ser
305                 310                 315                 320

Ile Gln Tyr Val Ile Asn Thr Gly Val Thr Ile Pro Ala Leu Phe Phe
            325                 330                 335

Val Asp Arg Ile Gly Arg Arg Pro Val Leu Ile Thr Gly Ala Val Leu
        340                 345                 350

Met Met Thr Phe Gln Phe Gly Leu Ala Gly Ile Leu Gly Gln Tyr Ser
    355                 360                 365

Val Pro Trp Thr Asp Ser Gly Asn Asp Ser Val Asn Ile Arg Ile Pro
370                 375                 380

Glu Asp Asn Lys Ser Ala Ser Lys Gly Ala Ile Ala Cys Cys Tyr Leu
385                 390                 395                 400

Phe Val Ala Ser Phe Ala Ser Thr Trp Gly Pro Thr Ile Trp Ile Tyr
            405                 410                 415

Cys Ser Glu Ile Trp Gly Asp Asn Arg Val Ala Gln Arg Gly Asn Ser
        420                 425                 430

Leu Ala Thr Ala Ala Asn Trp Ile Leu Asn Phe Ala Ile Gly Met Tyr
    435                 440                 445

Thr Pro Ala Gly Phe Lys Ser Ile Ser Trp Arg Thr Tyr Ile Ile Tyr
450                 455                 460

Gly Val Met Cys Phe Thr Met Ala Ile His Val Tyr Phe Gly Phe Pro
465                 470                 475                 480

Glu Thr Lys Gly Lys Arg Leu Glu Glu Ile Gly Gln Met Trp Glu Glu
            485                 490                 495

His Val Pro Ala Trp Lys Ser Arg Ser Trp Gln Pro His Val Pro Ile
        500                 505                 510

Ala Ser Asp Ala Glu Leu Ala Arg Lys Met Asp Val Glu His Lys Glu
    515                 520                 525

Gly Gly Leu Met Asn Glu Asp Thr Asn Ser Glu Ala Lys Ala Glu Ser
530                 535                 540

Val
545
```

<210> SEQ ID NO 20
<211> LENGTH: 536
<212> TYPE: PRT
<213> ORGANISM: Kluyveromyces marxianus

<400> SEQUENCE: 20

```
Met Thr Leu Lys Asp Lys Leu Leu Arg Asn Ile Glu Phe Lys Gly
1               5                   10                  15

Thr Phe Tyr Ala Lys Phe Pro Gln Ile His Asn Ile Tyr Ala Ile Gly
            20                  25                  30

Val Ile Ser Cys Ile Ser Gly Leu Met Phe Gly Phe Asp Ile Ser Ser
        35                  40                  45
```

-continued

Met Ser Ser Met Ile Gly Thr Glu Thr Tyr Lys Lys Tyr Phe Asp His
        50                  55                  60

Pro Lys Ser Ile Thr Gln Gly Gly Ile Thr Ala Ser Met Ser Gly Gly
65                  70                  75                  80

Ser Phe Leu Gly Ser Leu Leu Ser Pro Ala Ile Ser Asp Thr Phe Gly
                85                  90                  95

Arg Lys Val Ser Leu His Ile Cys Ala Val Leu Trp Ile Val Gly Cys
                100                 105                 110

Ile Leu Gln Ser Ala Ala Gln Asp Gln Pro Met Leu Ile Ala Gly Arg
            115                 120                 125

Val Ile Ala Gly Leu Gly Ile Gly Phe Gly Ser Gly Ala Pro Ile
            130                 135                 140

Tyr Cys Ser Glu Ile Ser Pro Pro Lys Val Arg Gly Leu Ile Thr Gly
145                 150                 155                 160

Leu Phe Gln Phe Ser Ile Thr Val Gly Ile Met Ile Leu Phe Tyr Val
                165                 170                 175

Gly Tyr Gly Cys His Phe Leu Ser Gly Asn Leu Ser Phe Arg Leu Thr
                180                 185                 190

Trp Gly Leu Gln Val Ile Pro Gly Phe Val Leu Val Gly Val Leu
            195                 200                 205

Phe Leu Pro Glu Ser Pro Arg Trp Leu Ala Asn His Asp Arg Trp Glu
        210                 215                 220

Glu Thr Glu Ser Ile Val Ala Lys Val Val Ala Lys Gly Asn Val Asp
225                 230                 235                 240

Asp Glu Glu Val Lys Phe Gln Leu Glu Glu Ile Lys Glu Gln Val Ile
                245                 250                 255

Leu Asp Ala Ala Ala Lys Asn Phe Ser Phe Lys Asp Leu Leu Arg Pro
            260                 265                 270

Lys Thr Arg Lys Lys Leu Phe Val Gly Val Cys Ala Gln Met Trp Gln
        275                 280                 285

Gln Leu Cys Gly Met Asn Val Met Met Tyr Tyr Ile Val Tyr Val Phe
        290                 295                 300

Asn Met Ala Gly Tyr Thr Gly Asn Thr Asn Leu Val Ala Ser Ser Ile
305                 310                 315                 320

Gln Tyr Val Leu Asn Val Leu Met Thr Phe Pro Ala Leu Phe Leu Ile
                325                 330                 335

Asp Lys Val Gly Gly Leu Leu Ala Ser Tyr Ser Val Pro Ala Pro Asn
                340                 345                 350

Gly Val Asn Gly Asp Asp Thr Val Thr Ile Arg Ile Pro Asp Lys His
            355                 360                 365

Lys Ser Ala Ala Lys Gly Val Ile Ala Cys Ser Tyr Leu Phe Val Cys
        370                 375                 380

Ser Phe Ala Pro Thr Trp Gly Ile Gly Ile Trp Ile Tyr Cys Ser Glu
385                 390                 395                 400

Ile Phe Asn Asn Met Glu Arg Ala Lys Gly Ser Ser Val Ala Ala Ala
                405                 410                 415

Thr Asn Trp Ala Phe Asn Phe Ala Leu Ala Met Phe Val Pro Ser Ala
                420                 425                 430

Phe Lys Asn Ile Ser Trp Lys Thr Tyr Ile Val Phe Gly Val Phe Ser
            435                 440                 445

Val Ala Leu Thr Val Gln Thr Tyr Phe Met Phe Pro Glu Thr Arg Gly
        450                 455                 460

```
Lys Thr Leu Glu Glu Ile Asp Gln Met Trp Val Asp Asn Ile Pro Ala
465                 470                 475                 480

Trp Lys Thr Ser Ser Tyr Ile Pro Gln Leu Pro Ile Ile Glu Asp Glu
            485                 490                 495

Phe Gly Asn Lys Leu Gly Leu Leu Gly Asn Pro Gln His Leu Glu His
        500                 505                 510

Val Lys Ser Val Glu Lys Asp Thr Val Val Glu Lys Leu Glu Ser Ser
    515                 520                 525

Glu Ala Asn Ser Ser Ser Ser Val
    530                 535

<210> SEQ ID NO 21
<211> LENGTH: 542
<212> TYPE: PRT
<213> ORGANISM: Pichia stipitis

<400> SEQUENCE: 21

Met Ser Tyr Glu Asp Lys Leu Val Gln Pro Ala Leu Lys Phe Arg Thr
1               5                   10                  15

Phe Leu Asp Arg Leu Pro Asn Ile Tyr Asn Val Tyr Ile Ile Ala Ser
            20                  25                  30

Ile Ser Cys Ile Ser Gly Met Met Phe Gly Phe Asp Ile Ser Ser Met
        35                  40                  45

Ser Ala Phe Ile Gly Glu Asp Asp Tyr Lys Asn Phe Phe Asn Asn Pro
50                  55                  60

Gly Ser Asp Ile Gln Gly Phe Ile Thr Ser Cys Met Ala Leu Gly Ser
65                  70                  75                  80

Phe Phe Gly Ser Ile Val Ser Ser Phe Ile Ser Glu Pro Phe Gly Arg
                85                  90                  95

Arg Ala Ser Leu Leu Leu Cys Ser Phe Phe Trp Met Val Gly Ala Ala
            100                 105                 110

Val Gln Ser Ser Ser Gln Asn Arg Ala Gln Leu Met Ile Gly Arg Ile
        115                 120                 125

Ile Ala Gly Phe Gly Val Gly Phe Gly Ser Ser Val Ala Pro Val Tyr
130                 135                 140

Gly Ser Glu Leu Ala Pro Arg Lys Ile Arg Gly Phe Val Gly Gly Ile
145                 150                 155                 160

Phe Gln Phe Cys Val Thr Leu Gly Ile Leu Ile Met Phe Tyr Ile Cys
                165                 170                 175

Tyr Gly Leu His Phe Ile Asn Gly Val Gly Ser Phe Arg Ile Ala Trp
            180                 185                 190

Gly Leu Gln Ile Val Pro Gly Leu Val Leu Phe Val Gly Cys Phe Phe
        195                 200                 205

Ile Pro Glu Ser Pro Arg Trp Leu Ala Lys His Gly Tyr Trp Asp Glu
210                 215                 220

Ala Glu Phe Ile Val Ala Gln Ile Gln Ala Lys Gly Asn Arg Glu Asp
225                 230                 235                 240

Pro Asp Val Leu Ile Glu Ile Ser Glu Ile Lys Asp Gln Ile Leu Ile
                245                 250                 255

Glu Glu Asn Leu Lys Ser Phe Gly Tyr Val Asp Leu Phe Thr Lys Lys
            260                 265                 270

Tyr Ile Arg Arg Thr Leu Thr Ala Ile Phe Ala Gln Ile Trp Gln Gln
        275                 280                 285

Leu Thr Gly Met Asn Val Met Met Tyr Tyr Ile Val Tyr Ile Phe Asn
290                 295                 300
```

Met Ala Gly Tyr Ser Asn Asn Ala Asn Leu Val Ala Ser Ser Ile Gln
305                 310                 315                 320

Tyr Val Leu Asn Thr Ala Ala Thr Val Pro Ala Leu Phe Leu Met Asp
            325                 330                 335

Tyr Ile Gly Arg Arg Leu Leu Ile Gly Gly Ala Ile Met Met Met
        340                 345                 350

Ile Phe Gln Phe Gly Val Ala Gly Ile Leu Gly Lys Tyr Ser Val Pro
    355                 360                 365

Val Pro Gly Gly Leu Pro Gly Asn Pro Thr Val Thr Ile Gln Ile Pro
    370                 375                 380

Glu Asp Asn Lys Ser Ala Ala Arg Gly Val Ile Ala Cys Cys Tyr Leu
385                 390                 395                 400

Phe Val Val Ser Phe Ala Leu Ser Trp Gly Val Gly Ile Trp Val Tyr
                405                 410                 415

Cys Ser Glu Val Trp Gly Asp Ser Ala Ser Arg Gln Arg Gly Ala Ala
                420                 425                 430

Val Ser Thr Ala Ala Asn Trp Ile Leu Asn Phe Ala Ile Ala Met Tyr
            435                 440                 445

Thr Pro Ser Ser Phe Lys Asn Ile Thr Trp Lys Thr Tyr Ile Ile Tyr
    450                 455                 460

Ala Val Phe Cys Leu Val Met Ala Ile His Val Tyr Phe Gly Phe Pro
465                 470                 475                 480

Glu Thr Lys Gly Lys Arg Leu Glu Val Gly Gln Met Trp Asp Glu
                485                 490                 495

Asn Val Pro Ala Trp Arg Ser Ser Trp Gln Pro Thr Val Pro Leu
                500                 505                 510

Leu Ser Asp Ala Asp Leu Ala His Lys Met Asp Val Ser His Lys Glu
            515                 520                 525

Glu Gln Ser Pro Asp Ala Glu Ser Ser Glu Glu Lys Pro
            530                 535                 540

<210> SEQ ID NO 22
<211> LENGTH: 521
<212> TYPE: PRT
<213> ORGANISM: Candida spp.

<400> SEQUENCE: 22

Met Val Phe Gly Asn Arg Gln Met Pro Lys Phe Tyr Asn Pro Tyr Met
1               5                   10                  15

Ser Ala Ala Val Ala Ala Ile Gly Gly Ser Leu Phe Gly Phe Asp Val
                20                  25                  30

Ser Ser Ile Ser Ala Ile Leu Gly Thr Asp Gln Tyr Asn Thr Tyr Phe
            35                  40                  45

Gly Gln Pro Ser Ser Ile Met Gln Gly Gly Ile Thr Ala Ala Met Ser
    50                  55                  60

Gly Gly Ser Leu Ile Gly Ser Leu Leu Ser Gly Gln Val Cys Asp Ile
65                  70                  75                  80

Leu Gly Arg Lys Lys Thr Ile Ile Tyr Ser Cys Gly Phe Trp Ile Ile
                85                  90                  95

Gly Ser Val Leu Cys Cys Ala Ser Gln Asn Val Ala Met Leu Ile Val
                100                 105                 110

Gly Arg Val Phe Asn Gly Leu Cys Val Gly Phe Thr Ser Ser Gln Val
            115                 120                 125

Pro Val Tyr Ile Ser Glu Leu Ser Arg Lys Asp Val Arg Gly Lys Met

```
            130                 135                 140
Val Gly Ile Gln Gln Trp Ser Ile Glu Trp Gly Ile Leu Ile Met Tyr
145                 150                 155                 160

Tyr Ile Gly Tyr Gly Cys Ser Tyr Ile Lys Ser Asn Ser Ser Phe Arg
                165                 170                 175

Ile Pro Trp Gly Leu Gln Met Ile Pro Ala Val Leu Leu Val Val Leu
                180                 185                 190

Leu Pro Met Phe Pro Glu Ser Pro Arg Trp Leu Gly Ser Lys Gly Arg
                195                 200                 205

Trp Glu Glu Val His Asp Thr Leu Ala Lys Ile His Ala Gly Gly Asn
                210                 215                 220

Arg Glu Asp Pro Ile Val Leu Ala Glu Ile Met Glu Ile Arg Glu Ala
225                 230                 235                 240

Val Glu Ile Glu Gln Asn Ser Asn Ala Ser Tyr Leu Ala Leu Phe Ser
                245                 250                 255

Arg Lys Asn Ile Tyr Arg Thr His Val Gly Ile Met Ala Gln Val Tyr
                260                 265                 270

Gln Gln Leu Ala Gly Gly Asn Val Met Met Tyr Tyr Val Val Tyr Val
                275                 280                 285

Phe Gln Met Ala Gly Leu Thr Gly Ser Ile Asn Leu Ile Ala Ser Ser
                290                 295                 300

Ile Gln Tyr Val Val Phe Leu Ile Phe Thr Phe Pro Val Leu Phe Phe
305                 310                 315                 320

Ile Asp Lys Val Gly Arg Arg Trp Leu Met Ile Gly Gly Ser Ile Ser
                325                 330                 335

Met Gly Thr Cys Ile Trp Ile Val Gly Gly Val Leu Cys Asn Tyr Gly
                340                 345                 350

Glu Tyr Val Asp Glu Val Gly Asn Lys Asn Ile His Ile Thr Leu
                355                 360                 365

Lys Asp Ser His His Ala Ser Val Ala Val Leu Phe Phe Ser Tyr Leu
370                 375                 380

Phe Thr Met Phe Tyr Ser Leu Thr Trp Ala Pro Thr Ala Trp Val Tyr
385                 390                 395                 400

Ala Pro Glu Val Phe Pro Leu Tyr Ile Arg Ser Lys Gly Met Ser Ala
                405                 410                 415

Ala Ala Ala Gly Asn Trp Ser Met Asn Phe Ala Leu Ser Phe Tyr Val
                420                 425                 430

Pro Pro Ala Phe Asp Gln Ile Gly Trp Lys Thr Phe Ala Ile Phe Gly
                435                 440                 445

Val Phe Asn Phe Phe Ser Ala Ile His Ile Tyr Phe Gly Phe Pro Glu
450                 455                 460

Thr Gly Asn Lys Ser Leu Glu Glu Ile Asp Glu Leu Phe Ser Lys Gly
465                 470                 475                 480

Gly Pro Arg Pro Trp Lys Thr Lys Val Gly His Ser His Phe Asp Glu
                485                 490                 495

Lys Val Glu Glu Leu Val His Glu Asp Glu Lys Pro Ser Ala Asp His
                500                 505                 510

Val Glu Ser Val Arg Ser Leu Asp Ser
                515                 520

<210> SEQ ID NO 23
<211> LENGTH: 437
<212> TYPE: PRT
<213> ORGANISM: Piromyces sp.
```

<400> SEQUENCE: 23

```
Met Ala Lys Glu Tyr Phe Pro Gln Ile Gln Lys Ile Lys Phe Glu Gly
1               5                   10                  15

Lys Asp Ser Lys Asn Pro Leu Ala Phe His Tyr Tyr Asp Ala Glu Lys
            20                  25                  30

Glu Val Met Gly Lys Lys Met Lys Asp Trp Leu Arg Phe Ala Met Ala
        35                  40                  45

Trp Trp His Thr Leu Cys Ala Glu Gly Ala Asp Gln Phe Gly Gly Gly
    50                  55                  60

Thr Lys Ser Phe Pro Trp Asn Glu Gly Thr Asp Ala Ile Glu Ile Ala
65                  70                  75                  80

Lys Gln Lys Val Asp Ala Gly Phe Glu Ile Met Gln Lys Leu Gly Ile
                85                  90                  95

Pro Tyr Tyr Cys Phe His Asp Val Asp Leu Val Ser Glu Gly Asn Ser
                100                 105                 110

Ile Glu Glu Tyr Glu Ser Asn Leu Lys Ala Val Ala Tyr Leu Lys
                115                 120                 125

Glu Lys Gln Lys Glu Thr Gly Ile Lys Leu Leu Trp Ser Thr Ala Asn
130                 135                 140

Val Phe Gly His Lys Arg Tyr Met Asn Gly Ala Ser Thr Asn Pro Asp
145                 150                 155                 160

Phe Asp Val Val Ala Arg Ala Ile Val Gln Ile Lys Asn Ala Ile Asp
                165                 170                 175

Ala Gly Ile Glu Leu Gly Ala Glu Asn Tyr Val Phe Trp Gly Gly Arg
                180                 185                 190

Glu Gly Tyr Met Ser Leu Leu Asn Thr Asp Gln Lys Arg Glu Lys Glu
            195                 200                 205

His Met Ala Thr Met Leu Thr Met Ala Arg Asp Tyr Ala Arg Ser Lys
210                 215                 220

Gly Phe Lys Gly Thr Phe Leu Ile Glu Pro Lys Pro Met Glu Pro Thr
225                 230                 235                 240

Lys His Gln Tyr Asp Val Asp Thr Glu Thr Ala Ile Gly Phe Leu Lys
                245                 250                 255

Ala His Asn Leu Asp Lys Asp Phe Lys Val Asn Ile Glu Val Asn His
            260                 265                 270

Ala Thr Leu Ala Gly His Thr Phe Glu His Glu Leu Ala Cys Ala Val
        275                 280                 285

Asp Ala Gly Met Leu Gly Ser Ile Asp Ala Asn Arg Gly Asp Tyr Gln
    290                 295                 300

Asn Gly Trp Asp Thr Asp Gln Phe Pro Ile Asp Gln Tyr Glu Leu Val
305                 310                 315                 320

Gln Ala Trp Met Glu Ile Ile Arg Gly Gly Phe Val Thr Gly Gly
                325                 330                 335

Thr Asn Phe Asp Ala Lys Thr Arg Arg Asn Ser Thr Asp Leu Glu Asp
                340                 345                 350

Ile Ile Ile Ala His Val Ser Gly Met Asp Ala Met Ala Arg Ala Leu
                355                 360                 365

Glu Asn Ala Ala Lys Leu Leu Gln Glu Ser Pro Tyr Thr Lys Met Lys
            370                 375                 380

Lys Glu Arg Tyr Ala Ser Phe Asp Ser Gly Ile Gly Lys Asp Phe Glu
385                 390                 395                 400

Asp Gly Lys Leu Thr Leu Glu Gln Val Tyr Glu Tyr Gly Lys Lys Asn
```

405                 410                 415
Gly Glu Pro Lys Gln Thr Ser Gly Lys Gln Glu Leu Tyr Glu Ala Ile
        420                 425                 430

Val Ala Met Tyr Gln
        435

<210> SEQ ID NO 24
<211> LENGTH: 1669
<212> TYPE: DNA
<213> ORGANISM: Piromyces sp.

<400> SEQUENCE: 24
gtaaatggct aaggaatatt tcccacaaat tcaaaagatt aagttcgaag gtaaggattc    60
taagaatcca ttagccttcc actactacga tgctgaaaag gaagtcatgg gtaagaaaat   120
gaaggattgg ttacgtttcg ccatggcctg gtggcacact ctttgcgccg aaggtgctga   180
ccaattcggt ggaggtacaa agtctttccc atggaacgaa ggtactgatg ctattgaaat   240
tgccaagcaa aaggttgatg ctggtttcga atcatgcaa aagcttggta ttccatacta   300
ctgtttccac gatgttgatc ttgtttccga aggtaactct attgaagaat acgaatccaa   360
ccttaaggct gtcgttgctt acctcaagga aaagcaaaag gaaaccggta ttaagcttct   420
ctggagtact gctaacgtct tcggtcacaa gcgttacatg aacggtgcct ccactaaccc   480
agactttgat gttgtcgccc gtgctattgt tcaaattaag aacgccatag acgccggtat   540
tgaacttggt gctgaaaact acgtcttctg gggtggtcgt gaaggttaca tgagtctcct   600
taacactgac caaaagcgtg aaaaggaaca catggccact atgcttacca tggctcgtga   660
ctacgctcgt tccaagggat tcaagggtac tttcctcatt gaaccaaagc caatggaacc   720
aaccaagcac caatacgatg ttgacactga accgcatt ggtttcctta aggcccacaa   780
cttagacaag gacttcaagg tcaacattga agttaaccac gctactcttg ctggtcacac   840
tttcgaacac gaacttgcct gtgctgttga tgctggtatg ctcggttcca ttgatgctaa   900
ccgtggtgac taccaaaacg gttgggatac tgatcaattc ccaattgatc aatacgaact   960
cgtccaagct tggatggaaa tcatccgtgg tggtggttc gttactggtg gtaccaactt  1020
cgatgccaag actcgtcgta actctactga cctcgaagac atcatcattg cccacgtttc  1080
tggtatggat gctatggctc gtgctcttga aaacgctgcc aagctcctcc aagaatctcc  1140
atacaccaag atgaagaagg aacgttacgc ttccttcgac agtggtattg gtaaggactt  1200
tgaagatggt aagctcaccc tcgaacaagt ttacgaatac ggtaagaaga cggtgaacc   1260 aaagcaaact tctggtaagc aagaactcta cgaagctatt gttgccatgt accaataagt  1320
taatcgtagt taaattggta aaataattgt aaaatcaata aacttgtcaa tcctccaatc  1380
aagtttaaaa gatcctatct ctgtactaat taaatatagt acaaaaaaaa atgtataaac  1440 aaaaaaagt ctaaaagacg gaagaattta atttagggaa aaaataaaaa taataataaa  1500
caatagataa atcctttata ttaggaaaat gtcccattgt attattttca tttctactaa  1560
aaaagaaagt aaataaaaca caagaggaaa ttttccctt ttttttttt tgtaataaat  1620 tttatgcaaa tataaatata aataaataa taaaaaaaaa aaaaaaaa              1669

<210> SEQ ID NO 25
<211> LENGTH: 438
<212> TYPE: PRT
<213> ORGANISM: Bacteroides thetaiotaomicron

<400> SEQUENCE: 25

-continued

```
Met Ala Thr Lys Glu Phe Phe Pro Gly Ile Glu Lys Ile Lys Phe Glu
1               5                   10                  15

Gly Lys Asp Ser Lys Asn Pro Met Ala Phe Arg Tyr Tyr Asp Ala Glu
            20                  25                  30

Lys Val Ile Asn Gly Lys Lys Met Lys Asp Trp Leu Arg Phe Ala Met
                35                  40                  45

Ala Trp Trp His Thr Leu Cys Ala Glu Gly Asp Gln Phe Gly Gly
    50                  55                  60

Gly Thr Lys Gln Phe Pro Trp Asn Gly Asn Ala Asp Ala Ile Gln Ala
65                  70                  75                  80

Ala Lys Asp Lys Met Asp Ala Gly Phe Glu Phe Met Gln Lys Met Gly
                85                  90                  95

Ile Glu Tyr Tyr Cys Phe His Asp Val Asp Leu Val Ser Glu Gly Ala
                100                 105                 110

Ser Val Glu Glu Tyr Glu Ala Asn Leu Lys Glu Ile Val Ala Tyr Ala
            115                 120                 125

Lys Gln Lys Gln Ala Glu Thr Gly Ile Lys Leu Leu Trp Gly Thr Ala
            130                 135                 140

Asn Val Phe Gly His Ala Arg Tyr Met Asn Gly Ala Ala Thr Asn Pro
145                 150                 155                 160

Asp Phe Asp Val Val Ala Arg Ala Ala Val Gln Ile Lys Asn Ala Ile
                165                 170                 175

Asp Ala Thr Ile Glu Leu Gly Gly Glu Asn Tyr Val Phe Trp Gly Gly
                180                 185                 190

Arg Glu Gly Tyr Met Ser Leu Leu Asn Thr Asp Gln Lys Arg Glu Lys
            195                 200                 205

Glu His Leu Ala Gln Met Leu Thr Ile Ala Arg Asp Tyr Ala Arg Ala
210                 215                 220

Arg Gly Phe Lys Gly Thr Phe Leu Ile Glu Pro Lys Pro Met Glu Pro
225                 230                 235                 240

Thr Lys His Gln Tyr Asp Val Asp Thr Glu Thr Val Ile Gly Phe Leu
            245                 250                 255

Lys Ala His Gly Leu Asp Lys Asp Phe Lys Val Asn Ile Glu Val Asn
                260                 265                 270

His Ala Thr Leu Ala Gly His Thr Phe Glu His Glu Leu Ala Val Ala
            275                 280                 285

Val Asp Asn Gly Met Leu Gly Ser Ile Asp Ala Asn Arg Gly Asp Tyr
            290                 295                 300

Gln Asn Gly Trp Asp Thr Asp Gln Phe Pro Ile Asp Asn Tyr Glu Leu
305                 310                 315                 320

Thr Gln Ala Met Met Gln Ile Ile Arg Asn Gly Gly Leu Gly Thr Gly
                325                 330                 335

Gly Thr Asn Phe Asp Ala Lys Thr Arg Arg Asn Ser Thr Asp Leu Glu
            340                 345                 350

Asp Ile Phe Ile Ala His Ile Ala Gly Met Asp Ala Met Ala Arg Ala
                355                 360                 365

Leu Glu Ser Ala Ala Ala Leu Leu Asp Glu Ser Pro Tyr Lys Lys Met
            370                 375                 380

Leu Ala Asp Arg Tyr Ala Ser Phe Asp Gly Gly Lys Gly Lys Glu Phe
385                 390                 395                 400

Glu Asp Gly Lys Leu Thr Leu Glu Asp Val Val Ala Tyr Ala Lys Thr
                405                 410                 415
```

Lys Gly Glu Pro Lys Gln Thr Ser Gly Lys Gln Glu Leu Tyr Glu Ala
            420                 425                 430

Ile Leu Asn Met Tyr Cys
        435

<210> SEQ ID NO 26
<211> LENGTH: 1317
<212> TYPE: DNA
<213> ORGANISM: Bacteroides thetaiotaomicron

<400> SEQUENCE: 26

```
atggcaacaa aagaattttt tccgggaatt gaaaagatta aatttgaagg taaagatagt      60
aagaacccga tggcattccg ttattacgat gcagagaagg tgattaatgg taaaaagatg     120
aaggattggc tgagattcgc tatggcatgg tggcacacat tgtgcgctga aggtggtgat     180
cagttcggtg gcggaacaaa gcaattccca tggaatggta atgcagatgc tatacaggca     240
gcaaaagata agatggatgc aggatttgaa ttcatgcaga agatgggtat cgaatactat     300
tgcttccatg acgtagactt ggtttcgaag ggtgccagtg tagaagaata cgaagctaac     360
ctgaaagaaa tcgtagctta tgcaaaacag aaacaggcag aaaccggtat caaactactg     420
tggggtactg ctaatgtatt cggtcacgcc cgctatatga acggtgcagc taccaatcct     480
gacttcgatg tagtagctcg tgctgctgtt cagatcaaaa atgcgattga tgcaacgatt     540
gaacttggcg gagagaatta tgtgttttgg ggtggtcgtg aaggctatat gtctcttctg     600
aacacagatc agaaacgtga aaaagaacac cttgcacaga tgttgacgat tgctcgtgac     660
tatgcccgtg cccgtggttt caaaggtact ttcctgatcg aaccgaaacc gatggaaccg     720
actaaacatc aatatgacgt agatacggaa actgtaatcg gcttcctgaa agctcatggt     780
ctggataagg atttcaaagt aaatatcgag gtgaatcacg caactttggc aggtcacact     840
ttcgagcatg aattggctgt agctgtagac aatggtatgt tgggctcaat tgacgccaat     900
cgtggtgact atcagaatgg ctgggataca gaccaattcc cgatcgacaa ttatgaactg     960
actcaggcta tgatgcagat tatccgtaat ggtggtctcg gtaccggtgg tacgaacttt    1020
gatgctaaaa cccgtcgtaa ttctactgat ctggaagata tctttattgc tcacatcgca    1080
ggtatggacg ctatggcccg tgcactcgaa agtgcagcgg ctctgctcga cgaatctccc    1140
tataagaaga tgctggctga ccgttatgct tcatttgatg ggggcaaagg taaagaattt    1200
gaagacggca agctgactct ggaggatgtg gttgcttatg caaaaacaaa aggcgaaccg    1260
aaacagacta gcggcaagca agaactttat gaggcaattc tgaatatgta ttgctaa      1317
```

GENETICALLY MODIFIED STRAIN OF *S. CEREVISIAE* ENGINEERED TO FERMENT XYLOSE AND ARABINOSE

CROSS REFERENCE TO RELATED APPLICATIONS

This application is a continuation of U.S. application Ser. No. 14/356,510, filed May 6, 2014, which is a '371 of International Application No. PCT/US12/64457, filed Nov. 9, 2012, which claims the benefit of U.S. Provisional Application No. 61/557,971, filed Nov. 10, 2011, each of which are incorporated by reference herein.

REFERENCE TO SEQUENCE LISTING SUBMITTED ELECTRONICALLY VIA EFS-WEB

The content of the electronically submitted sequence listing (Name: 115235-246-SeqList.txt; Size: 98,895 bytes; Date of Creation: Feb. 16, 2017) is in accordance with 37 C.F.R. § 1.821-1.825, and is incorporated by reference in its entirety.

BACKGROUND OF THE INVENTION

Energy conversion, utilization and access underlie many of the great challenges of our time, including those associated with sustainability, environmental quality, security, and poverty. New applications of emerging technologies are required to respond to these challenges. Biotechnology, one of the most powerful of the emerging technologies, can give rise to important new energy conversion processes. Plant biomass and derivatives thereof are a resource for the biological conversion of energy to forms useful to humanity.

Among forms of plant biomass, lignocellulosic biomass ("biomass") is particularly well-suited for energy applications because of its large-scale availability, low cost, and environmentally benign production. In particular, many energy production and utilization cycles based on cellulosic biomass have near-zero greenhouse gas emissions on a life-cycle basis. The primary obstacle impeding the more widespread production of energy from biomass feedstocks is the general absence of low-cost technology for overcoming the recalcitrance of biomass materials to conversion into useful products. Lignocellulosic biomass contains carbohydrate fractions (e.g., cellulose and hemicellulose) including pentose sugars (e.g., xylose and arabinose) that can be converted into ethanol or other products such as lactic acid and acetic acid. In order to convert the lignocellulose fractions, the cellulose, hemicellulose, and pentoses must ultimately be converted into monosaccharides; it is this conversion step that has historically been problematic.

Biomass processing schemes involving enzymatic or microbial hydrolysis commonly involve four biologically mediated transformations: (1) the production of saccharolytic enzymes (cellulases and hemicellulases); (2) the hydrolysis of carbohydrate components present in pretreated biomass to sugars; (3) the fermentation of hexose sugars (e.g., glucose, mannose, and galactose); and (4) the fermentation of pentose sugars (e.g., xylose and arabinose). These four transformations occur in a single step in a process configuration called consolidated bioprocessing (CBP), which is distinguished from other less highly integrated configurations in that it does not involve a dedicated process step for cellulase and/or hemicellulase production.

CBP offers the potential for lower cost and higher efficiency than processes featuring dedicated cellulase production. The benefits result in part from avoided capital costs, substrate and other raw materials, and utilities associated with cellulase production. In addition, several factors support the realization of higher rates of hydrolysis, and hence reduced reactor volume and capital investment using CBP, including enzyme-microbe synergy and the use of thermophilic organisms and/or complexed cellulase systems. Moreover, cellulose-adherent cellulolytic microorganisms are likely to compete successfully for products of cellulose hydrolysis with non-adhered microbes, e.g., contaminants. Successful competition of desirable microbes increases the stability of industrial processes based on microbial cellulose utilization. Progress in developing CBP-enabling microorganisms is being made through two strategies: engineering naturally occurring cellulolytic microorganisms to improve product-related properties, such as yield and titer; and engineering non-cellulolytic organisms that exhibit high product yields and titers to express a heterologous cellulase and hemicellulase system enabling cellulose and hemicellulose utilization.

One way to meet the demand for ethanol production is to convert sugars found in biomass, i.e., materials such as agricultural wastes, corn hulls, corncobs, cellulosic materials, and the like to produce ethanol. Efficient biomass conversion in large-scale industrial applications requires a microorganism that is able to tolerate high concentrations of sugar and ethanol, and which is able to ferment more than one sugar simultaneously.

Pentoses appear in great abundance in nature. As much as 40% of a lignocellulosic material can be comprised of pentoses (Ladisch et al., "Process considerations in the enzymatic hydrolysis of biomass." *Enz. Microb. Technol.*, 5: 82-100. (1983)). By fermentation, pentoses can be converted to ethanol which can be used as a liquid fuel or a chemical feedstock. Although many microorganisms have the ability to ferment simple hexose sugars, the pentose sugars, xylose and arabinose, are among the most difficult sugars in biomass to metabolize. Some microorganisms can ferment pentoses to ethanol and other co-products, and microorganisms with improved ethanol production from pentose sugars have been genetically engineered. However, many of these studies have been conducted in bacteria that are sensitive to low pH and high concentrations of ethanol. Therefore, their use in fermentations is associated with undesired co-product formation, and the level of ethanol they are capable of producing remains low.

Bakers' yeast (*Saccharomyces cerevisiae*) is the preferred microorganism for the production of ethanol (Hahn-Hägerdal, B., et al., *Adv. Biochem. Eng. Biotechnol.* 73, 53-84 (2001)). Attributes in favor of this microbe are (i) high productivity at close to theoretical yields (0.51 g ethanol produced/g glucose used), (ii) high osmo- and ethanol tolerance, (iii) natural robustness in industrial processes, also (iv) being generally regarded as safe (GRAS) due to its long association with wine and bread making, and beer brewing. Furthermore, *S. cerevisiae* exhibits tolerance to inhibitors commonly found in hydrolysates resulting from biomass pretreatment. However, *S. cerevisiae* does not naturally break down components of cellulose, nor does it efficiently use pentose sugars.

Progress has been made in engineering *S. cerevisiae* to express heterologous enzymes that enable it to break down cellulose. (See e.g. U.S. application Ser. No. 13/130,549 and PCT/US2011/039192, incorporated herein by reference in their entirety). However, utilization of arabinose for industrial ethanologenic fermentation has not been demonstrated in yeast. In addition, there is a need for an ethanologenic organism capable of efficiently utilizing arabinose and xylose that is also capable of breaking down cellulose. The highest products yields are obtained when all the cellulose and hemicellulose are broken down into monomer sugars and fermented into the desired product.

Therefore, there is a need in the art for an ethanologenic organism capable of fermenting pentose sugars in quantities sufficient for commercial applicability. There is also a need to combine efficient pentose utilization with cellulose digestion in order to maximize the efficiency of cellulosic feedstock use and to generate the highest yield of product.

BRIEF SUMMARY OF THE INVENTION

The present invention provides a microorganism capable of fermenting arabinose to a desired product such as ethanol. In some embodiments, the organism is also capable of fermenting xylose. In some embodiments, the organism is capable of fermenting arabinose and xylose, and expresses one or more cellulases.

In some embodiments, the invention provides a recombinant eukaryotic host cell comprising a heterologous polynucleotide encoding an arabinose transporter (AraT), a heterologous polynucleotide encoding an arabinose isomerase (AI), a heterologous polynucleotide encoding a ribulokinase (RK) and a heterologous polynucleotide encoding a ribulose 5-phosphate epimerase (R5PE).

In some embodiments, the invention provides a recombinant eukaryotic host cell comprising a heterologous polynucleotide encoding an arabinose isomerase (AI), a heterologous polynucleotide encoding a ribulokinase (RK) and a heterologous polynucleotide encoding a ribulose 5-phosphate epimerase (R5PE), wherein one or more of the AI, RK and R5PE is derived from an AI, RK and R5PE of *B. thetaiotamicron*.

In some embodiments, the recombinant eukaryotic host contains an AraT derived from an AraT of an organism selected from the group consisting of *Ambrosiozyma monospora* (LAT2), *Candida arabinofermentans*, *Ambrosiozyma monospora* (LAT1), *Kluveromyces marxianus* (LAT1), *Pichia guillermondii* (LAT1), *Pichia guillermondii* (LAT2), *Pichia stipites*, *Ambrosiozyma monospora* (LAT2), *Debaryomyces hensenii*, *Apergillus flavus*, *Aspergillus tereus*, *Neosartorya fischeri*, *Aspergillus niger*, *Penicillium marneffei*, *Coccidioides posadasii*, *Gibberella zeae*, *Magnaporthe oryzae*, *Schizophyllum commune*, *Pichia stipites*, *Saccaharomyces* HXT2, *Aspergillus clavatus* (ACLA_032060), *Sclerotinia sclerotiorum* (SS1G_01302), *Arthroderma benhamiae* (ARB_03323), *Trichophyton equinum* (TEQG_03356), *Trichophyton tonsurans* (G_04876), *Coccidioides immitis* (CIMG 0.09387), *Coccidioides posadasii* (CPSG_03942), *Coccidioides posadasii* (CPC735_017640), *Botryotinia fuckeliana* (BC1G_08389), *Pyrenophora tritici-repentis* (PTRG_10527), *Ustilago maydis* (UM03895.1), *Clavispora lusitaniae* (CLUG_02297), *Pichia guillermondii* (LAT1), *Pichia guillermondii* (LAT2), *Debaryomyces hansenii* (DEHA2E01166g), *Pichia stipites*, *candida albicans*, *Debaryomyces hansenii* (DEHA2B16082g), *Kluveromyces marxianus* (LAT1), *Kluyveromyces lactis* (KLLA-ORF 10059), *Lachancea thermotolerans* (KLTH0H13728g), *Vanderwaltozyma polyspora* (Kpol_281p3), *Zygosaccharomyces rouxii* (ZYRO0E03916g), *Pichia pastoris* (0.1833), *Candida arabinofermentans* (0.1378), *Ambrosiozyma monospora* (LAT1), *Aspergillus clavatus* (ACLA_044740), *Neosartorya fischeri* (NFIA_094320), *Aspergillus flavus* (AFLA_116400), *Aspergillus terreus* (ATEG_08609), *Aspergillus niger* (ANI_1_1064034), *Telaromyces stipitatus* (TSTA_124770), *Penicillium chrysogenum* (Pc20g01790), *Penicillium chrysogenum* (Pc20g01790)#2, *Gibberella zeae* (FG10921.1), *Nectria hematococco*, and *Glomerella graminicola* (GLRG_10740).

In some embodiments, the recombinant eukaryotic host cell comprises an AraT that encodes an amino acid sequence at least 80% identical to any one of the amino acid sequences of SEQ ID NOs: 9-20. In some embodiments, the recombinant eukaryotic host comprises a heterologous AI, RK and R5PE wherein one or more of the AI, RK and R5PE is derived from an AI, RK and R5PE of *B. thetaiotamicron*.

In other embodiments, the invention comprises a recombinant eukaryotic host cell expressing an arabinose isomerase (AI), a ribulokinase (RK) and a ribulose-5-phosphate epimerase (R5PE) wherein the AI comprises an amino acid sequence at least 80% identical to the amino acid sequence of SEQ ID NO: 6; the RK comprises an amino acid sequence at least 80% identical to the amino acid sequence of SEQ ID NO: 7; and, the R5PE comprises an amino acid sequence at least 80% identical to the amino acid sequence of SEQ ID NO: 8. In further embodiments, the recombinant host cell of the invention further comprises a heterologous polynucleotide encoding a xylose isomerase (XI).

In some embodiments, expression of one or more heterologous polynucleotides confers an ability to ferment arabinose to the recombinant host cell. In some embodiments, the recombinant eukaryotic host cell further comprises a heterologous polynucleotide encoding a xylose isomerase (XI). In further embodiments, the XI is derived from an XI of *B. thetaiotamicron*. In some embodiments, the XI comprises an amino acid sequence at least 80% identical to the amino acid sequence of SEQ ID NO: 24 or SEQ ID NO: 26.

In some embodiments, the host cell is a yeast cell selected from the group consisting of *Saccharomyces cerevisiae*, *Schizzosaccharomyces pombe*, *Candida albicans*. *Pichia pastoris*, *Pichia stipitis*, *Yarrowia lipolytica*, *Hansenula polymorpha*, *Phaffia rhodozyma*, *Candida utilis*, *Arxula adeninivorans*, *Debaryomyces hansenii*, *Debaryomyces polymorphus*, *Schizosaccharomyces pombe* and *Schwanniomyces occidentalis*.

In some embodiments, the yeast cell comprises a heterologous sequence encoding a xylulokinase, ribulose 5-phosphate isomerase, ribulose 5-phophate epimerase, transketolase and transaldolase, and the yeast cell does not express an aldose reductase that is capable of catalyzing the conversion of xylose to xylitol.

In some embodiments, the invention relates to a method of producing a fermentation product comprising:

a) combining a recombinant eukaryotic host cell of the invention with a substrate;

b) allowing the host cell to ferment the substrate; and, c) recovering one or more products of the fermentation, wherein the substrate is selected from the group consisting of cellulosic substrate, biomass feedstock, and combinations thereof.

In some embodiments, the invention relates to a composition comprising a carbon source and the recombinant eukaryotic host cell.

In some embodiments, the invention relates to a media supernatant generated by incubating the host cell with a medium containing a carbon source.

BRIEF DESCRIPTION OF THE DRAWINGS/FIGURES

Figure 3:
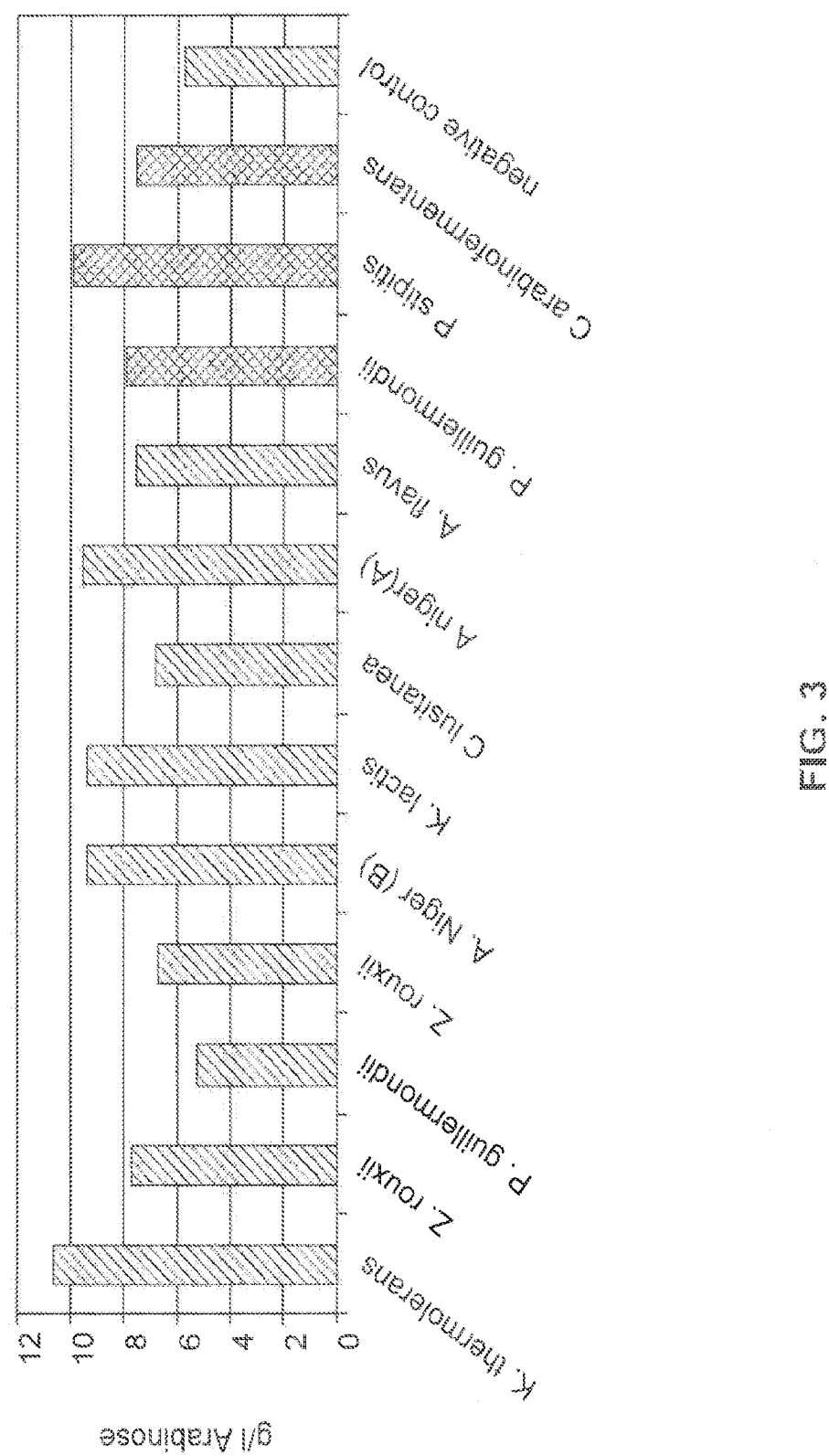

FIG. 3 depicts the results from an arabinose uptake assay. S. cerevisiae strains were transformed with a plasmid expressing an arabinose transporter derived from the species indicated. The negative control strain was transformed with an empty vector plasmid. Arabinose concentration was measured before inoculation and 48 hours after inoculation.

Figure 4:
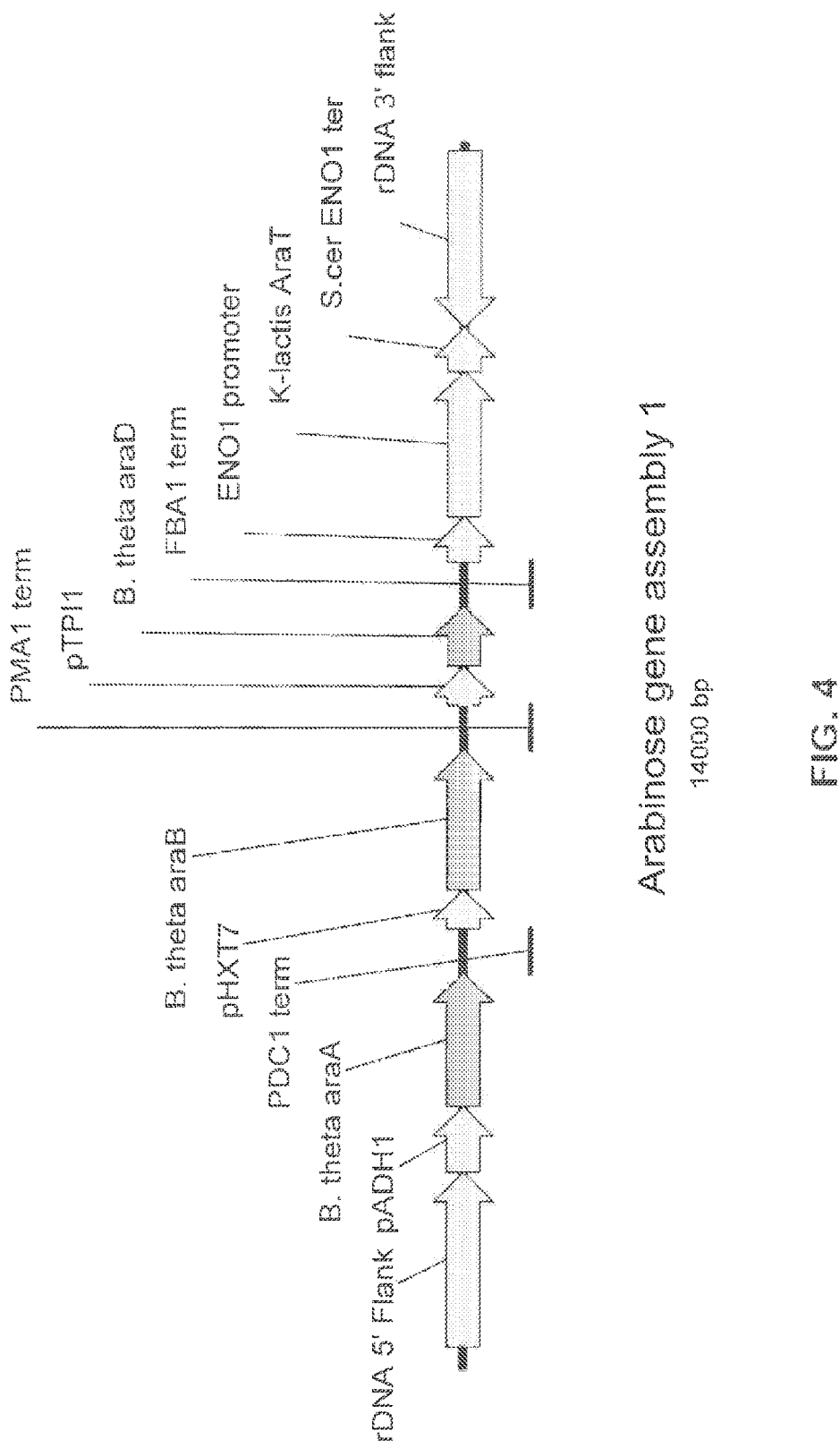

FIG. 4 depicts an assembly of the DNA construct used to compile the components of the arabinose utilization pathway and target the assembly to the rDNA sites for recombination into the yeast genome, (i.e. an arabinose transporter (AraT), an arabinose isomerase (AI), a ribulokinase (RK) and a ribulose 5-phosphate epimerase (R5PE), collectively the arabinose-utilization construct).

Figure 5:
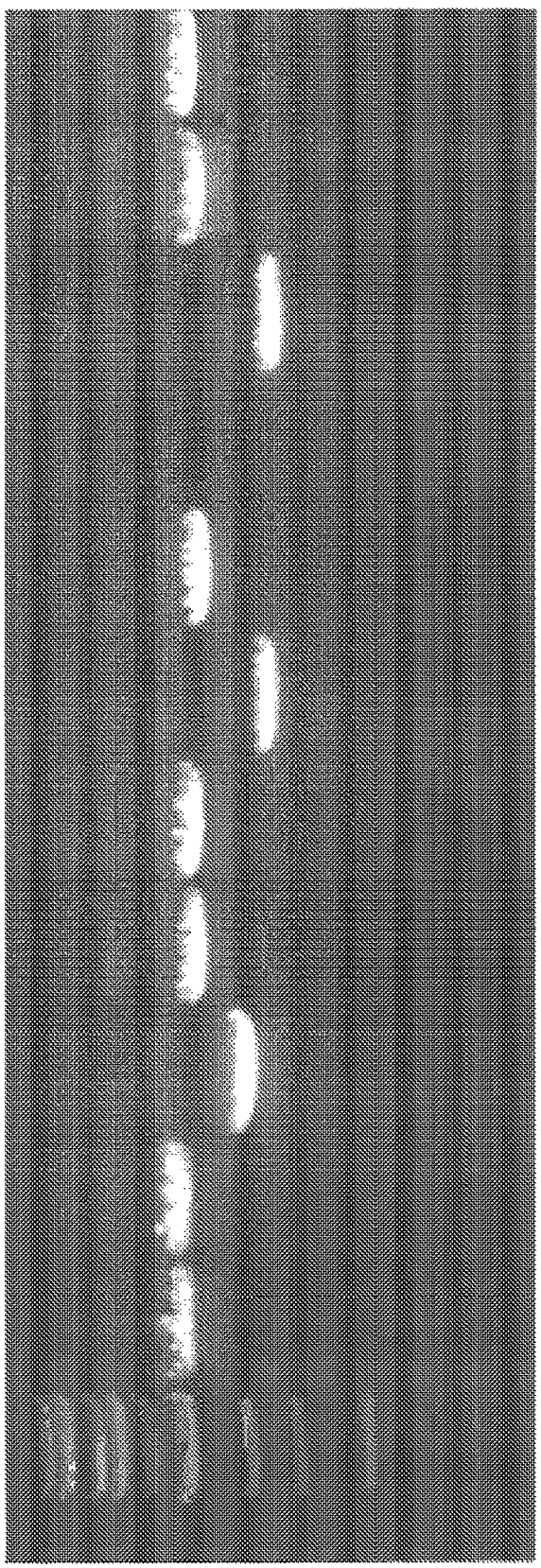

FIG. 5 depicts an electrophoretic gel image depicting the individual amplicons that were cotransformed into yeast to assemble into the arabinose-utilization construct depicted in FIG. 4, and integrate into the yeast genome.

Figure 6:
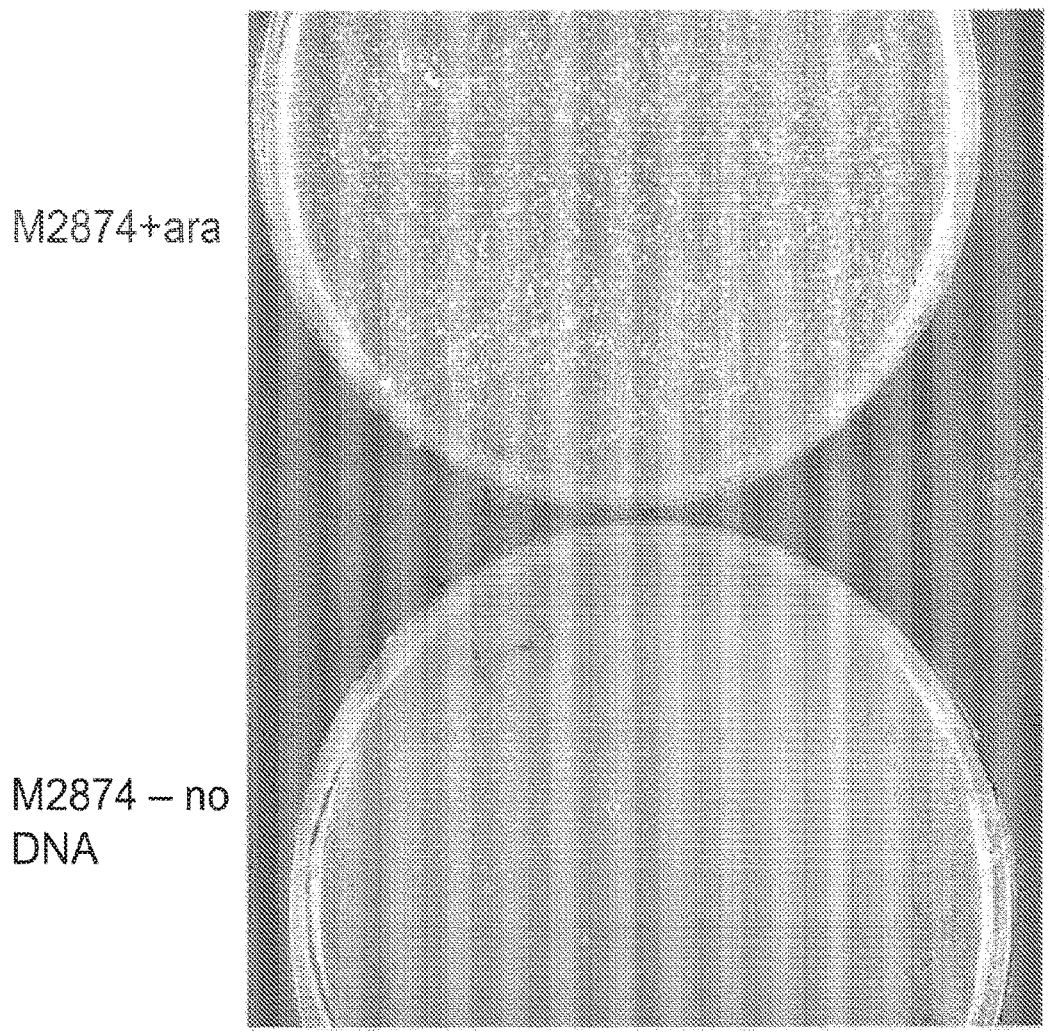

FIG. 6 depicts the results of a yeast transformation either with the DNA components of the arabinose-utilization construct added to the transformation or with no DNA added to the transformation. Transformants were selected on media containing arabinose as the only sugar. Colonies grew only upon successful transformation and integration of the arabinose-utilization construct into the genome of a progenitor cell.

Figure 7:
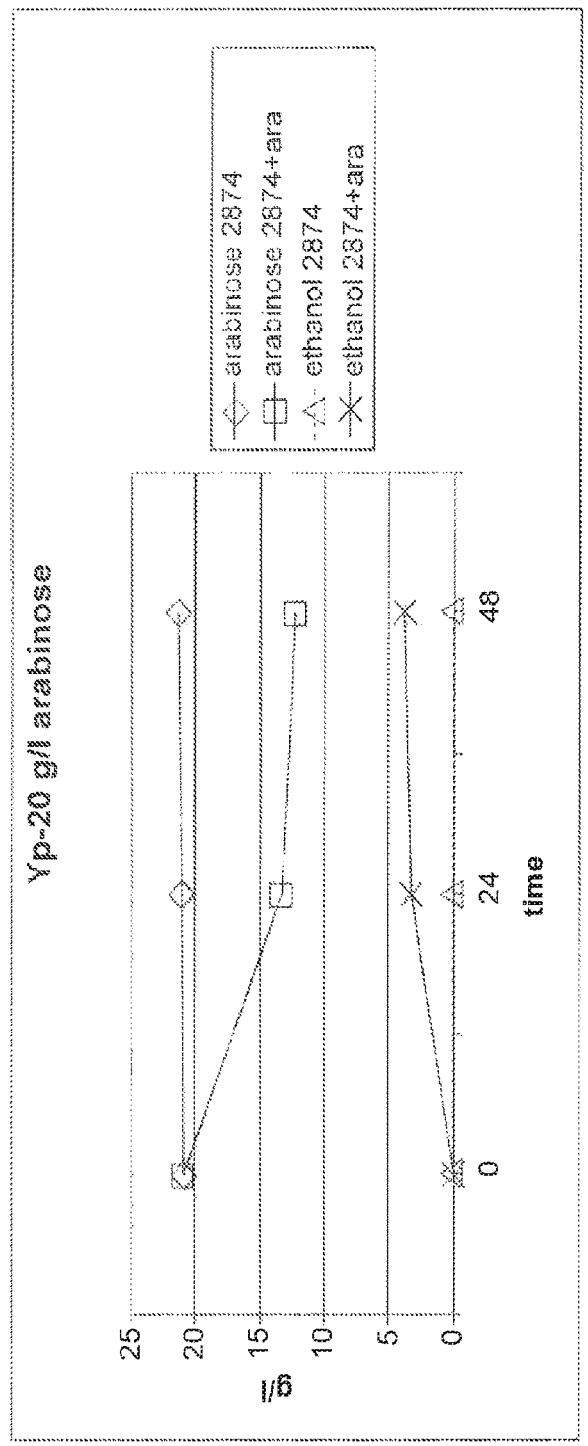

FIG. 7 depicts the levels of arabinose and ethanol over time in a fermentation experiment using an S. cerevisiae strain containing the arabinose-utilization construct (2874+ara) versus the control strain (2874). The control strain uses no arabinose and produces no ethanol whereas the strain containing the arabinose-utilization construct uses arabinose and is able to ferment arabinose to ethanol.

Figure 8:
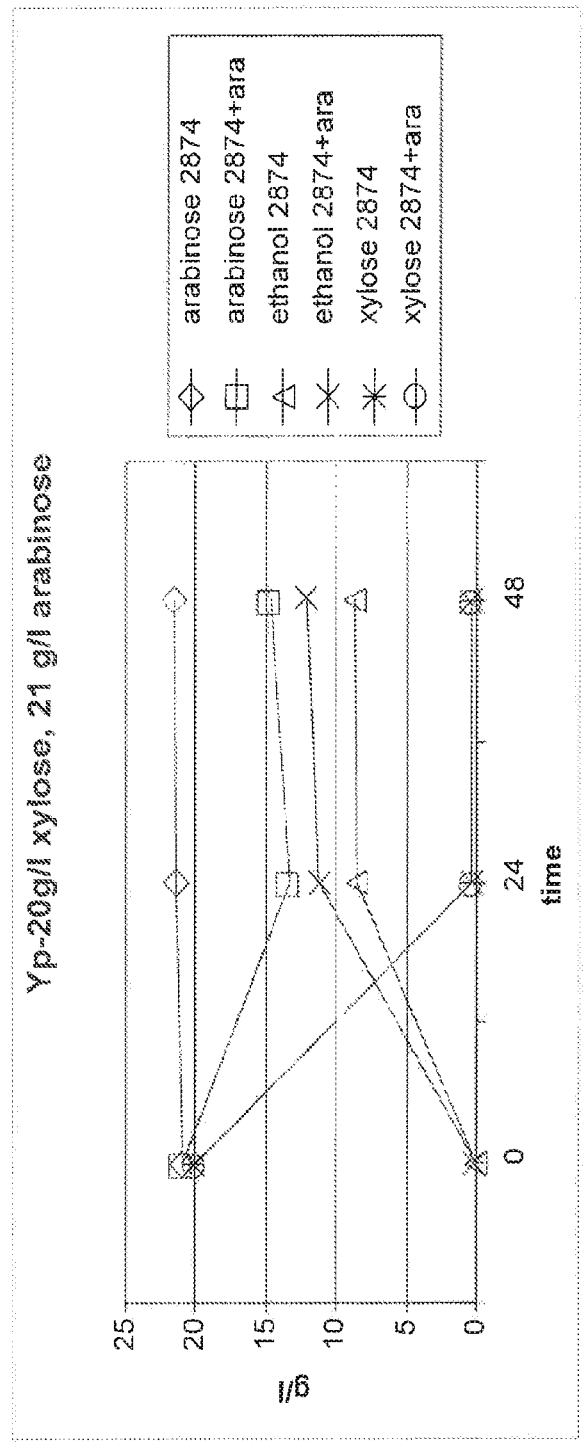

FIG. 8 depicts the levels of arabinose, xylose and ethanol over time in a fermentation experiment using an S. cerevisiae strain containing the arabinose-utilization construct (2874+ara) versus a control strain (2874). The control strain uses no arabinose, but can produce ethanol from the xylose present in the media. The strain containing the arabinose-utilization construct (2874-ara) is able to ferment arabinose to ethanol which accounts for the increased ethanol produced as compared to the control strain.

Figure 9:
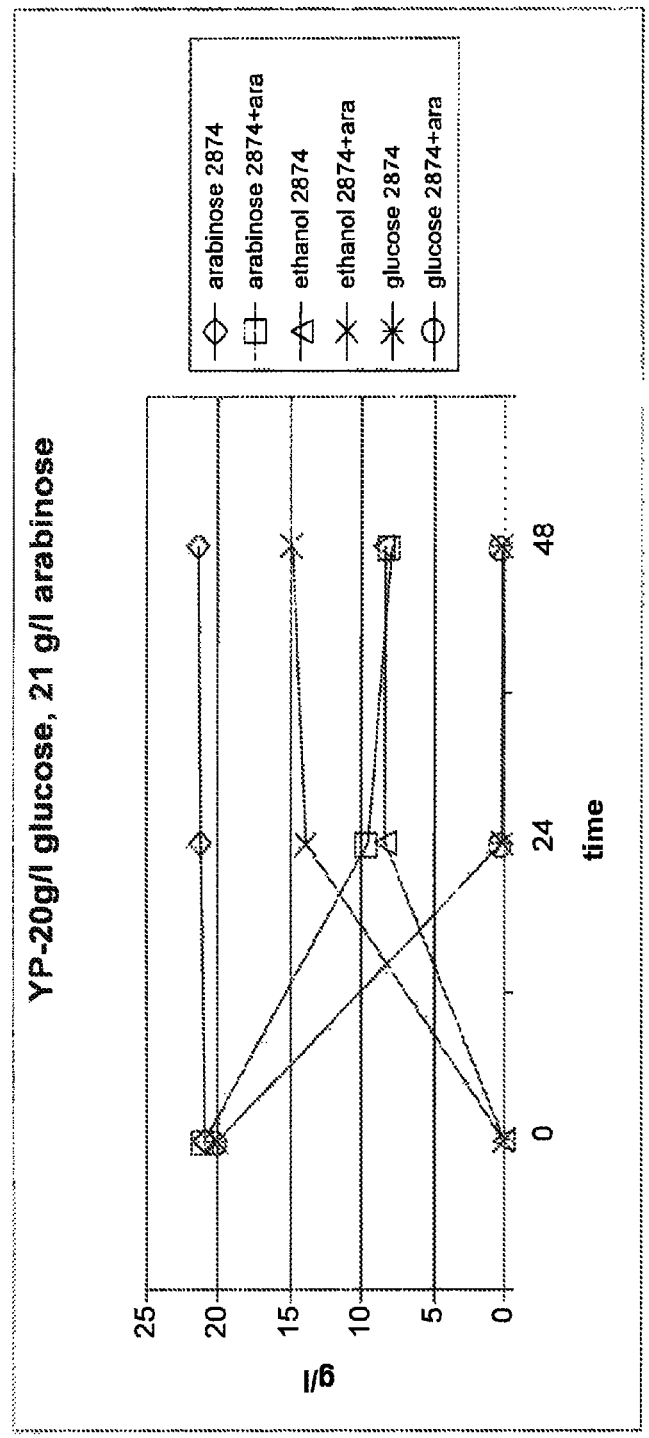

FIG. 9 depicts the levels of arabinose, glucose and ethanol over time in a fermentation experiment using an S. cerevisiae strain containing the arabinose-utilization construct (2874+ara) versus a control strain (2874). The control strain uses no arabinose, but can produce ethanol from the glucose present in the media. The strain containing the arabinose-utilization construct (2874+ara) is able to ferment arabinose to ethanol which accounts for the increased ethanol produced as compared to the control strain.

Figure 10:
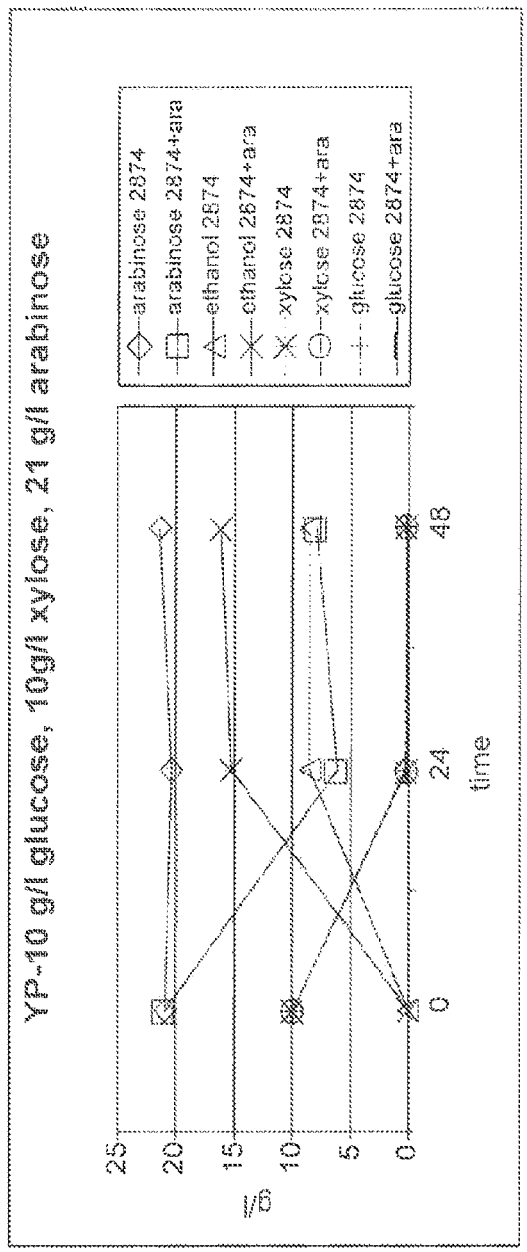

FIG. 10 depicts levels of arabinose, xylose, glucose and ethanol over time in a fermentation experiment using an S. cerevisiae strain containing the arabinose-utilization construct (2874+ara) versus a control strain (2874). The control strain uses no arabinose, but can produce ethanol from the glucose and xylose present in the media. The strain containing the arabinose-utilization construct (2874+ara) is able to ferment arabinose to ethanol which accounts for the increased ethanol produced as compared to the control strain.

Figure 11:
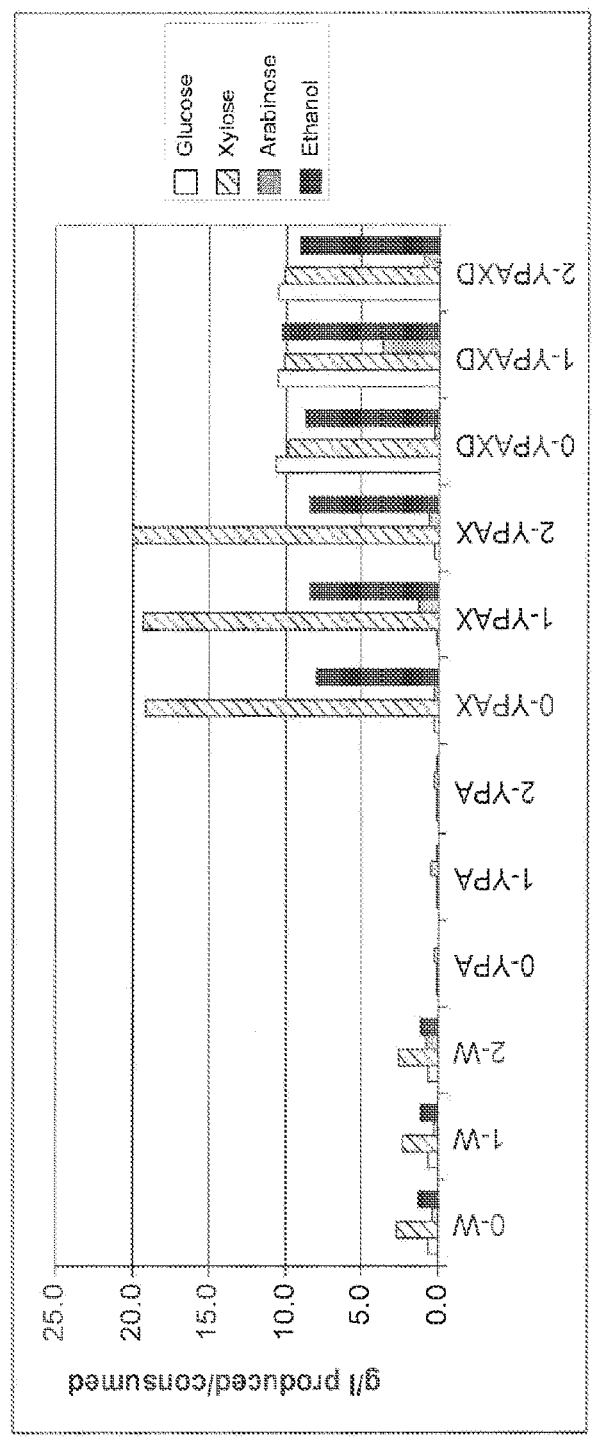
Figure 12:
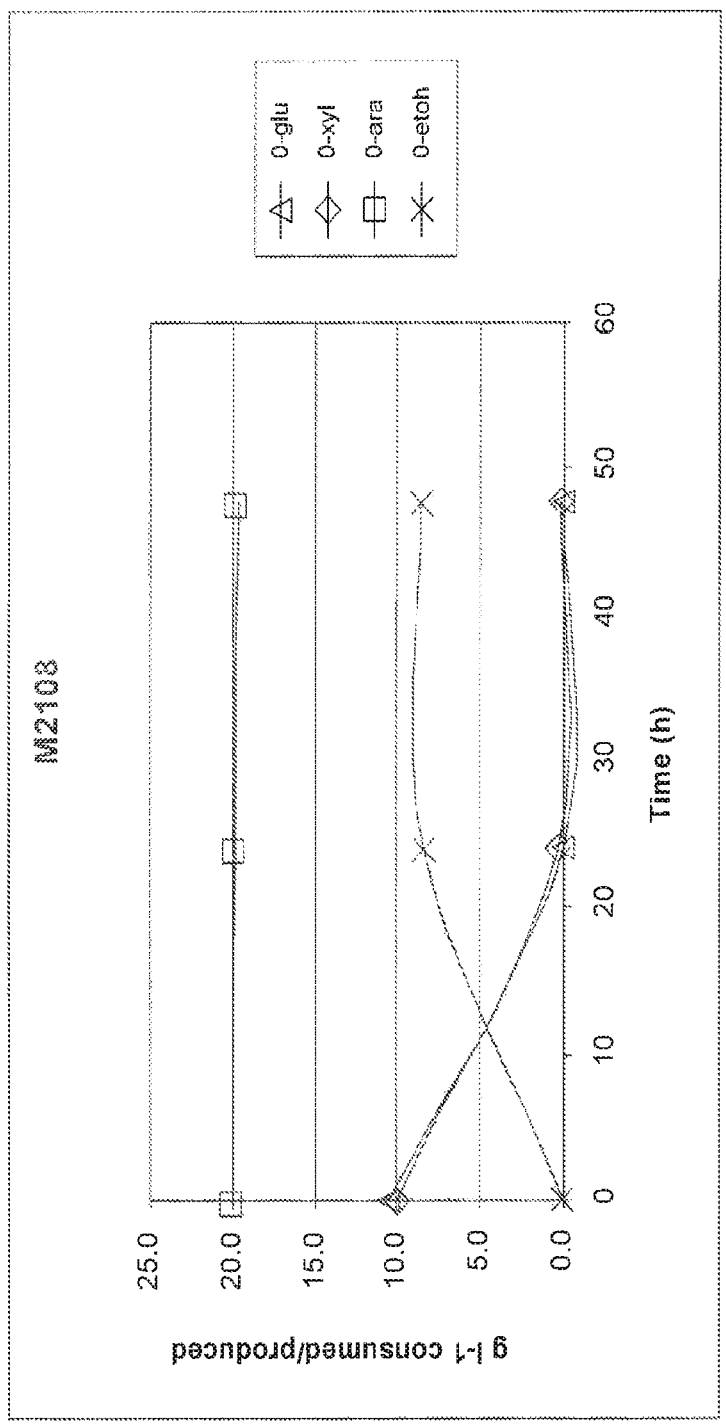
Figure 13:
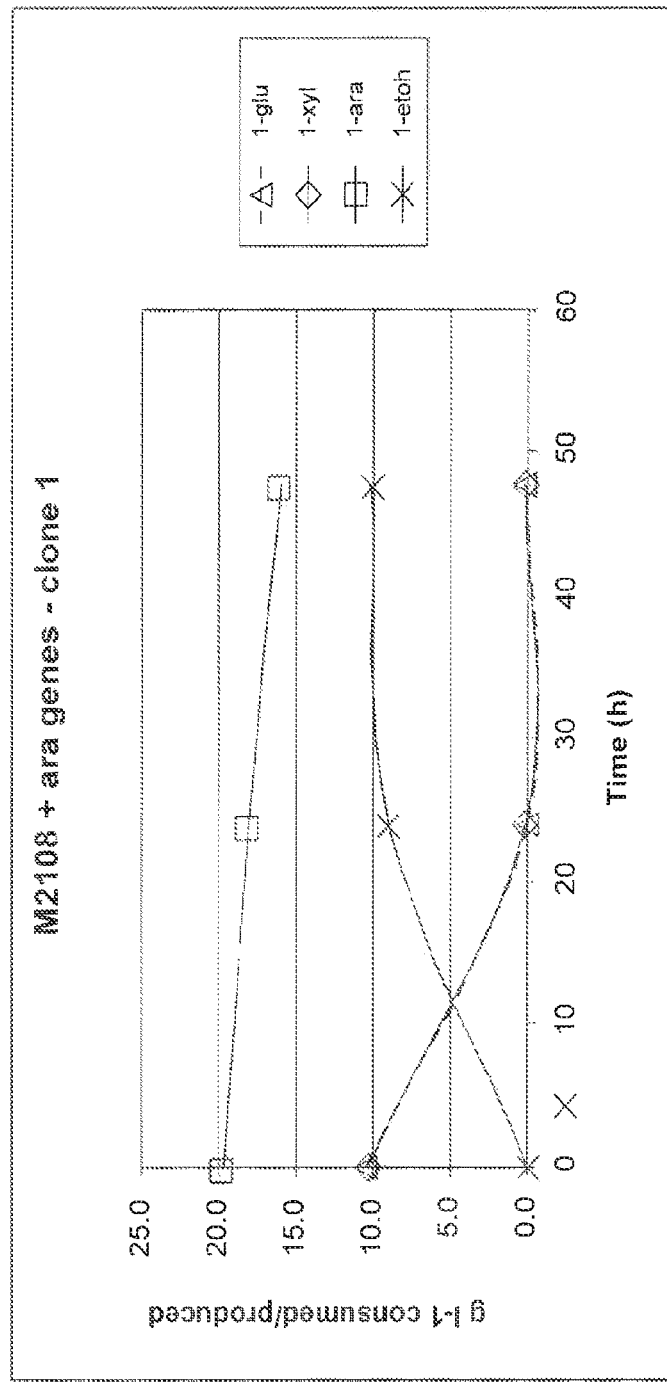

FIGS. 11-13 depict results from an arabinose utilization assay in an S. cerevisiae strain expressing the arabinose utilization genes of the invention and also expressing a xylose isomerase from Pyromyces spp. The yeast strains were pregrown on YPX, washed, and used to inoculate 150 ml sealed bottles with 25 ml medium, which were flushed with $N_2$ and incubated at 35° C. at 250 RPM. Cultures were sampled for HPLC at 0, 24, and 48 hours. No growth was observed on YPA. 3.7 g $l^{-1}$ arabinose was consumed for clone 1 in YPAXD. Over half of this (2.1 g $l^{-1}$) was consumed between 24 and 48 h, when xylose and glucose already had been depleted. Legend: 0 (parental strain), 1 (parental strain+ara genes, clone 1), 2 (parental strain+ara genes, clone 2).

DETAILED DESCRIPTION OF THE INVENTION

This specification discloses one or more embodiments that incorporate the features of this invention. The disclosed embodiment(s) merely exemplify the invention. The scope of the invention is not limited to the disclosed embodiment(s). The invention is defined by the claims appended hereto.

In the following description, for purposes of explanation, specific numbers, materials and configurations are set forth in order to provide a thorough understanding of the invention. It will be apparent, however, to one having ordinary skill in the art that the invention may be practiced without these specific details. In some instances, well-known features may be omitted or simplified so as not to obscure the present invention.

The embodiment(s) described, and references in the specification to "one embodiment", "an embodiment", "an example embodiment", etc., indicate that the embodiment(s) described can include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to affect such feature, structure, or characteristic in connection with other embodiments whether or not explicitly described.

The description of "a" or "an" item herein may refer to a single item or multiple items. It is understood that wherever embodiments are described herein with the language "comprising," otherwise analogous embodiments described in terms of "consisting of" and/or "consisting essentially of" are also provided.

Definitions

The term "heterologous" when used in reference to a polynucleotide, a gene, a polypeptide, or an enzyme refers to a polynucleotide, gene, polypeptide, or an enzyme not normally found in the host organism. "Heterologous" also includes a native coding region, or portion thereof, that is reintroduced into the source organism in a form that is different from the corresponding native gene, e.g., not in its natural location in the organism's genome or with different regulatory sequences. The heterologous polynucleotide or gene may be introduced into the host organism by, e.g., gene transfer. A heterologous gene may include a native coding region that is a portion of a chimeric gene including non-native regulatory regions that is reintroduced into the native host. Foreign genes can comprise native genes inserted into a non-native organism, or chimeric genes. A heterologous polynucleotide, gene, polypeptide, or an enzyme may be derived from any source, e.g., eukaryotes, prokaryotes, viruses, or synthetic polynucleotide fragments.

The term "promoter" as used herein is a region of DNA that facilitates the transcription of a particular gene. Promoters are typically located near the genes they regulate, on the same strand and upstream (towards the 5' region of the sense strand). The terms "promoter" or "surrogate promoter" is intended to include a polynucleotide that can transcriptionally control a gene-of-interest that it does not transcriptionally control in nature. In certain embodiments, the transcriptional control of a surrogate promoter results in an increase in expression of the gene-of-interest. In certain embodiments, a surrogate promoter is placed 5' to the gene-of-interest. A surrogate promoter may be used to replace the natural promoter, or may be used in addition to the natural promoter. A surrogate promoter may be endogenous with regard to the host cell in which it is used, or it may be a heterologous polynucleotide sequence introduced into the host cell, e.g., exogenous with regard to the host cell in which it is used.

As used herein, the term "terminator" or "transcription terminator" is a section of genetic sequence that marks the end of a gene or operon on genomic DNA for transcription. Promoters and terminators suitable for use in the present invention include, for example, those found in Table 1.

TABLE 1

Sequences of promoters and terminators used in exemplary embodiments.

| Promoter | Sequence |
|---|---|
| ADH1 promoter | cgattttttttctaaaccgtggaatatttcggatatccttttgttgtttccgggtgtacaatat<br>ggacttcctcttttctggcaaccaaaccatacatcgggattcctataatccttcgttg<br>gtctccctaacatgtaggtggcggaggggagatatacaatagaacagataccagac<br>aagacataatgggctaaacaagactacaccaattacactgcctcattgatggtggta<br>cataacgaactaatactgtagccctagacttgatagccatcatcatatcgaagtttcac<br>taccctttttccatttgccatctattgaagtaataataggcgcatgcaacttcttttcttttt<br>tttcttttctctctccccgttgttgtctcaccatatccgcaatgacaaaaaaatgatgga<br>agacactaaaggaaaaaattaacgacaaagacagcaccaacagatgtcgttgttcc<br>agagctgatgagggggtatctcgaagcacacgaaacttttccttccttcattcacgca<br>cactactctctaatgagcaacggtatacggccttccttccagttacttgaatttgaaata<br>aaaaaaagtttgctgtcttgctatcaagtataaatagacctgcaattattaatcttttgttt<br>cctcgtcattgttctcgttccctttcttccttgtttcttttttctgcacaatatttcaagctatac<br>caagcatacaatcaactatctcatataca |
| HXT7 promoter | ccagaaaggcaacgcaaaatttttttttccagggaataaactttttatgacccactacttc<br>tcgtaggaacaatttcgggccctgcgtgttcttctgaggttcatctttttacatttgcttct<br>gctggataattttcagaggcaacaaggaaaaattagatggcaaaaagtcgtctttca<br>aggaaaaatccccaccatctttcgagatcccctgtaacttattggcaactgaaagaat<br>gaaaaggaggaaaatacaaatatactagaactgaaaaaaaaaagtataaataga<br>gacgatatatgccaatacttcacaatgttcgaatctattcttcatttgcagctattgtaaa<br>ataataaaacatcaagaacaaacaagctcaacttgtcttttctaagaacaaagaataa<br>acacaaaaacaaaaagtttttttttaatttttaatcaaaaa |
| TPI1 promoter | ctacttattcccttcgagattatatctaggaacccatcaggttggtggaagattacccg<br>ttctaagacttttcagcttcctctattgatgttacacctggacacccctttctggcatcc<br>agttttaatcttcagtggcatgtgagattctccgaaattaattaaagcaatcacacaatt<br>ctctcggataccacctcggttgaaactgacaggtggtttgttacgcatgctaatgcaa<br>aggagcctatataccttggctcggctgctgtaacagggaatataaagggcagcata<br>atttaggagtttagtgaacttgcaacatttactattttcccttcttacgtaaatattttcttt<br>taattctaaatcaatcttttcaattttttgtttgtattcttttcttgcttaaatc-<br>tataactacaa<br>aaaacacatacataaactaaaa |
| ENO1 promoter | ctagtcttctaggcgggttatctactgatccgagcttccactaggatagcacccaaac<br>acctgcatatttggacgacctttacttacaccaccaaaaaccactttcgcctctcccgc<br>ccctgataacgtccactaattgagcgattacctgagcggtcctcttttgtttgcagcat<br>gagacttgcatactgcaaatcgtaagtagcaacgtctcaaggtcaaaactgtatgga<br>aaccttgtcacctcacttaatctagctagcaatacccctgcaagtcaagaggtctccgtg<br>attcctagccacctcaaggtatgcctctccccggaaactgtggccttttctggcacac<br>atgatctccacgatttcaacatataaatagcttttgataatggcaatattaatcaaatttat<br>tttacttctttcttgtaacatctctcttgtaatcccttattccttctagctatttttcataaaaa<br>accaagcaactgcttatcaacacacaaacactaaatcaaa |
| PDC1 terminator | gcgatttaatctctaattattagttaaagttttataagcatttttatgtaacgaaaaataaat<br>tggttcatattattactgcactgtcacttaccatggaaagaccagacaagaagttgcc<br>gacagtctgttgaattggcctggttaggcttaagtctgggtccgcttcttttacaaatttg<br>gagaatttctcttaaacgatatgtatattcttttcgttggaaaagatgtcttccaaaaaaa<br>aaaccgatgaattagtggaaccaaggaaaaaaaaagaggtatccttgattaaggaa<br>cactgtttaaacagtgtggtttccaaaaccctgaaactgcattagtgtaatagaagact<br>agacacctcgatacaaataatggttactcaattcaaaactgccagcgaattcgactct<br>gcaattgctcaagacaagctagttgtcgtagatttctacgccacttggtgcggtccat<br>gtaaaatgattgctccaatgattgaaa |
| PMA1 terminator | tcctgttgaagtagcatttaatcataattttttgtcacatttttaatcaacttgattttttctggttt<br>aattttttctaatttttaattttaattttttttatcaatgggaactgatacactaaaaagaattag<br>gagccaacaagaataagccgcttatttcctactagagtttgcttaaaatttcatctcga |

TABLE 1 -continued

Sequences of promoters and terminators used in exemplary embodiments.

| Promoter | Sequence |
|---|---|
| | attgtcattctaatattttatccacacacacaccttaaaattttagattaaatggcatcaa<br>ctcttagcttcacacacacacacacaccgaagctggttgttttatttgatttgatataatt<br>ggtttctctggatggtacttttctttcttggttatttcctattttaaaatatgaaacgcaca<br>caagtcataattattctaatagagcacaattcacaacacgcacatttcaactttaatattt<br>ttttagaaacactttatttagtctaattcttaattttaatatatataatgcacacacactaat<br>tt |
| FBA1 terminator | gttaattcaaattaattgatatagtttttaatgagtattgaatctgtttagaaataatggaa<br>tattattttattattttatttatattattggtcggctcttttcttctgaaggtcaatgacaaaat<br>gatatgaaggaaataatgatttctaaaattttacaacgtaagatatttttacaaaagcct<br>agctcatcttttgtcatgcactattttactcacgcttgaaattaacggccagtccactgc<br>ggagtcatttcaaagtcatcctaatcgatctatcgtttttgatagctcattttggagttcg<br>cgattgtcttctgttattcacaactgttttaatttttatttcattctggaactcttcgagttctt<br>gtaaagtctttcatagtagcttacttatcctccaacatatttaacttcatgtcaatttcgg<br>ctcttaaattttccacatcatcaagttcaacatcatcttttaacttgaatttattctctagc |
| ENO1 terminator | tcgagagcttttgattaagccttctaaccaaaaaacacgttttttgtcatttatttcatttt<br>cttagaatagtttagtttattcattttatagtcacgaatgttttatgattctatataaggttgc<br>aaacaagcatattcatatatgttaaaacaatttcaggtttaccttttattagcttgtggtg<br>acgcgtgtatccgcccgctcttttggtcacccatgtatttaattgcataaataattcttaa<br>aagtggagctagtctatttctatttacatacctctcatttctcatttcctcctaatgtgtcaa<br>tgatcatattcttaactggaccgatcttattcgtcagattcaaaccaaaagttcttaggg<br>ctaccacaggaggaaaattagtgtgatataatttaaataatttatccgccattcctaata<br>gaacgttgttcgacggatatctttctgcccaaaagggttctaagctcaatgaagagcc<br>aatgtctaaacctc |

As used herein, the term "operon" refers to a functioning unit of genomic material containing a cluster of genes under the control of a single regulatory signal or promoter. The genes are transcribed together into an mRNA strand and either translated together in the cytoplasm, or undergo trans-splicing to create monocistronic mRNAs that are translated separately, i.e. several strands of mRNA that each encode a single gene product. The result of this is that the genes contained in the operon are either expressed together or not at all. Originally operons were thought to exist solely in prokaryotes but since the discovery of the first operons in eukaryotes in the early 1990s, more evidence has arisen to suggest they are more common than previously assumed. Operons occur primarily in prokaryotes but also in some eukaryotes, including *Drosophila melanogaster* and *C. elegans*.

The terms "gene(s)" or "polynucleotide" or "polynucleotide sequence(s)" are intended to include nucleic acid molecules, e.g., polynucleotides which include an open reading frame encoding a polypeptide, and can further include non-coding regulatory sequences, and introns. In addition, the terms are intended to include one or more genes that map to a functional locus. In addition, the terms are intended to include a specific gene for a selected purpose. The gene may be endogenous to the host cell or may be recombinantly introduced into the host cell, e.g., as a plasmid maintained episomally or a plasmid (or fragment thereof) that is stably integrated into the genome. In addition to the plasmid form, a gene may, for example, be in the form of linear DNA. As used herein, the terms may refer to, inter alia, genes encoding enzymes in the D-xylose pathway, such as xylose isomerase and xylulokinase and enzymes in the L-arabinose pathway, such as arabinose transporters (AraT), arabinose isomerase (AI), ribulokinase (RK), and ribulose 5-phosphate epimerase (R5PE). The term gene is also intended to cover all copies of a particular gene, e.g., all of the DNA sequences in a cell encoding a particular gene product.

The term "expression" is intended to include the expression of a gene at least at the level of mRNA production.

The term "expression product" is intended to include the resultant product, e.g., a polypeptide, of an expressed gene.

The term "cellulolytic activity" is intended to include the ability to hydrolyze glycosidic linkages in oligohexoses and polyhexoses. Cellulolytic activity may also include the ability to depolymerize or debranch cellulose and hemicellulose.

A "xylose metabolizing enzyme" can be any enzyme involved in xylose digestion, metabolism and/or hydrolysis, including a xylose isomerase, xylulokinase, xylose reductase, xylose dehydrogenase, xylitol dehydrogenase, xylonate dehydratase, a transketolase, and a transaldolase protein.

A "xylulokinase" (XK) as used herein, is meant for refer to an enzyme that catalyzes the chemical reaction: ATP+D-xylulose⇌ADP+D-xylulose 5-phosphate. Thus, the two substrates of this enzyme are ATP and D-xylulose, whereas its two products are ADP and D-xylulose 5-phosphate. This enzyme belongs to the family of transferases, specifically those transferring phosphorus-containing groups (phosphotransferases) with an alcohol group as acceptor. The systematic name of this enzyme class is ATP:D-xylulose 5-phosphotransferase. Other names in common use include xylulokinase (phosphorylating), and D-xylulokinase. This enzyme participates in pentose and glucuronate interconversions. XK includes those enzymes that correspond to Enzyme Commission Number 2.7.1.17.

A "xylose isomerase" (XI) as used herein, is meant to refer to an enzyme that catalyzes the chemical reaction: D-xylose ⇌ D-xylulose. This enzyme belongs to the family of isomerases, specifically those intramolecular oxidoreductases interconverting aldoses and ketoses. The systematic name of this enzyme class is D-xylose aldose-ketose-isomerase. Other names in common use include D-xylose isomerase, D-xylose ketoisomerase, and D-xylose ketol-isomerase. This enzyme participates in pentose and glucuronate interconversions and fructose and mannose metabolism. The enzyme is used industrially to convert glucose to fructose in the manufacture of high-fructose corn syrup. It is sometimes referred to as "glucose isomerase". XI includes those enzymes that correspond to Enzyme Commission Number 5.3.1.5.

An "arabinose transporter" as used herein is meant to refer to an enzyme that is capable of efficiently transporting arabinose across a membrane. In general, arabinose transporters are transmembrane proteins that selectively transport pentoses, specifically arabinose, into the cell. Arabinose transporters according to the invention can be derived from a number of species. These include, e.g., transporters derived from *Ambrosiozyma monospora, Candida arabinofermentans, Ambrosiozyma monospora, Kluveromyces marxianus, Pichia guillermondii* (LAT1), *Pichia guillermondii* (LAT2), *Pichia stipites, Ambrosiozyma monospora* (LAT2), *Debaryomyces hensenii, Aspergillus flavus, Aspergillus terreus. Neosartorya fischeri, Aspergillus niger, Penicillium marneffei, Coccidioides posadasii, Gibberella zeae, Magnaporthe oryzae, Schizophyllum commune, Pichia stipites, Saccharomyces* HXT2, *Aspergillus clavatus* (ACLA_032060), *Sclerotinia sclerotiorum* (SS1G_01302), *Arthroderma benhamiae* (ARB_03323), *Trichophyton equinum* (TEQG_03356), *Trichophyton tonsurans* (G_04876), *Coccidioides immitis* (CIMG_09387), *Coccidioides posadasii* (CPSG_03942), *Coccidioides posadasii* (CPC735_017640), *Botryotinia fuckeliana* (BC1G_08389), *Pyrenophora tritici-repentis* (PTRG_10527), *Ustilago maydis* (UM03895.1), *Clavispora lusitaniae* (CLUG_02297), *Pichia guillermondii* (LAT1), *Pichia guillermondii* (LAT2), *Debaryomyces hansenii* (DEHA2E01166g), *Pichia stipites, candida albicans, Debaryomyces hansenii* (DEHA2B16082g), *Kluveromyces marxianus* (LAT1), *Kluyveromyces lactis* (KLLA-ORF 10059), *Lachancea thermotolerans* (KLTH0H13728g), *Vanderwaltozyma polyspora* (Kpol_281p3), *Zygosaccharomyces rouxii* (ZYRO0E03916g), *Pichia pastoris* (0.1833), *Candida arabinofermentans* (0.1378), *Ambrosiozyma monospora* (LAT1), *Aspergillus clavatus* (ACLA_044740), *Neosartorya fischeri* (NFIA_094320), *Aspergillus flavus* (AFLA_116400), *Aspergillus terreus* (ATEG_08609), *Aspergillus niger* (ANI_1_1064034), *Telaromyces stipitatus* (TSTA_0.124770), *Penicillium chrysogenum* (Pc20g01790), *Penicillium chrysogenum* (Pc20g01790)#2, *Gibberella zeae* (FG10921.1), *Nectria hematococco*, and *Glomerella graminicola* (GLRG_10740) and *Arabidopsis thaliana* or any suitable source of the enzyme.

As used herein, "taken up" or "take up" is used to refer to the ability of a cell to transport a chemical moiety from the extracellular space into the intracellular space. For example, arabinose transporters of the invention allow the host cells of the invention to "take up" arabinose from the extracellular medium into the host cell.

An "arabinose isomerase (AI)" as used herein is meant to refer to an enzyme that is capable of catalyzing the chemical conversion of arabinose to ribulose (EC 5.3.1.3). Arabinose isomerase belongs to the oxidoreductase family of enzymes capable of interconverting aldoses and ketoses. Arabinose isomerases of the invention include those derived from various species including both prokaryotic and eukaryotic species. Arabinose isomerases may be derived from *B. subtilis, M. smegmatis, B. licheniformis, L. plantarum, Arthrobacter aurescens, Clavibacter michiganensis, Gramella forsetii. B. thetaiotamicron* or any other suitable source of the enzyme.

A "ribulokinase" (RK) as used herein is meant to refer to an enzyme that is capable of catalyzing the chemical reaction that phosphorylates ribulose to yield ribulose-5-phosphate (EC 2.7.1.16). Ribulokinases of the invention include those derived from various species including both prokaryotic and eukaryotic species. Ribulokinases may be derived from *E. coli, L. plantarum, A. aurescens, C. michiganensis, G. forsetii, B. thetaiotamicron* or any other suitable source of the enzyme.

A "ribulose 5-phosphate epimerase" (R5PE) as used herein is meant to refer to an enzyme that is capable of catalyzing the interconversion of ribulose-5-phosphate and xylulose-5-phosphate (EC 5.1.3.4). Ribulose 5-phosphate epimerases of the invention include those derived from various species including both prokaryotic and eukaryotic species. Ribulose 5-phosphate epimerases of the present invention include those derived from various species including both prokaryotic and eukaryotic species. Ribulose 5-phosphate epimerases may be derived from *E. coli, L. plantarum, Arthrobacter aurescens, C. michiganensis, G. forsetii, B. thetaiotamicron* or any other suitable source of the enzyme.

Certain embodiments of the present invention provide for the "inactivation" or "deletion" of certain genes or particular polynucleotide sequences within microorganisms, which "inactivation" or "deletion" of genes or particular polynucleotide sequences may be understood to encompass "genetic modification(s)" or "transformation(s)" such that the resulting strains of said microorganisms may be understood to be "genetically modified" or "transformed." In certain embodiments, strains of microorganisms may be of bacterial, fungal, or yeast origin.

Certain embodiments of the present invention provide for the "insertion," (e.g., the addition, integration, incorporation, or introduction) of certain genes or particular polynucleotide sequences within microorganisms, which insertion of genes or particular polynucleotide sequences may be understood to encompass "genetic modification(s)" or "transformation(s)" such that the resulting strains of microorganisms may be understood to be "genetically modified" or "transformed." In certain embodiments, strains of microorganisms may be of bacterial, fungal, or yeast origin.

The term "CBP organism" is intended to include certain microorganisms of the invention, e.g., microorganisms that have properties suitable for CBP.

The terms "fermenting" and "fermentation" are intended to include the enzymatic process (e.g., cellular or acellular, e.g., a lysate or purified polypeptide mixture) by which ethanol, or another fermentation product is produced from a carbohydrate, in particular, as a result of fermentation.

In one aspect of the invention, the genes or particular polynucleotide sequences are inserted to confer upon the cell the activity encoded by the polynucleotide, such as the expression of an enzyme. In certain embodiments, genes encoding enzymes in the metabolic production of ethanol, e.g., enzymes that metabolize pentose and/or hexose sugars, may be added to a mesophilic or thermophilic organism. In certain embodiments of the invention, the enzyme may confer the ability to metabolize a pentose sugar and be involved, for example, in a xylose-utilization pathway and/or an arabinose-utilization pathway. In certain embodiments of the invention, genes encoding enzymes in the conversion of acetate to a non-charged solvent, including but not limited to, acetone, isopropanol, ethyl acetate, or ethanol, may be added to an organism.

In one aspect of the invention, genes or particular polynucleotide sequences are partially, substantially, or completely deleted, silenced, inactivated, or down-regulated in order to inactivate the activity for which they encode, such as the expression of an enzyme. Deletions provide maximum stability because there is no opportunity for a reverse mutation to restore function. Alternatively, genes can be partially, substantially, or completely deleted, silenced, inactivated, or down-regulated by insertion of nucleic acid sequences that disrupt the function and/or expression of the gene (e.g., P1 transduction or other methods known in the art). The terms "eliminate," "elimination," and "knockout" are used interchangeably with the terms "deletion," "partial deletion," "substantial deletion," or "complete deletion." In certain embodiments, strains of microorganisms of interest may be engineered by site directed homologous recombination to knockout specific genes. In still other embodiments, RNAi or antisense DNA (asDNA) may be used to partially, substantially, or completely silence, inactivate, or down-regulate a particular gene of interest.

In certain embodiments, the genes targeted for deletion or inactivation as described herein may be endogenous to the native strain of the microorganism, and may thus be understood to be referred to as "native gene(s)" or "endogenous gene(s)." An organism is in "a native state" if it has not been genetically engineered or otherwise manipulated by the hand of man in a manner that intentionally alters the genetic and/or phenotypic constitution of the organism. For example, wild-type organisms may be considered to be in a native state. In other embodiments, the gene(s) targeted for deletion or inactivation may be non-native to the organism.

Similarly, the enzymes of the invention as described herein can be endogenous to the native strain of the microorganism, and can thus be understood to be referred to as "native" or "endogenous."

Biomass

Biomass can include any type of biomass known in the art or described herein. The terms "lignocellulosic material," "lignocellulosic substrate," and "cellulosic biomass" mean any type of biomass comprising cellulose, hemicellulose, lignin, or combinations thereof, such as but not limited to woody biomass, forage grasses, herbaceous energy crops, non-woody-plant biomass, agricultural wastes and/or agricultural residues, forestry residues and/or forestry wastes, paper-production sludge and/or waste paper sludge, wastewater-treatment sludge, municipal solid waste, corn fiber from wet and dry mill corn ethanol plants, and sugar-processing residues. The terms "hemicellulosics," "hemicellulosic portions," and "hemicellulosic fractions" mean the non-lignin, non-cellulose elements of lignocellulosic material, such as but not limited to hemicellulose (i.e., comprising xyloglucan, xylan, glucuronoxylan, arabinoxylan, mannan, glucomannan, and galactoglucomannan, inter alia), pectins (e.g., homogalacturonans, rhamnogalacturonan I and II, and xylogalacturonan), and proteoglycans (e.g., arabinogalactan-protein, extensin, and proline-rich proteins).

In a non-limiting example, the lignocellulosic material can include, but is not limited to, woody biomass, such as recycled wood pulp fiber, sawdust, hardwood, softwood, and combinations thereof; grasses, such as switch grass, cord grass, rye grass, reed canary grass, *miscanthus*, or a combination thereof; sugar-processing residues, such as but not limited to sugar cane bagasse; agricultural wastes, such as but not limited to rice straw, rice hulls, barley straw, corn cobs, cereal straw, wheat straw, canola straw, oat straw, oat hulls, and corn fiber; stover, such as but not limited to soybean stover, corn stover; succulents, such as but not limited to, Agave; and forestry wastes, such as but not limited to, recycled wood pulp fiber, sawdust, hardwood (e.g., poplar, oak, maple, birch, willow), softwood, or any combination thereof. Lignocellulosic material may comprise one species of fiber; alternatively, lignocellulosic material may comprise a mixture of fibers that originate from different lignocellulosic materials. Other lignocellulosic materials are agricultural wastes, such as cereal straws, including wheat straw, barley straw, canola straw and oat straw; corn fiber; stovers, such as corn stover and soybean stover; grasses, such as switch grass, reed canary grass, cord grass, and *miscanthus*; or combinations thereof.

Paper sludge is also a viable feedstock for lactate or acetate production. Paper sludge is solid residue arising from pulping and paper-making, and is typically removed from process wastewater in a primary clarifier.

Consolidated Bioprocessing

Consolidated bioprocessing (CBP) is a processing strategy for cellulosic biomass that involves consolidating into a single process step four biologically-mediated events: enzyme production, hydrolysis, hexose fermentation, and pentose fermentation. Implementing this strategy requires development of microorganisms that both utilize cellulose, hemicellulosics, and other biomass components, such as hexose and pentose sugars, while also producing a product of interest at sufficiently high yield and concentrations. The feasibility of CBP is supported by kinetic and bioenergetic analysis. See e.g. van Walsum and Lynd (1998) *Biotech. Bioeng.* 58:316.

Pentose Metabolism

The term "pentose" includes the five-carbon monosaccharides xylose and arabinose that can be metabolized into useful products by the organisms of the present invention. There are two main pathways of xylose metabolism, each pathway is unique in the characteristic enzymes it utilizes. One pathway is called the "Xylose Reductase-Xylitol Dehydrogenase" or XR-XDH pathway. Xylose reductase (XR) and xylitol dehydrogenase (XDH) are the two main enzymes used in this method of xylose degradation. XR, encoded by the GRE3 gene in *S. cerevisiae*, is responsible for the reduction of xylose to xylitol and is aided by cofactors NADH or NADPH. Xylitol is then oxidized to xylulose by XDH, which is expressed through the XYL2 gene, and accomplished exclusively with the cofactor $NAD^+$. Because of the varying cofactors needed in this pathway and the degree to which they are available for usage, an imbalance can result in an overproduction of xylitol byproduct and an inefficient production of desirable ethanol. In some embodiments of the invention the GRE3 gene is deleted to remove the XR-XDH pathway for xylose metabolism from operating in cells of the invention.

The other pathway for xylose metabolism is called the "Xylose Isomerase" (XI) pathway. XI is responsible for direct conversion of xylose into xylulose, and does not proceed via a xylitol intermediate. Both pathways create xylulose, although the enzymes utilized are different. After production of xylulose both the XR-XDH and XI pathways proceed through enzyme xylulokinase (XK), encoded on gene XKS1, to further modify xylulose into xylulose-5-P where it then enters the pentose phosphate pathway for further catabolism.

The xylose isomerase pathway is considered advantageous because it does not produce a cofactor imbalance; however the XR-XDH is endogenous to yeast, whereas the XI pathway is absent. In some embodiments, the cells of the invention comprise an exogenous XI. XI includes those enzymes that correspond to Enzyme Commission Number 5.3.1.5. Suitable xylose isomerases of the present invention include xylose isomerases derived from *Pyromyces* sp., and *B. thetaiotamicron*, although any xylose isomerase that functions when expressed in host cells of the invention can be used.

Arabinose is not efficiently taken up by wild-type *S. cerevisiae*, but small amounts of arabinose present in the cell are naturally processed by an NAD(P)$^+$-dependant dehydrogenase to yield arabinono-1,4-lactone. However, arabinono-1,4-lactone is not a useful intermediate for the production of fermentation products and this pathway does not efficiently use arabinose. Exogenously expressed arabinose transporters of the present invention can confer upon host cells such as *S. cerevisiae* the ability to take up arabinose from the external media. In addition to the sequences listed in SEQ ID NOs: 9-22, Table 2 lists the amino acid sequences of additional arabinose transporters of the invention.

TABLE 2

Amino acid sequences of additional arabinose transporters of the invention and the species from which they are derived.

| | |
|---|---|
| *Zygosaccharomyces rouxii* | mkidkkqigcalmgkrinyrvtiydkfpkiynifyigftscisglmfgfdvssmssmig tdgykeyfgtpgpteqggitacmpagsfvasliapyfsdnfgrrvslhlcaifwmigavl qcasqdlamlcvgrvvsglgigfgssvvapvycseiappkirgaigglfqfsvtlgimilffi gygahfingagsfrltwgielvpgaclliavfflpesprwlalhdyweeaedivirvaakg nreneqvmiqleeireqveidkeaeafqlkdlfrpktrvktmvgmmaqmwqqmcg mnvmmyyivyiftmagfkggavlvsgsiqyvlnvvmtipalflmdkcgrrpvlligg llmcawlfavggllatysdpyphgfegdetvriaipqsnkpaangviacsylfvcsyapt wgvciwiycaeifnnterakgsglctavnwifnfalalfvpsafknltwktyimfgvfcv altintfllfpetkgktleeidqmweahipawkthswvptipsaskfdqemhktdlehve dtgdsdrispkddsekgsvtglcevaksnpnstslse |
| *Vanderwaltozyma polyspora* | mgsfkdtilmknikyegklyerfpkiynyivigfvscisglmfgfdissmssmigtday kqyfgspdatkqggitssmaagsfvgsllsplfsdvfgrryslhicstfwligatlqcasqdl amlvvgrlvsgigigfgsavapvycsevappkirgaiaglfqlsvtlgililyyvgygahfi tsassfrltwgiqlvpgfvllvatfflpesprwlankgfwekatynicrinntdpdniseev aiqleemntqvmddkeadsftyanlfrkktikktivgmsaqmwqqlsginvmmyyi vyifqmagysgnavlvsgsinyilnvamtipalfvidklgrrpilivggilmfvwlfava gllsvysvpvpggyggnetvnimipdnhkhaakgviaccylfvctfaptwgigiwiyc seifnnserakgsslsaavnwifnfalglfvpsafqnitwktylmfgifsvaltihtflmfpe tkgktleeidqmweanipawrsaswkptlpshlhddfknlhtgesssnfveddgkae mekpvvdhiestdksl |
| *Debaryomyces hansenii* | mnsifnysgfvmkftipekyllenkvkgkkithcvvalsalaifffgydqgmmagvnt spdyvekmkygyfnengdvtvtnstrqggivaiyyfgtlvgcvfgglfsdrhgrikaial galiaifgaalqcaaqqmswmcgarfvngigtgilnavvpvyssetaehtsrgafiaieft lnifgvcvaywleyglsyidsgfsafqwrfpiafqiipllvllgivwffpesprwlvknge edhakrillnmrgvergnqefaeivgamrfeqesalsssywrmflgyfpdkdskksak aktlhiarrvqiviwmqifqewvgiagvtvyqpeifkqagfgtrksawlsgvnnifycls tlinfftvdrfgrrftlfwgaigqgismflaggfsklqqknpknssygaaaasfvfiytsifg atwlavpwlypteifplkvraqgnafgvvgwsigngwltllcpimfskigcktlyifgac nfislalvylfepetanrtledidylfandswlaskseadfkrikieqvdkqvgrekqiidid ssekenfstehfe |
| *Aspergillus niger* | myrisniyvlagfgtiggalfgfdvssmsawigtdqyleyfnhpdsdlqggitasmsag sfagalaagfisdrigrryslmlacciwvigaaiqcsaqnvahlvagrvisglsvgitssqv cvylaelaparirgrivgiqqwaiewgmlimylisygcgqlagagaasfrvswgvqgipa lillaalpffpesprwlaskerweealdtlallhakgdrndpvvqveyeevqeaariaqea kdisffslfgpkiwkrtlegvsaqvwqqllggnvamyyvvyifnmagmsgnttlyssa iqyviflvttgtilpfvdrigrrlllltgsvlcmachfaiaglmasrghhvdsvdgnanlkw sitgppgkgviacsyifvavygftwapvawiyasevfplkyrakgvglsaagnwifnfa layfvapaftniqwktyiifgvfctvmtthvfffypetarrsledidlmfetdmkpwkth qihdrfgeeverhkhkdmadqekgvvsthdema |
| *Penicillium chrysogenum* | mytitniyvlaafatiggalfgfdvssmsawigvdtytdyfdspdsnlqggitasmsags fagsiaagwladilgrryalmiaslywivgavvqcsaqnvthlvagrvvsglavgvtssq tcvylselaparirgrivgiqqwaiewgilimyliaygcvvgvsgpaafricwgvqavp glilfialfffpesprwlasqerweealdtlaiihangdrhdpvvqvefeevqeavrvahe srdvsfmalfgprvwkrtmcgmsvqmwqqllggnvamyyvvyifemagmmtgntt lwssaiqyviflvttgcmlpfidrvgrnllligsvtcmvvhyiiaavmaskgkpvpdvn gnanltweikgsagmtviafsyiftgiygltwaptawiyaaevfplkfrakgvglsaatn wifnfalayfvapafhniqwktyiifgvfctvmtfhvffmypetvgrsleeidlvfetdvk pwrthkigdifgeeierrkelgaktetggatheevv |
| *Pichia guilermondii* | mgyedklvapalkfrnfidrtpntynvyviasiscisgamfgfdissmsvfvgqtpylnf fhspksdlqgfitaamslgsffgsllssfvsepfgrrasllicgflwcvgaaiqcssqnvaql iigriisgfgvgfgssvapvygsemaprkirgtiggffqfsvtlgifimfligygcskidav gsfripwgvqivpglflllgcffipesprwlakqgyweeaeiivaniqakgnredpdvli eiseikeqllldehakaftyadlfskkylprtitaisaqiwqqltgmnvmmyyivyifqm agyegdtnlipsliqyiintvvtipslylldrvgrrkmlltaaammawqfgvagilatys epydlndtvkitipdkhksaakgviaccylfvasfastwgvgiwvycsevwgdsqsrq rgaavataanwifnfaigmftpssfknitwktyciyatfcgcmfihvfffffpetkgkrleei aqiweekvpawktskwqphvpllsdhelaekmstkhdenmlqsqsseekptv |
| *A. flavus* | mcdqipkwnvvhrlekrklliginsvaalsilffgydqgmmagvnnskdyidlmgfg ytemkdgyltpvvtdsllqggivsvyylgtlfgallggwigdrigriktiaagalwailgaa lqcsaqnhnwmicsrfingigtgilnaivpvwatetaehtsrgqflaieftlnifgvvlayw lefglsfidggrspfrwrfpiatqiiflvllfvvvwffpesprwlvkvgreqearyilgrlrgs sdedavraeaefrdiqnvaemeksmnhstsylamlfgyktgklhlgrrvqlviwlqim qewvgiagvtvyaptifsiagfdsmksqwisglnnvfymfatlvcvfftldrigrrwtlyw |

TABLE 2 -continued

Amino acid sequences of additional arabinose transporters of the invention and the species from which they are derived.

| | |
|---|---|
| | gsiaqgiamflaggfsrlaidaradgnisransfgaaaasmvfiftsvfgatwltvvpwiy<br>paeiyplavrakgnawgvvgwsigngwltllcpvmfeaigektlyvfaasnvitipmv<br>walypesnqrtledmdllfaaetpwvwdaertfarlkaenpgyietanrknsavdpem<br>gkptdaheehassas |
| C. lusitnaea | mgyeeklvapalklrrfldrtpntynvyfiasiscisgmmfgfdissmsvfvsdkpylny<br>fdhpssvmqgfitaamslgsffgslsssfvsepfgrrasllicgflwcvgaaiqcsaqnra<br>qliigriisgwgvfgssyspvygselsprkirgfvggmfgfsvtfgilimfliaygmshv<br>hgkasfrvswgvgivpglvlliglffipesprwlakqgywdeafivakiqakgnredp<br>evgielseikeqllleehaknftyadlfspkyrvrtvtavfaqiwqqlltgmnvmmyyiv<br>yifemagyegntnlipsliqyiinsavtvpstylldkvgrrtlllfgaagmmafgfavagll<br>atysipheykgndtvritipkknkpaargviaccylfvvcfastwgvgiwvycsevwg<br>dnrsrqrgaslstsanwifhfaiamftpsstknitwktyiiyavfcccmfvhvffcfpetrg<br>krleeiaqiwdekvpawktrnwqphvpllsdaqleeklnvnhaenagedkavqshss<br>sdgqv |
| C. albicans<br>(SC5314) | mksplelalggtalkistfldklpkiynvyfiasistiagmmfgfdissmsafigtetymdf<br>fnspgsdiqgfitssmalgsffgsiassfisepfgrrlsliicaffwmvgaaiqssvqnraql<br>iigriisgvgvfgssvatiygaelaprkirgfiggmfqffvtlgilimfylsfglghikgva<br>sfriawglqivpglmlfigeffipesprwlakqnrweqaeyivsriqakgnredpdvliei<br>seikdqllieeaksvsyatlfrkkyllrtftaifaqiwqqltgmnvmmyyivyifmag<br>ysgnanlvassiqyvintgvtipalffvdrigrrpvlitgavlmmtfqfglagilgqysvp<br>wtdsgndsvniripednksaskgaiaccylfvasfastwgptiwiyeseiwgdnrvaqr<br>gnslataanwilnfaigmytpagfksiswrtyitygymcftmaihvyfgfpetkgkrlee<br>igqmweehypawksrswqphypiasdaelarkmdvehkegglmnedtnseakaesv |

Conversely, some organisms contain an arabinose pathway that converts arabinose into xylulose, which can then enter the pentose phosphate pathway for further catabolism, leading to fermentation. This arabinose pathway comprises an arabinose isomerase (AI) (encoded by AraA), a ribulokinase (RK) (encoded by AraB) and an epimerase (R5PE) (encoded by AraD). The AraA isomerase converts arabinose to ribulose; the AraB ribulokinase phosphorylates the ribulose to yield ribulose-phosphate; and the AraD ribulose 5-phosphate epimerase converts ribulose-phosphate to xylulose-phosphate which enters the pentose phosphate pathway and can ultimately be converted to glucose, or glycolytic intermediates to yield fermentation products.

Host Cells

Host cells useful in the present invention include prokaryotic or eukaryotic cells; for example, microorganisms selected from bacterial and yeast cells. Among host cells suitable for the present invention are microorganisms, for example, of the genera *Aeromonas, Aspergillus, Clostridium, Bacillus, Escherichia, Kluyveromyces, Pichia, Rhodococcus, Saccharomyces* and *Streptomyces*.

In some embodiments, the host cells are microorganisms. In one embodiment the microorganism is a yeast. According to the present invention the yeast host cell can be, for example, from the genera *Saccharomyces, Kluyveromyces, Candida, Pichia, Schizosaccharomyces, Hansenula, Kloeckera, Schwanniomyces*, and *Yarrowia*. In one particular embodiment, the yeast is *Saccharomyces cerevisiae*. In another embodiment, the yeast is a thermotolerant *Saccharomyces cerevisiae*. The selection of an appropriate host is deemed to be within the scope of those skilled in the art from the teachings herein.

In some embodiments, the host cell is an oleaginous cell. The oleaginous host cell can be an oleaginous yeast cell. For example, the oleaginous yeast host cell can be from the genera *Blakeslea, Candida, Cryptococcus, Cunninghamella, Lipomyces, Mortierella, Mucor, Phycomyces, Pythium, Rhodosporidum, Rhodotorula, Trichosporon* or *Yarrowia*.

In some embodiments, the host cell is a thermotolerant host cell. Thermotolerant host cells can be particularly useful in simultaneous saccharification and fermentation processes by allowing externally produced cellulases and ethanol-producing host cells to perform optimally in similar temperature ranges.

In some particular embodiments, the host cell is a *Kluyveromyces* host cell. The host cells can contain antibiotic markers or can contain no antibiotic markers. In another embodiment, the host cells are bacteria selected from the genus *Clostridium, Acinetobacter, Thermoanaerobacterium*, and other bacteria having characteristics resembling those of *Clostridium* species.

Several microorganisms that are reported in the literature to be cellulolytic or have cellulolytic activity have been characterized by a variety of means, including their ability to grow on microcrystalline cellulose as well as a variety of other sugars. Additionally, such organisms may be characterized by other means, including but not limited to, their ability to depolymerize and debranch cellulose and hemicellulose.

Certain microorganisms, including, for example, *S. cerevisiae*, cannot metabolize pentose sugars, such as xylose or arabinose, but are able to metabolize hexose sugars. Both xylose and arabinose are abundant sugars in biomass with xylose accounting for approximately 16-20% in soft and hard woods and L-arabinose accounting for approximately 25% in corn fiber. Accordingly, one embodiment of the invention is a genetically-modified cellulolytic microorganism, with the ability to metabolize pentose sugars, such as xylose and arabinose, thereby to enhance its use as a biocatalyst for fermentation in the biomass-to-acetic acid or lactic acid or ethanol industries. Therefore, in some embodiments, the host cell is a *S. cerevisiae* strain.

In some embodiments, the thermotolerant host cell can grow at temperatures above about 30° C., about 31° C., about 32° C., about 33° C., about 34° C., about 35° C., about 36° C., about 37° C., about 38° C., about 39° C., about 40° C., about 41° C. or about 42° C. In some embodiments of the present invention the thermotolerant host cell can produce ethanol from xylose at temperatures above about 30° C., about 31° C., about 32° C., about 33° C., about 34° C., about 35° C., about 36° C., about 37° C., about 38° C., about 39° C., about 40° C., about 41° C., about 42° C., or about 43° C., or about 44° C., or about 45° C., or about 50° C.

In some embodiments of the present invention, the thermotolerant host cell can grow at temperatures from about 30° C. to 60° C., about 30° C. to 55° C., about 30° C. to 50° C., about 40° C. to 60° C., about 40° C. to 55° C. or about 40° C. to 50° C. In some embodiments of the present invention, the thermotolerant host cell can produce ethanol from xylose at temperatures from about 30° C. to 60° C. about 30° C. to 55° C., about 30° C. to 50° C., about 40° C. to 60° C., about 40° C. to 55° C. or about 40° C. to 50° C.

In some embodiments, the host cell is a host cell that exhibits high ethanol tolerance. High ethanol tolerant strains are able to produce an ethanol titer higher than a non-high ethanol tolerant strain containing the same modifications according to the present invention, under identical growth conditions. Such industrially hearty strains are known in the art of industrial ethanol production. In some embodiments, the high ethanol tolerant strains can produce ethanol titers of up to 4%, up to 5%, up to 6%, up to 7%, up to 8%, up to 9%, up to 10%, up to 11%, up to 12%, up to 13%, up to 14%, up to 15%, up to 16%, and up to 17% ethanol in the fermentation media.

The present invention provides cellulolytic microorganisms expressing enzymes that allow the microorganisms to ferment xylose and/or arabinose. When genes encoding enzymes involved in the metabolic pathway of lactate or acetate, including, for example, xylose and/or arabinose, are introduced into a microorganism that lacks one or more of these genes, for example, *S. cerevisiae*, one may select transformed strains for growth on xylose or growth on arabinose. *S. cerevisiae* may lack one or more known genes or enzymes in the arabinose to ethanol pathway and/or the arabinose utilization pathway.

In one embodiment, host cells are genetically engineered (transduced or transformed or transfected) with the polynucleotides encoding arabinose-utilizing enzymes of this invention. In some embodiments, the polynucleotides encoding arabinose-utilizing enzymes can be introduced to the host cell on a vector, which may be, for example, a cloning vector or an expression vector comprising a sequence encoding a heterologous xylose metabolizing enzyme. The host cells can comprise polynucleotides of the invention as integrated copies or plasmid copies.

In some embodiments, the arabinose-utilizing enzymes may be introduced as a series of overlapping segments and cotransformed into the host cells so as to accomplish multiple homologous recombination events, which render a complete construct within the host cell. In further embodiments, the assembled construct contains homology to a target segment of the host cell genome and the entire, assembled construct integrates into the host cell genome.

In certain aspects, the present invention relates to host cells containing the polynucleotide constructs described below by way of specific examples. The host cells of the present invention can express one or more heterologous polypeptides expressing xylose metabolizing enzymes in addition to the arabinose-utilizing enzymes. In some embodiments, the host cell comprises a combination of polynucleotides that encode heterologous xylose metabolizing enzymes or fragments, variants or derivatives thereof. The host cell can, for example, comprise multiple copies of the same nucleic acid sequence, for example, to increase expression levels, or the host cell can comprise a combination of unique polynucleotides. In other embodiments, the host cell comprises a single polynucleotide that encodes a heterologous xylose metabolizing enzyme or a fragment, variant or derivative thereof. For example, in some embodiments the host cells of the invention have an up-regulated pentose phosphate pathway. In some embodiments, the pentose phosphate pathway genes that are up-regulated are transketolase, transaldolase, ribulose-5-phosphate-3-epimerase, and/or ribulose-5-phosphate isomerase. However, in alternative embodiments, the endogenous pentose phosphate pathway of the host cell is not genetically manipulated.

In some embodiments, the microorganisms of the invention contain enzymes involved in cellulose digestion, metabolism and/or hydrolysis. A "cellulolytic enzyme" can be any enzyme involved in cellulose digestion, metabolism, and/or hydrolysis. The term "cellulase" refers to a class of enzymes produced chiefly by fungi, bacteria, and protozoans that catalyze cellulolysis (i.e. the hydrolysis) of cellulose. However, there are also cellulases produced by other types of organisms such as plants and animals. Several different kinds of cellulases are known, which differ structurally and mechanistically. There are general types of cellulases based on the type of reaction catalyzed: endocellulase breaks internal bonds to disrupt the crystalline structure of cellulose and expose individual cellulose polysaccharide chains; exocellulase cleaves 2-4 units from the ends of the exposed chains produced by endocellulase, resulting in the tetrasaccharides or disaccharide such as cellobiose. There are two main types of exocellulases (or cellobiohydrolases, abbreviate CBH)—one type working processively from the reducing end, and one type working processively from the non-reducing end of cellulose; cellobiose or beta-glucosidase hydrolyses the exocellulase product into individual monosaccharides; oxidative cellulases that depolymerize cellulose by radical reactions, as for instance cellobiose dehydrogenase (acceptor); cellulose phosphorylases that depolymerize cellulose using phosphates instead of water. In the most familiar case of cellulase activity, the enzyme complex breaks down cellulose to beta-glucose. A "cellulase" can be any enzyme involved in cellulose digestion, metabolism and/or hydrolysis, including, for example, an endoglucanase, glucosidase, cellobiohydrolase, xylanase, glucanase, xylosidase, xylan esterase, arabinofuranosidase, galactosidase, cellobiose phosphorylase, cellodextrin phosphorylase, mannanase, mannosidase, xyloglucanase, endoxylanase, glucuronidase, acetylxylanesterase, arabinofuranohydrolase, swollenin, glucuronyl esterase, expansin, pectinase, and feruoyl esterase protein.

This full suite of cellulase enzymes that can be used in host cells and methods of the present invention contains activities beyond those identified previously for expression in yeast: CBH1, CBH2, EG, and BGL (as disclosed e.g. in PCT Application No. PCT/US2009/065571). In some embodiments, the present invention relates to a yeast cell that expresses one or more gene products of the genes: *Aspergillus fumigatus* Endoglucanase (Accession No. XP_747897); *Neosartorya fischeri* Endoglucanase (Accession No. XP_001257357); *Aspergillus clavatus* Endoglucanase (Accession No. XP_001270378); *Aspergillus terreus* Endoglucanase (Accession No. XP_001217291); *Penicillium marneffei* Endoglucanase (Accession No. XP 002152969); *Chaetomium globosum* Endoglucanase (Accession No. XP_001229968); *Neurospora crassa* Endoglucanase (Accession No. XP_956431); *Aspergillus oryzae* Endoglucanase (Accession No. BAA22589); *Thielavia heterothallica* Endoglucanase (Accession No. AAE25067); *Fusarium oxysporum* Endoglucanase (Accession No. AAG09047); *Humicola insolens* Endoglucanase (Accession No. 1DYM_A); *Pyrenophora tritici-repentis* Endoglucanase (Accession No. XP 001935476); *Magnaporthe grisea* Endoglucanase (Accession No. XP_370166); *Fusarium graminearum* Endoglucanase (Accession No. XP_388429); *Chrysosporium lucknowense* Endoglucanase; *Polyporus arcularius* Endoglucanase (Accession No. BAF75943.1); *Aspergillus kawachii* Endoglucanase (Accession No. BAB62317.1); *Heterodera schachtii* Endoglucanase (Accession No. CAC12958.1); *Orpinomyces* sp. Endoglucanase (Accession No. AAD04193.1); *Irpex lacteus* Endoglucanase (Accession No. BAD67544.1); *Chaetomium globosum* Endoglucanase (Accession No. XP_001220409.1); *Aspergillus niger* Endoglucanase (Accession No. XP_001397982.1); *Penicillium decumbens* Endoglucanase (Accession No. ABY28340.1); *Phanerochaete chrysosporium* Endoglucanase (Accession No. AAU12276); *Stachybotrys echinata* Endoglucanase (Accession No. AAM77710); *Neosartorya fischeri* Endoglucanase (Accession No. XP_001261563); *Chaetomium brasiliense* Endoglucanase (Accession No. AAM77701); *Chaetomium globosum* Endoglucanase (Accession No. EAQ86340); *Aspergillus fumigatus* Endoglucanase (Accession No. CAF31975); *Humicola insolens* Endoglucanase (Accession No. CAG27577); *Neosartorya fischeri* Endoglucanase (Accession No. XP_001267517); *Thielavia terrestris* Endoglucanase (Accession No. ACE10231); *Chrysosporium lucknowense* Endoglucanase (Accession No. ACH15008); *Chaetomium globosum* Endoglucanase (Accession No. XP_001226436); *Acremonium thermophilum* Endoglucanase (Accession No. ACE10216); *Humicola insolens* Endoglucanase (Accession No. CAB42307); *Thielavia terrestris* Endoglucanase (Accession No. CAH03187); *Chrysosporium lucknowense* Endoglucanase (Accession No. AAQ38151); *Magnaporthe grisea* Endoglucanase (Accession No. EDJ97375); *Chaetomium globosum* Endoglucanase (Accession No. EAQ84577); *Humicola insolens* Endoglucanase 1DYS_B; *Neurospera crassa* Endoglucanase (Accession No. XP_957415); *Trichoderma reesei* Xyloglucanase (Accession No. AAP57752); *Aspergillus niger* Xyloglucanase (Accession No. AAK77227); *Aspergillus aculeatus* Xyloglucanase (Accession No. BAA29031); *Neosartorya fischeri* Xyloglucanase (Accession No. XP_001261776); *Chaetomium thermophilum* Endoxylanase (Accession No. CAD48749); *Trichoderma reesei* Endoxylanase (Accession No. ABK59833); *Chrysosporium lucknowense* Endoxylanase (Accession No. AAQ38147); *Aureobasidium pullulans* Endoxylanase (Accession No. BAE71410); *Aspergillus nidulans* beta-xylosidase (Accession No. CAA73902: *Cochliobolus carbonum* beta-xylosidase (Accession No. BAC67554); *Penicillium herquei* beta-xylosidase (Accession No. BAC75546); *Pyrenophora tritici-repentis* beta-xylosidase (Accession No. XP_001940956); *Aspergillus niger* beta-mannosidase (Accession No. Q9UUZ3); *Aspergillus aculeatus* beta-mannosidase (Accession No. BAA29029); *Neosartorya fischeri* beta-mannosidase (Accession No. XP 001258000); *Trichoderma reesei* alpha-glucuronidase (Accession No. CAA92949); *Aspergillus niger* alpha-glucuronidase (Accession No. CAC38119); *Talaromyces emersonii* alpha-glucuronidase (Accession No. AAL33576); *Aspergillus niger* acetylxylanesterase (Accession No. XP_001395572); *Trichoderma reesei* acetylxylanesterase (Accession No. Q99034); *Neosartorya fischeri* acetylxylanesterase (Accession No. XP 001262186); *Trichoderma reesei* arabinofuranosidase, 1,4-beta-D-arabinoxylan arabinofuranohydrolase (Accession No. AAP57750); *Chaetomium globosum* arabinofuranosidase, 1,4-beta-D-arabinoxylan arabinofuranohydrolase (Accession No. XP_001223478); *Aspergillus niger* arabinofuranosidase, 1,4-beta-D-arabinoxylan arabinofuranohydrolase (Accession No. XP_001389998); *Penicillium decumbens* Swollenin (Accession No. ACH57439); *Neosartorya fischeri* Swollenin (Accession No. XP_001257521); *Talaromyces stipitatus* Swollenin (Accession No EED19018); *Trichoderma reesei* (Accession No. AAP57751); *Chaetomium globosum* (Accession No. XP_001228455); *Magnaporthe grisea* (Accession No. XP_365869); *Trichoderma reesei* glucuronyl esterase (Accession No. AAP57749); *Chaetomium globosum* glucuronyl esterase (Accession No. XP_001226041); *Aspergillus fumigatus* glucuronyl esterase (Accession No. XP_751313); *Populus alba* alpha-expansin (Accession No. BAB39482); *Vitis lubrusca* alpha-expansin (Accession No. BAC66697); *Triticum aestivum* beta-expansin (Accession No. AAS48881); *Eucalyptus globulus* beta-expansin (Accession No. AAZ08315); *Aspergillus niger* Feruoyl esterase (Accession No. XP_001393337); *Aspergillus terreus* Feruoyl esterase (Accession No. XP_001211092); *Talaromyces stipitatus* Feruoyl esterase (Accession No. EED17739); *Chaetomium globosum* Feruoyl esterase (Accession No. XP_001228412) *Streptomyces avermitilis* 1,4-beta-cellobiosidase guxA1 (Accession No. NP_821732.1); *Streptomyces avermitilis* 1,4-beta-cellobiosidase guxA2 (Accession No. NP_823029.1); *Streptomyces avermitilis* 1,4-beta-cellobiosidase guxA3 (Accession No. NP_823031.1); *Streptomyces avermitilis* Endo-1,4-beta-glucanase celA1 (Accession No. NP_821730.1); *Streptomyces avermitilis* Endo-1,4-beta-glucanase celA2 (Accession No. NP_823030.1); *Streptomyces avermitilis* Endo-1,4-beta-glucanase celA3 (Accession No. NP_823032.1); *Streptomyces avermitilis* Endo-1,4-beta-glucanase celA4 (Accession No. NP_823744.1); *Streptomyces avermitilis* Endo-1,4-beta-glucanase (Accession No. NP_826394.1); *Streptomyces avermitilis* Endo-1,4-beta-glucanase celA5 (Accession No. NP_828072.1); *Streptomyces avermitilis* Beta-1,4-xylanase (Accession No. NP_823272.1); *Streptomyces avermitilis* Beta-1,4-xylanase (Accession No. NP_826161.1); *Streptomyces avermitilis* Xylanase (Accession No. NP_827548.1); *Streptomyces avermitilis* Endo-1,4-beta-xylanase xynD (Accession No. NP_827557.1); *Streptomyces avermitilis* 1,4-beta-xylosidase xynB1 (Accession No. NP_822628.1); *Streptomyces avermitilis* Beta-xylosidase (Accession No. NP_823285.1); *Streptomyces avermitilis* 1,4-beta-xylosidase xynB2 (Accession No. NP_826159.1); *Streptomyces avermitilis* 1,4-beta-xylosidase xynB3 (Accession No. NP_827745.1); *Streptomyces avermitilis* Beta-glucosidase bglC1 (Accession No. NP_822977.1); *Streptomyces avermitilis* Beta-glucosidase bglC2 (Accession No. NP_826430.1); *Streptomyces avermitilis* Beta-glucosidase bglC3 (Accession No. NP_826775.1); *Streptomyces avermitilis* AXE1 (Accession No. NP_822477.1); *Streptomyces avermitilis* AXE1 (Accession No. NP_822632.1); *Streptomyces avermitilis* abfA (Accession No. NP_822218.1); *Streptomyces avermitilis* abfB (Accession No. NP_822290.1); *Streptomyces avermitilis* abfA (Accession No. NP 826920.1); *Streptomyces avermitilis* abfB (Accession No. BAC74043.1); *Streptomyces avermitilis* SAV_6756 (Accession No. BAC74467.1); *Streptomyces avermitilis* agaA1 (Accession No. BAC68338.1); *Streptomyces avermitilis* agaA3 (Accession No. BAC68787.1); *Streptomyces avermitilis* agaB2 (Accession No. BAC69185.1); *Saccharophagus degradans* 2-40 Sde_2993 (Accession No. YP_528462.1); *Saccharophagus degradans* 2-40 Sde_2996 (Accession No. YP_528465.1); *Saccharophagus degradans* 2-40 Sde_3023 (Accession No. YP_528492.1); *Saccharophagus degradans* 2-40 cel5A (Accession No. ABD82260.1); *Saccharophagus degradans*

2-40 cel5E (Accession No. ABD82186.1); *Saccharophagus degradans* 2-40 cel5F (Accession No. ABD80834.1); *Saccharophagus degradans* 2-40 cel5J (Accession No. ABD81754.1; *Saccharophagus degradans* 2-40 cel9A (Accession No. ABD79898.1); *Saccharophagus degradans* 2-40 ced3A (Accession No. ABD81757.1); *Saccharophagus degradans* 2-40 ced3B (Accession No. ABD79509.1); *Saccharophagus degradans* 2-40 bgl1A (Accession No. ABD82858.1); *Saccharophagus degradans* 2-40 bgl1B (Accession No. ABD80656.1); *Saccharophagus degradans* 2-40 Cep94A (Accession No. ABD80580.1); *Saccharophagus degradans* 2-40 Cep94B (Accession No. ABD80168.1); *Saccharophagus degradans* 2-40 Sde_0509 (Accession No. YP_525985.1); *Saccharophagus degradans* 2-40 Sde_0169 (Accession No. YP_525645.1); *Bacillus subtilis* Expansin exlX (Accession No. CAB13755.1); *Bacillus subtilis* Endo-1,4-beta-glucanase eglS (Accession No. CAB13696.2); *Bacillus subtilis* Endo-xylanase xynC (Accession No. CAB13698.1); *Bacillus subtilis* Endo-1,4-beta-xylanase xynD (Accession No. CAB13699.1); *Bacillus subtilis* Endo-1,4-beta-xylanase xynA (Accession No. CAB13776.1); *Bacillus subtilis* Xylan beta-1,4-xylosidase xynB (Accession No. CAB13642.2); *Clostridium phytofermentans* Cphy_3367 (Accession No. YP_001560459.1); *Clostridium phytofermentans* Cphy_3368 (Accession No. YP_001560460.1); *Clostridium phytofermentans* Cphy_2058 (Accession No. YP_001559165.1); *Clostridium phytofermentans* Cphy_3202 cellulase B (Accession No. YP_001560295.1); *Clostridium phytofermentans* Cphy_1163 (Accession No. YP_001558280.1); *Clostridium phytofermentans* Cphy_3329 (Accession No. YP_001560421.1); *Clostridium phytofermentans* Cphy_1125 (Accession No. YP_001558242.1); *Clostridium phytofermentans* Cphy_1510 (Accession No. YP_001558623.1); *Clostridium phytofermentans* Cphy_0624 (Accession No. YP_001557750.1); *Clostridium phytofermentans* Cphy_2105 XynA (Accession No. YP_001559210.1); *Clostridium phytofermentans* Cphy_2108 (Accession No. YP_001559213.1); *Clostridium phytofermentans* Cphy_3207 Y (Accession No. YP_001560300.1); *Clostridium phytofermentans* Cphy_0191 (Accession No. YP_001557317.1); *Clostridium phytofermentans* Cphy_0875 (Accession No. YP_001558000.1); *Clostridium phytofermentans* Cphy_169 (Accession No. YP_001558286.1); *Clostridium phytofermentans* Cphy_1071 (Accession No. YP_001558190.1); *Clostridium phytofermentans* Cphy_2128 (Accession No. YP_001559233.1); *Clostridium phytofermentans* Cphy_2276 (Accession No. YP_001559376.1); *Clostridium phytofermentans* Cphy_1936 (Accession No. YP_001559043.1); *Clostridium cellulolyticum* cel51 (Accession No. AAL79562.1); *Clostridium cellulolyticum* CelCCF (dockerin) Cel48F-yeast CO template pMU914 (Accession No. AAB41452.1); *Clostridium cellulolyticum* Ccel_1259 (Accession No. YP_002505595); *Clostridium cellulolyticum* Ccel_2226 (Accession No. YP_002506548.1); *Clostridium cellulolyticum* Ccel_0732 (dockerin) Cel9E-yeast CO template pMU913 (Accession No. YP_002505091.1); *Clostridium cellulolyticum* Ccel_1099 (dockerin) Cel5A-yeast CO template pMU967 (Accession No. YP_002505438.1); *Clostridium cellulolyticum* Ccel_2392 (dockerin) (Accession No. YP_002506705.1); *Clostridium cellulolyticum* Ccel_0731 (dockerin) Cel9G-yeast CO template pMU892 (Accession No. YP_002505090.1); *Clostridium cellulolyticum* Ccel_0840 (dockerin) Cel5D-yeast CO template pMU891 (Accession No. YP_002505196.1); *Clostridium cellulolyticum* CelCCC (dockerin) Cel8C-yeast CO template pMU969 (Accession No. AAA73867.1); *Thermobifida fusca* endo-1,4-beta xylanase (Accession No. ABL73883.1); *Thermobifida fusca* endo-1,4-beta-D-xylanase (xyl11) (Accession No. AAV64879.1); *Thermobifida fusca* Endoglucanase (Accession No. AAZ55112.1); *Thermobifida fusca* cellulase (Accession No. AAZ56745.1); *Thermobifida fusca* exo-1,4-beta-glucosidase (Accession No. AAL55642.1); *Thermobifida fusca* beta-glucosidase (Accession No. AAZ55664.1); *Thermobifida fusca* cellulose 1,4-beta-cellobiosidase (Accession No. YP_290015.1); *Thermobifida fusca* CBD E8 (Accession No. AAZ55700.1); *Thermobifida fusca* celC (E3) (Accession No. YP_288681.1); *Thermobifida fusca* celE (E5) (Accession No. YP_288962.1); *Thermobifida fusca* cel5B (Endoglucanase) (Accession No. AAP56348.1); *Thermobifida fusca* celA (E1) (Accession No. AAC06387.1); *Thermobifida fusca* celB (E2) (Accession No. YP_289135.1); *Thermobifida fusca* Tfu_1627 (1,4-beta-cellobiosidase) (Accession No. YP_289685.1); *Clostridium thermocellum* celA (dockerin) (Accession No. YP_001036701.1); *Clostridium thermocellum* celY (cel48Y) (Accession No. CAI06105.1); *Clostridium thermocellum* Cthe_0625 (dockerin) (Accession No. YP_001037053.1); *Clostridium thermocellum* celC (Accession No. CAC27410.1); *Clostridium thermocellum* (Accession No. YP_001037893.1); *Clostridium thermocellum* (Accession No. YP_001038519.1); *Clostridium thermocellum* bglA (Accession No. CAA42814.1); *Clostridium thermocellum* bglB (Accession No. CAA33665.1); *Clostridium thermocellum* Cthe_2548 (Accession No. YP_0010389421.1, *Clostridium thermocellum* Cthe_1273 (Accession No. YP_001037698.1); *Clostridium thermocellum* Cthe_0040 (Cel91) (Accession No. YP_001036474.1); *Clostridium thermocellum* Cthe_0412 (dockerin) (Accession No. YP_001036843.1); *Clostridium thermocellum* Cthe_0825 (dockerin) (Accession No. YP_001037253.1); *Clostridium stercorarium* xynA (Accession No. CAD48307); *Clostridium stercorarium* xynB (CelW—celloxylanase) (Accession No. CAD48313); *Clostridium stercorarium* xynC (CelX—celloxylanase) (Accession No. CAD48314); *Clostridium stercorarium* bxlB (b-Xylosidase B) (Accession No. AJ508405); *Clostridium stercorarium* bxlA (b-Xylosidase A) (Accession No. AJ508404); *Clostridium stercorarium* bglZ (beta-glucosidase) (Accession No. CAB08072); *Clostridium stercorarium* arfA (alpha-arabinofuranosidaseA) (Accession No. AJ508406); *Clostridium stercorarium* arfB (alpha-arabinofuranosidaseB) (Accession No. AAC28125); *Clostridium stercorarium* celZ (Cs-Cel9Z—Avicellase I) (Accession No CAA39010); *Clostridium stercorarium* celY (Cs-Cel48Y—Avicellase II) (Accession No. CAA93280); *Anaerocellum thermophilum* celA (1,4-beta-glucanase) (Accession No. CAB06786); *Anaerocellum thermophilum* celD (EG) (Accession No. CAB01405); *Anaerocellum thermophilum* xynA (1,4-beta-D-xylan xylanhydrolase) (Accession No. CAA93627); *Anaerocellum thermophilum* celB (EG5) (Accession No. 786104); *Anaerocellum thermophilum* Athe_1866 (endo-1,4-beta-mannosidase) (Accession No. YP_002573059); *Anaerocellum thermophilum* Athe_0594 ("cellulase") (Accession No. YP_002572493).

Additionally, host cells of the invention may be used in co-culture with other host cells that are capable of performing some beneficial function. For example, cells capable of breaking down cellulose can be co-cultured with the arabinose-utilizing cells of the invention. In such embodiments, co-cultured cells express cellulases and can release sugars into the media. As used herein, "co-culture" refers to growing two different strains or species of host cells together in the same vessel either contemporaneously or serially. Additionally, "co-culture" can mean that different strains or species of host cell are in fluid communication with each other, but in different containers.

Introduction of a polynucleotide encoding one or more heterologous arabinose-utilizing enzymes into a host cell can be done by methods known in the art. Introduction of polynucleotides encoding heterologous xylose metabolizing enzymes into, for example yeast host cells, can be effected by lithium acetate transformation, spheroplast transformation, or transformation by electroporation, as described in *Current Protocols in Molecular Biology*, 13.7.1-13.7.10. Introduction of the construct in other host cells can be effected by calcium phosphate transfection, DEAE-Dextran mediated transfection, or electroporation. (Davis, L., et al., *Basic Methods in Molecular Biology*, (1986)).

In certain embodiments, arabinose-utilizing gene donors may include microorganisms that confer to the host cell, the ability to metabolize hexose and pentose sugars. In some embodiments, such microorganisms are *Thermoanaerobacterium saccharolyticum, C. cellulolyticum, Caldicellulosiruptor kristjanssonii, C. phytofermentans, C. stercorarium. Pyromyces* spp. and *B. thetaiotamicron.*

Accordingly, it is an embodiment of the invention to modify one or more microorganism strains so as to optimize sugar utilization capability by, for example, introducing genes for one or more enzymes required for the production of a fermentation product from biomass-derived pentoses, e.g., D-xylose or L-arabinose metabolism. Promoters, including native promoters of the host cell may be used to express these genes. Such promoters include, for example, the ADH1 and the ENO1 promoter of *S. cerevisiae*. Suitable yeast promoters are well known in the art. Promoters of the invention may be constitutive or inducible. See e.g. Table 1.

Similarly, terminator sequences normally endogenous to the host cell can also be used to express the genes of the invention. Such terminator sequences include, for example, the PDC1 the ENO1 and the PDC1 terminators from *S. cerevisiae*. Once the gene or genes have been cloned, codon optimization may be performed before expression. Cassettes containing, for example, the native promoter, one or more arabinose-utilization genes and a selectable marker may then be used to transform the host cell and select for successful transformants.

In additional embodiments, the transformed host cells or cell cultures are assayed for ethanol production. Ethanol production can be measured by techniques known to one of ordinary skill in the art, e.g., by a standard HPLC refractive index method.

Heterologous Arabinose-Metabolizing Enzymes

According to one aspect of the present invention, the expression of heterologous arabinose-metabolizing enzymes in a host cell can be used advantageously to produce products such as ethanol from the arabinose portion of cellulosic sources. Arabinose-metabolizing enzymes from a variety of sources can be heterologously expressed to successfully increase efficiency of ethanol production, for example. The arabinose-metabolizing enzymes can be from fungi, bacteria, plants, and protozoan or termite sources. In some embodiments, the arabinose-metabolizing enzyme is a *Thermoanaerobacterium saccharolyticum, H. grisea. T. aurantiacus, T. emersonii, T. reesei, C. lacteus, C. formosanus, N. takasagoensis, C. acinaciformis, M. darwinensis, N. walkeri, S. fibuligera, C. luckowense R. speratus, Thermobfida fusca, Clostridium cellulolyticum, Clostridum josui, Bacillus pumilis, Cellulomonas fimi, Saccharophagus degradans, Piromyces equii, Neocallimastix patricarum* or *Arabidopsis thaliana* arabinose-metabolizing enzyme. In some embodiments, the arabinose-metabolizing enzyme is a *B. thetaiotamicron* arabinose-metabolizing enzyme. In some embodiments, the arabinose-metabolizing enzyme of the invention is any arabinose-metabolizing enzyme known in the art. In a specific embodiment, the arabinose-metabolizing enzyme of the invention is an enzyme disclosed in Table 2. In some embodiments, the arabinose-metabolizing enzyme is encoded by a nucleic acid sequence at least about 80%, at least about 85%, at least about 90%, at least about 95%, at least about 96%, at least about 97%, at least about 98%, at least about 99%, or 100% identical to any one of SEQ ID NOs: 1-5. In some embodiments, the arabinose-metabolizing enzyme has an amino acid sequence that is at least about 80%, at least about 85%, at least about 90%, at least about 95%, at least about 96%, at least about 97%, at least about 98%, at least about 99%, or 100% identical to any one of SEQ ID NOs: 6-10. In some embodiments, the arabinose-metabolizing enzyme of the invention is any arabinose-metabolizing enzyme suitable for expression in an appropriate host cell.

In some embodiments of the invention, multiple arabinose-metabolizing enzymes from a single organism are co-expressed in the same host cell. In some embodiments of the invention, multiple arabinose-metabolizing enzymes from different organisms are co-expressed in the same host cell. In particular, arabinose-metabolizing enzymes from two, three, four, five, six, seven, eight, nine or more organisms can be co-expressed in the same host cell. Similarly, the invention can encompass co-cultures of microorganism strains, wherein the microorganism strains express different arabinose-metabolizing enzymes. Co-cultures can include microorganism strains expressing heterologous arabinose-metabolizing enzymes from the same organism or from different organisms. Co-cultures can include microorganism strains expressing arabinose-metabolizing enzymes from two, three, four, five, six, seven, eight, nine or more microorganisms.

In some aspects of the invention, one or more of the native enzymes in the engineered metabolic pathways are downregulated or deleted. In certain embodiments, the downregulated or deleted native enzyme is an enzyme involved in central metabolism. In some embodiments, the downregulated or deleted native enzyme is selected from the group consisting of a pyruvate kinase; a hydrogenase; a lactate dehydrogenase; a phosphotransacetylase; an acetate kinase; an acetaldehyde dehydrogenase; a glyceraldehyde phosphate dehydrogenase; pyruvate formate lyase, an aldose reductase; an alcohol dehydrogenase; a pyruvate formate lyase; a pyruvate decarboxylase; and combinations thereof.

In certain embodiments of the invention, the arabinose-metabolizing enzyme can be an arabinose transporter (AraT), an arabinose isomerase (AI), a ribulokinanse (RK), and a ribulose 5-phosphate epimerase (R5PE). Cells of the invention may additionally express other enzymes associated with pentose utilization including a xylose isomerase, a transketolase, and a transaldolase or other enzymes of the pentose phosphate pathway.

As a practical matter, whether any polypeptide is at least 70%, 80%, 85%, 90%, 95%, 96%, 97%, 98%, 99% or 100% identical to a polypeptide of the present invention can be determined conventionally using known computer programs. Methods for determining percent identity, as discussed in more detail below in relation to polynucleotide identity, are also relevant for evaluating polypeptide sequence identity.

In some particular embodiments of the invention, amino acid and nucleic acid sequences are readily determined for a gene, protein or other element by an accession number upon consulting the proper database, for example Genebank. However, sequences for exemplary genes and proteins of the present invention are also disclosed herein (SEQ ID NOs: 1-26).

Some embodiments of the invention encompass a polypeptide comprising at least 10, 20, 30, 40, 50, 60, 70, 80, 90, 100, 200, 300, 400, or 500 or more consecutive amino acids of any of SEQ ID NOs: 6-23 & 25, or domains, fragments, variants, or derivatives.

In certain aspects of the invention, the polypeptides and polynucleotides of the present invention are provided in an isolated form, e.g., purified to homogeneity.

The present invention also encompasses polypeptides which comprise, or alternatively consist of, an amino acid sequence which is at least about 80%, 85%, 90%, 95%, 96%, 97%, 98%, 99% similar to the polypeptide of any of SEQ ID NOs: 6-23 & 25 and to portions of such polypeptide with such portion of the polypeptide generally containing at least 30 amino acids and more preferably at least 50 amino acids.

As known in the art "similarity" between two polypeptides is determined by comparing the amino acid sequence and conserved amino acid substitutes thereto of the polypeptide to the sequence of a second polypeptide.

The present invention further relates to a domain, fragment, variant, derivative, or analog of the polypeptide of any of SEQ ID NOs: 6-23 & 25.

Fragments or portions of the polypeptides of the present invention can be employed for producing the corresponding full-length polypeptide by peptide synthesis. Therefore, the fragments can be employed as intermediates for producing the full-length polypeptides.

Fragments of arabinose-metabolizing enzymes of the invention encompass domains, proteolytic fragments, deletion fragments and fragments of any of the genes which retain any specific biological activity of the native enzyme.

The variant, derivative or analog of the polypeptide of arabinose-metabolizing enzymes of the invention may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide for purification of the polypeptide. Such variants, derivatives and analogs are deemed to be within the scope of those skilled in the art from the teachings herein.

The polypeptides of the present invention further include variants of the polypeptides. A "variant" of the polypeptide can be a conservative variant, or an allelic variant. As used herein, a "conservative variant" refers to alterations in the amino acid sequence that do not adversely affect the biological functions of the protein. A substitution, insertion or deletion is said to adversely affect the protein when the altered sequence prevents or disrupts a biological function associated with the protein. For example, the overall charge, structure or hydrophobic-hydrophilic properties of the protein can be altered without adversely affecting a biological activity. Accordingly, the amino acid sequence can be altered, for example to render the peptide more hydrophobic or hydrophilic, without adversely affecting the biological activities of the protein.

An "allelic variant" as used herein, is intended to designate alternate forms of a gene occupying a given locus on a chromosome of an organism. Genes II, Lewin, B., ed., John Wiley & Sons, New York (1985). Non-naturally occurring variants may be produced using art-known mutagenesis techniques. Allelic variants, though possessing a slightly different amino acid sequence than those recited above, will still have the same or similar biological functions associated with the arabinose-metabolizing enzymes of the invention. The allelic variants, the conservative substitution variants, and members of the arabinose-metabolizing enzymes can have an amino acid sequence having at least 75%, at least 80%, at least 90%, at least 95% amino acid sequence identity with the arabinose-metabolizing enzymes of the invention, and, particularly, with the amino acid sequence set forth in any one of SEQ ID NOs: 6-23 & 25. Identity or homology with respect to such sequences is defined herein as the percentage of amino acid residues in the candidate sequence that are identical with the known peptides, after aligning the sequences and introducing gaps, if necessary, to achieve the maximum percent homology, and not considering any conservative substitutions as part of the sequence identity. N-terminal, C-terminal or internal extensions, deletions, or insertions into the peptide sequence shall not be construed as affecting homology.

Thus, in one aspect the proteins and peptides of the present invention include molecules comprising the amino acid sequence of SEQ ID NOs: 6-23 & 25 or fragments thereof having a consecutive sequence of at least about 3, 4, 5, 6, 10, 15, 20, 25, 30, 35 or more amino acid residues of the arabinose transporters (AraT), arabinose isomerase (AI), ribulokinase (RK), or the ribulose 5-phosphate epimerase (R5PE; amino acid sequence variants of such sequences wherein at least one amino acid residue has been inserted N- or C-terminal to, or within, the disclosed sequence; amino acid sequence variants of the disclosed sequences, or their fragments as defined above, that have been substituted by another residue. Contemplated variants further include those containing predetermined mutations by, e.g., homologous recombination, site-directed or PCR mutagenesis, and the corresponding proteins of other species, including, but not limited to bacterial, fungal, and insect.

Using known methods of protein engineering and recombinant DNA technology, variants may be generated to improve or alter the characteristics of the polypeptides encoding the arabinose-metabolizing enzymes. For instance, one or more amino acids can be deleted from the N-terminus or C-terminus of a secreted protein without substantial loss of biological function.

Thus, in another aspect the invention further includes arabinose transporters (AraT), arabinose isomerase (AI), ribulokinase (RK), and ribulose 5-phosphate epimerase (R5PE) polypeptide variants which show substantial biological activity. Such variants include deletions, insertions, inversions, repeats, and substitutions selected according to general rules known in the art so as have little effect on activity.

The skilled artisan is fully aware of amino acid substitutions that are either less likely or not likely to significantly effect protein function (e.g., replacing one aliphatic amino acid with a second aliphatic amino acid), as further described below.

For example, guidance concerning how to make phenotypically silent amino acid substitutions is provided in Bowie et al., "Deciphering the Message in Protein Sequences: Tolerance to Amino Acid Substitutions," *Science* 247:1306-1310 (1990), wherein the authors indicate that there are two main strategies for studying the tolerance of an amino acid sequence to change.

The first strategy exploits the tolerance of amino acid substitutions by natural selection during the process of evolution. By comparing amino acid sequences in different species, conserved amino acids can be identified. These conserved amino acids are likely important for protein function. In contrast, the amino acid positions where substitutions have been tolerated by natural selection indicates that these positions are not critical for protein function. Thus, positions tolerating amino acid substitution could be modified while still maintaining biological activity of the protein.

The second strategy uses genetic engineering to introduce amino acid changes at specific positions of a cloned gene to identify regions critical for protein function. For example, site directed mutagenesis or alanine-scanning mutagenesis (introduction of single alanine mutations at every residue in the molecule) can be used. (Cunningham and Wells, *Science* 244:1081-1085 (1989).) The resulting mutant molecules can then be tested for biological activity.

These two strategies have revealed that proteins are often surprisingly tolerant of amino acid substitutions. The authors further indicate which amino acid changes are likely to be permissive at certain amino acid positions in the protein. For example, most buried (within the tertiary structure of the protein) amino acid residues require nonpolar side chains, whereas few features of surface side chains are generally conserved. Moreover, tolerated conservative amino acid substitutions involve replacement of the aliphatic or hydrophobic amino acids Ala, Val, Leu and Ile; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly.

The terms "derivative" and "analog" refer to a polypeptide differing from the arabinose-metabolizing enzymes of the invention, but retaining essential properties thereof. Generally, derivatives and analogs are overall closely similar, and, in many regions, identical to the arabinose-metabolizing enzymes of the invention. The terms "derived-from", "derivative" and "analog" when referring to arabinose transporters (AraT), arabinose isomerases (AI), ribulokinanses (RK), and ribulose 5-phosphate epimerases (R5PE) of the invention include any polypeptides which retain at least some of the activity of the corresponding native polypeptide, e.g., the arabinose isomerase activity, or the activity of the its catalytic domain.

Derivatives of the arabinose-metabolizing, xylose-metabolizing and cellulase enzymes disclosed herein are polypeptides which may have been altered so as to exhibit features not found on the native polypeptide. Derivatives can be covalently modified by substitution (e.g. amino acid substitution), chemical, enzymatic, or other appropriate means with a moiety other than a naturally occurring amino acid (e.g., a detectable moiety such as an enzyme or radioisotope). Examples of derivatives include fusion proteins, or proteins which are based on a naturally occurring protein sequence, but which have been altered. For example, proteins can be designed by knowledge of a particular amino acid sequence, and/or a particular secondary, tertiary, and/or quaternary structure. Derivatives include proteins that are modified based on the knowledge of a previous sequence, natural or synthetic, which is then optionally modified, often, but not necessarily to confer some improved function. These sequences, or proteins, are then said to be derived from a particular protein or amino acid sequence. In some embodiments of the invention, a derivative must retain at least about 50% identity, at least about 60% identity, at least about 70% identity, at least about 80% identity, at least about 90% identity, at least about 95% identity, at least about 97% identity, or at least about 99% identity to the sequence the derivative is "derived-from." In some embodiments of the invention, an arabinose-metabolizing, xylose-metabolizing or cellulase enzyme is said to be derived-from an enzyme naturally found in a particular species if, using molecular genetic techniques, the DNA sequence for part or all of the enzyme is amplified and placed into a new host cell.

An "analog" is another form of a arabinose transporters (AraT), arabinose isomerase (AI), ribulokinanse (RK), and a ribulose 5-phosphate epimerase (R5PE) polypeptide of the present invention. An analog also retains substantially the same biological function or activity as the polypeptide of interest, e.g., functions as an arabinose isomerase. An analog includes a proprotein which can be activated by cleavage of the proprotein portion to produce an active mature polypeptide.

The polypeptide of the present invention may be a recombinant polypeptide, a natural polypeptide or a synthetic polypeptide. In some particular embodiments, the polypeptide is a recombinant polypeptide.

Combinations of Arabinose-Metabolizing Enzymes

In some embodiments of the present invention, the host cell expresses a combination of heterologous arabinose-metabolizing enzymes. For example, the host cell can contain at least two heterologous arabinose-metabolizing enzymes, at least three heterologous arabinose-metabolizing enzymes, at least four heterologous arabinose-metabolizing enzymes, at least five heterologous arabinose-metabolizing enzymes, at least six heterologous arabinose-metabolizing enzymes, at least seven heterologous arabinose-metabolizing enzymes, or at least eight heterologous arabinose-metabolizing enzymes. The heterologous arabinose-metabolizing enzymes in the host cell can be from the same or from different species (e.g. one from a bacterial species and one from a eukaryotic species). In one embodiment, the one or more heterologous arabinose-metabolizing enzymes are contained in an operon.

Fusion Proteins Comprising Arabinose-Metabolizing Enzymes

The present invention also encompasses fusion proteins. For example, the fusion proteins can be a fusion of a heterologous arabinose-metabolizing enzyme and a second peptide. The heterologous arabinose-metabolizing enzyme and the second peptide can be fused directly or indirectly, for example, through a linker sequence. The fusion protein can comprise for example, a second peptide that is N-terminal to the heterologous arabinose-metabolizing enzyme and/or a second peptide that is C-terminal to the heterologous arabinose-metabolizing enzyme. Thus, in certain embodiments, the polypeptide of the present invention comprises a first polypeptide and a second polypeptide, wherein the first polypeptide comprises a heterologous arabinose-metabolizing enzyme.

According to one aspect of the present invention, the fusion protein can comprise a first and second polypeptide wherein the first polypeptide comprises a heterologous arabinose-metabolizing enzyme and the second polypeptide comprises a signal sequence. According to another embodiment, the fusion protein can comprise a first and second polypeptide, wherein the first polypeptide comprises a heterologous arabinose-metabolizing enzyme and the second polypeptide comprises a polypeptide used to facilitate purification or identification or a reporter peptide. The polypeptide used to facilitate purification or identification or the reporter peptide can be, for example, a HIS-tag, a GST-tag, an HA-tag, a FLAG-tag, or a MYC-tag.

According to another embodiment, the fusion protein can comprise a first and second polypeptide, wherein the first polypeptide comprises a heterologous arabinose-metabolizing enzyme and the second polypeptide comprises a fluorescent protein. In one aspect, the fluorescent protein is used to detect the heterologous arabinose-metabolizing enzyme fusion protein.

According to yet another embodiment, the fusion protein can comprise a first and second polypeptide, wherein the first polypeptide comprises a heterologous arabinose-metabolizing enzyme and the second polypeptide comprises an anchoring peptide.

According to still another embodiment, the fusion protein can comprise a first and second polypeptide, wherein the first polypeptide comprises a heterologous arabinose-metabolizing enzyme and the second polypeptide comprises a cellulose binding module (CBM).

In certain other embodiments, the first polypeptide and the second polypeptide are fused via a linker sequence. The linker sequence can, in some embodiments, be encoded by a codon-optimized polynucleotide. (Codon-optimized polynucleotides are described in more detail below).

Co-Cultures

In another aspect, the present invention is directed to co-cultures comprising at least two host cells wherein the at least two host cells each comprise an isolated polynucleotide encoding a heterologous xylose metabolizing enzyme. In one embodiment, the co-culture can comprise two or more strains of host cells and the heterologous arabinose-utilizing enzymes can be expressed in any combination in the two or more strains of host cells.

The various host cell strains in the co-culture can be present in equal numbers, or one strain or species of host cell can significantly outnumber another second strain or species of host cells. For example, in a co-culture comprising two strains or species of host cells the ratio of one host cell to another can be about 1:1, 1:2, 1:3, 1:4, 1:5, 1:10, 1:100, 1:500 or 1:1000. Similarly, in a co-culture comprising three or more strains or species of host cells, the strains or species of host cells may be present in equal or unequal numbers.

Polynucleotides Encoding Heterologous Arabinose-Metabolizing Enzymes

In another aspect, the present invention includes isolated polynucleotides encoding arabinose-metabolizing enzymes of the present invention. The polynucleotides can encode an arabinose transporter (AraT), arabinose isomerase (AI), ribulokinanse (RK), and/or ribulose 5-phosphate epimerase (R5PE).

The present invention also encompasses an isolated polynucleotide comprising a nucleic acid that is at least about 70%, 75%, or at least about 80% identical, at least about 90% to about 95% identical, or at least about 96%, 97%, 98%, 99% or 100% identical to a nucleic acid encoding an arabinose transporter (AraT), arabinose isomerase (AI), ribulokinanse (RK), and ribulose 5-phosphate epimerase (R5PE).

The present invention also encompasses variants of the arabinose-metabolizing enzyme genes. Variants may contain alterations in the coding regions, non-coding regions, or both. Examples are polynucleotide variants containing alterations which produce silent substitutions, additions, or deletions, but do not alter the properties or activities of the encoded polypeptide. In certain embodiments, nucleotide variants are produced by silent substitutions due to the degeneracy of the genetic code. In further embodiments the arabinose transporter (AraT), arabinose isomerase (AI), ribulokinanse (RK), and ribulose 5-phosphate epimerase (R5PE) polynucleotide variants can be produced for a variety of reasons, e.g., to optimize codon expression for a particular host. Codon-optimized polynucleotides of the present invention are discussed further below.

The present invention also encompasses an isolated polynucleotide encoding a fusion protein. In further embodiments, the first and second polynucleotides are in the same orientation, or the second polynucleotide is in the reverse orientation of the first polynucleotide. In additional embodiments, the first polynucleotide encodes a polypeptide that is either N-terminal or C-terminal to the polypeptide encoded by the second polynucleotide. In certain other embodiments, the first polynucleotide and/or the second polynucleotide are encoded by codon-optimized polynucleotides, for example, polynucleotides codon-optimized for S. cerevisiae.

Also provided in the present invention are allelic variants, orthologs, and/or species homologs. Procedures known in the art can be used to obtain full-length genes, allelic variants, splice variants, full-length coding portions, orthologs, and/or species homologs of genes corresponding to any of SEQ ID NOs: 1-5, or other arabinose-metabolizing enzymes using information from the sequences disclosed herein or the clones deposited with the ATCC or otherwise publically available. For example, allelic variants and/or species homologs may be isolated and identified by making suitable probes or primers from the sequences provided herein and screening a suitable nucleic acid source for allelic variants and/or the desired homolog.

By a nucleic acid having a nucleotide sequence at least, for example, 95% "identical" to a reference nucleotide sequence of the present invention, it is intended that the nucleotide sequence of the nucleic acid is identical to the reference sequence except that the nucleotide sequence may include up to five point mutations per each 100 nucleotides of the reference nucleotide sequence encoding the particular polypeptide. In other words, to obtain a nucleic acid having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. In one embodiment, the query sequence may be an entire sequence shown of any of SEQ ID NOs: 1-5 or any fragment or domain specified as described herein.

As a practical matter, whether any particular nucleic acid molecule or polypeptide is at least 80%, 85%, 90%, 95%, 96%, 97%, 98% or 99% identical to a nucleotide sequence or polypeptide of the present invention can be determined conventionally using known computer programs. A method for determining the best overall match between a query sequence (a sequence of the present invention) and a subject sequence, also referred to as a global sequence alignment, can be determined using the FASTDB computer program based on the algorithm of Brutlag et al. (*Comp. App. Biosci.* (1990) 6:237-245.) In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are to be made for the purposes of the present invention.

Some embodiments of the invention encompass a nucleic acid molecule comprising at least 10, 20, 30, 35, 40, 50, 60, 70, 80, 90, 100, 200, 300, 400, 500, 600, 700, or 800 consecutive nucleotides or more of any of SEQ ID NOs: 1-5, or domains, fragments, variants, or derivatives thereof.

The polynucleotide of the present invention may be in the form of RNA or in the form of DNA, which DNA includes cDNA, genomic DNA, and synthetic DNA. The DNA may be double stranded or single-stranded, and if single stranded can be the coding strand or non-coding (anti-sense) strand. In one embodiment, the coding sequence which encodes the mature polypeptide can be identical to the coding sequence encoding SEQ ID NO: 1-5, or may be a different coding sequence which coding sequence, as a result of the redundancy or degeneracy of the genetic code, encodes the same mature polypeptide as the nucleic acid sequences of any one of SEQ ID NOs: 1-5.

In certain embodiments, the present invention provides an isolated polynucleotide comprising a nucleic acid fragment which encodes at least 10, at least 20, at least 30, at least 40, at least 50, at least 60, at least 70, at least 80, at least 90, at least 95, or at least 100 or more contiguous amino acids of SEQ ID NOs: 6-23 & 25.

The polynucleotide encoding the mature polypeptide of SEQ ID NOs: 6-23 & 25 may include: only the coding sequence for the mature polypeptide; the coding sequence of any domain of the mature polypeptide and the coding sequence for the mature polypeptide (or domain-encoding sequence) together with non coding sequence, such as introns or non-coding sequence 5' and/or 3' of the coding sequence for the mature polypeptide.

Thus, the term "polynucleotide encoding a polypeptide" encompasses a polynucleotide which includes only sequences encoding for the polypeptide as well as a polynucleotide which includes additional coding and/or non-coding sequences.

Due to the degeneracy of the genetic code, one of ordinary skill in the art will immediately recognize that a large portion of the nucleic acid molecules having a sequence at least 90%, 95%, 96%, 97%, 98%, or 99% identical to the nucleic acid sequence of any of SEQ ID NOs: 1-5, or fragments thereof, will encode polypeptides having functional activity. In fact, since degenerate variants of any of these nucleotide sequences encode the same polypeptide, in many instances, this will be clear to the skilled artisan even without performing the above described comparison assay. It will be further recognized in the art that, for such nucleic acid molecules that are not degenerate variants, a reasonable number will also encode a polypeptide having functional activity.

The polynucleotides of the present invention also comprise nucleic acids encoding arabinose-metabolizing enzyme or domain, fragment, variant, or derivative thereof, fused to a polynucleotide encoding a marker sequence which allows for detection of the polynucleotide of the present invention. In one embodiment of the invention, expression of the marker is independent from expression of the arabinose-metabolizing enzyme.

In one embodiment, the one or more polynucleotides of the present invention are stably integrated into the genome of the host cell. In one aspect, the polynucleotides are randomly integrated into the genome of the host cell. In another aspect, multiple copies of polynucleotides are randomly integrated into the genome of the host cell. In one aspect, at least two copies of polynucleotides are randomly integrated into the genome of the host cell.

In another embodiment, the one or more polynucleotides are not integrated into the genome of the host cell. In one aspect, the one or more polynucleotides are present in the host cell in an extra chromosomal plasmid.

In one embodiment, one or more polynucleotides of the present invention are stably integrated at a specific site in the genome of the host cell. In one aspect, the one or more polynucleotides are stably integrated at the site of one or more specific genes in the genome of the host cell. In one embodiment, the one or more specific genes are disrupted as a result of the one or more integration events. In another aspect, the one or more specific genes are deleted as a result of the one or more integration events. In one embodiment, the host cell cannot make the protein product(s) of the one or more specific disrupted genes. In another aspect, the host cell cannot make the protein product(s) of the one or more specific deleted genes. In another embodiment, the one or more polynucleotides are stably integrated at the site of the rDNA in the genome of the host cell.

In one embodiment, the start codon of a polynucleotide of the present invention is integrated in frame with the promoter of a specific gene in the genome of the host cell. In another embodiment, the stop codon of a polynucleotide of the invention is integrated in frame with the terminator of a specific gene in the genome of the host cell. In one embodiment, the start codon of a polynucleotides is integrated in frame with the promoter of a specific gene in the genome of the host cell, and the terminator of the same polynucleotide is also integrated in frame with the terminator of the specific gene.

In one embodiment, the one or more polynucleotides are part of an operon. In one aspect, the start codon of the first polynucleotides in the operon is integrated in frame with the promoter of a specific gene in the genome of the host cell. In another aspect, the stop codon of the last polynucleotides in the operon is integrated in frame with the terminator of a specific gene in the genome of the host cell. In one embodiment, the start codon of the first polynucleotide in the operon is integrated in frame with the promoter of a specific gene in the genome of the host cell, and the stop codon of the last polynucleotide in the operon is integrated in frame with the terminator of the specific gene.

Codon Optimized Polynucleotides

The polynucleotides of the invention can be codon-optimized. As used herein the term "codon-optimized coding region" means a nucleic acid coding region that has been adapted for expression in the cells of a given organism by replacing at least one, or more than one, or a significant number, of codons with one or more codons that are more frequently used in the genes of that organism.

In general, highly expressed genes in an organism are biased towards codons that are recognized by the most abundant tRNA species in that organism. One measure of this bias is the "codon adaptation index" or "CAI." which measures the extent to which the codons used to encode each amino acid in a particular gene are those which occur most frequently in a reference set of highly expressed genes from an organism.

The CAI of codon optimized sequences of the present invention corresponds to between about 0.8 and 1.0, between about 0.8 and 0.9, or about 1.0. A codon optimized sequence may be further modified for expression in a particular organism, depending on that organism's biological constraints. For example, large runs of "As" or "Ts" (e.g., runs greater than 3, 4, 5, 6, 7, 8, 9, or 10 consecutive bases) can be removed from the sequences if these are known to effect transcription negatively. Furthermore, specific restriction enzyme sites may be removed for molecular cloning purposes. Examples of such restriction enzyme sites include PacI, AscI, BamHI, BglII, EcoRI and XhoI. Additionally, the DNA sequence can be checked for direct repeats, inverted repeats and mirror repeats with lengths of ten bases or longer, which can be modified manually by replacing codons with "second best" codons, i.e., codons that occur at the second highest frequency within the particular organism for which the sequence is being optimized.

Deviations in the nucleotide sequence that comprise the codons encoding the amino acids of any polypeptide chain allow for variations in the sequence coding for the gene. Since each codon consists of three nucleotides, and the nucleotides comprising DNA are restricted to four specific bases, there are 64 possible combinations of nucleotides, 61 of which encode amino acids (the remaining three codons encode signals ending translation). The "genetic code" which shows which codons encode which amino acids is reproduced herein as Table 4. As a result, many amino acids are designated by more than one codon. For example, the amino acids alanine and proline are coded for by four triplets, serine and arginine by six, whereas tryptophan and methionine are coded by just one triplet. This degeneracy allows for DNA base composition to vary over a wide range without altering the amino acid sequence of the proteins encoded by the DNA.

TABLE 4

The Standard Genetic Code

| | T | C | A | G |
|---|---|---|---|---|
| T | TTT Phe (F) | TCT Ser (S) | TAT Tyr (Y) | TGT Cys (C) |
| | TTC " | TCC " | TAC " | TGC " |
| | TTA Leu (L) | TCA " | TAA Ter | TGA Ter |
| | TTG " | TCG " | TAG Ter | TGG Trp (W) |
| C | CTT Leu (L) | CCT Pro (P) | CAT His (H) | CGT Arg (R) |
| | CTC " | CCC " | CAC " | CGC " |
| | CTA " | CCA " | CAA Gln (Q) | CGA " |
| | CTG " | CCC " | CAG " | CCC " |
| A | ATT Ile (I) | ACT Thr (T) | AAT Asn (N) | AGT Ser (S) |
| | ATC " | ACC " | AAC " | AGC " |
| | ATA " | ACA " | AAA Lys (K) | AGA Arg (R) |
| | ATG Met (M) | ACG " | AAG " | AGG " |
| G | GTT Val (V) | GCT Ala (A) | GAT Asp (D) | GGT Gly (G) |
| | CTC " | GCC " | GAC " | GGC " |
| | GTA " | GCA " | GAA Glu (E) | GGA " |
| | GTG " | GCG " | GAG " | GGG " |

Many organisms display a bias for use of particular codons to code for insertion of a particular amino acid in a growing peptide chain. Codon preference or codon bias, differences in codon usage between organisms, is afforded by degeneracy of the genetic code, and is well documented among many organisms. Codon bias often correlates with the efficiency of translation of messenger RNA (mRNA), which is in turn believed to be dependent on, inter alia, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

Given the large number of gene sequences available for a wide variety of animal, plant and microbial species, it is possible to calculate the relative frequencies of codon usage. Codon usage tables are readily available, for example, at http://www.kazusa.or.jp/codon/ (visited Oct. 5, 2011), and these tables can be adapted in a number of ways. See Nakamura, Y., et al. "Codon usage tabulated from the international DNA sequence databases: status for the year 2000," *Nucl. Acids Res.* 28:292 (2000). Codon usage tables for yeast, calculated from GenBank Release 128.0 [15 Feb. 2002], are reproduced below as Table 5. This table uses mRNA nomenclature, and so instead of thymine (T) which is found in DNA, the table uses uracil (U) which is found in RNA. The table has been adapted so that frequencies are calculated for each amino acid, rather than for all 64 codons.

TABLE 5

Codon Usage Table for *Saccharomyces cerevisiae* Genes

| Amino Acid | Codon | Number | Frequency per hundred |
|---|---|---|---|
| Phe | UUU | 170666 | 26.1 |
| Phe | UUC | 120510 | 18.4 |
| Leu | UUA | 170884 | 26.2 |
| Leu | UUG | 177573 | 27.2 |
| Leu | CUU | 80076 | 12.3 |
| Leu | CUC | 35545 | 5.4 |
| Leu | CUA | 87619 | 13.4 |
| Leu | CUG | 68494 | 10.5 |
| Ile | AUU | 196893 | 30.1 |
| Ile | AUC | 112176 | 17.2 |
| Ile | AUA | 116254 | 17.8 |
| Met | AUG | 136805 | 20.9 |
| Val | GUU | 144243 | 22.1 |
| Val | GUC | 76947 | 11.8 |
| Val | GUA | 76927 | 11.8 |
| Val | GUG | 70337 | 10.8 |
| Ser | UCU | 153557 | 23.5 |
| Ser | UCC | 92923 | 14.2 |
| Ser | UCA | 122028 | 18.7 |
| Ser | UCG | 55951 | 8.6 |
| Ser | AGU | 92466 | 14.2 |
| Ser | AGC | 63726 | 9.8 |
| Pro | CCU | 88263 | 13.5 |
| Pro | CCC | 44309 | 6.8 |
| Pro | CCA | 119641 | 18.3 |
| Pro | CCG | 34597 | 5.3 |
| Thr | ACU | 132522 | 20.3 |
| Thr | ACC | 83207 | 12.7 |
| Thr | ACA | 116084 | 17.8 |
| Thr | ACG | 52045 | 8.0 |
| Ala | GCU | 138358 | 21.2 |
| Ala | GCC | 82357 | 12.6 |
| Ala | GCA | 105910 | 16.2 |
| Ala | GCG | 40358 | 6.2 |
| Tyr | UAU | 122728 | 18.8 |
| Tyr | UAC | 96596 | 14.8 |
| His | CAU | 89007 | 13.6 |
| His | CAC | 50785 | 7.8 |
| Gln | CAA | 178251 | 27.3 |
| Gln | CAG | 79121 | 12.1 |
| Asn | AAU | 233124 | 35.7 |
| Asn | AAC | 162199 | 24.8 |
| Lys | AAA | 273618 | 41.9 |
| Lys | AAG | 201361 | 30.8 |
| Asp | GAU | 245641 | 37.6 |
| Asp | GAC | 132048 | 20.2 |
| Glu | GAA | 297944 | 45.6 |
| Glu | GAG | 125717 | 19.2 |
| Cys | UGU | 52903 | 8.1 |
| Cys | UGC | 31095 | 4.8 |
| Trp | UGG | 67789 | 10.4 |
| Arg | CGU | 41791 | 6.4 |
| Arg | CGC | 16993 | 2.6 |
| Arg | CGA | 19562 | 3.0 |
| Arg | CGG | 11351 | 1.7 |
| Arg | AGA | 139081 | 21.3 |
| Arg | AGG | 60289 | 9.2 |
| Gly | GGU | 156109 | 23.9 |
| Gly | GGC | 63903 | 9.8 |
| Gly | GGA | 71216 | 10.9 |
| Gly | GGG | 39359 | 6.0 |
| Stop | UAA | 6913 | 1.1 |
| Stop | UAG | 3312 | 0.5 |
| Stop | UGA | 4447 | 0.7 |

By utilizing this or similar tables, one of ordinary skill in the art can apply the frequencies to any given polypeptide sequence, and produce a nucleic acid fragment of a codon-optimized coding region which encodes the polypeptide, but which uses codons optimal for a given species. Codon-optimized coding regions can be designed by various different methods.

In one method, a codon usage table is used to find the single most frequent codon used for any given amino acid, and that codon is used each time that particular amino acid appears in the polypeptide sequence. For example, referring to Table 5 above, for leucine, the most frequent codon is UUG, which is used 27.2% of the time. Thus all the leucine residues in a given amino acid sequence would be assigned the codon UUG.

In another method, the actual frequencies of the codons are distributed randomly throughout the coding sequence. Thus, using this method for optimization, if a hypothetical polypeptide sequence had 100 leucine residues, referring to Table 5 for frequency of usage in the *S. cerevisiae*, about 5, or 5% of the leucine codons would be CUC, about 11, or 11% of the leucine codons would be CUG, about 12, or 12% of the leucine codons would be CUU, about 13, or 13% of the leucine codons would be CUA, about 26, or 26% of the leucine codons would be UUA, and about 27, or 27% of the leucine codons would be UUG.

These frequencies would be distributed randomly throughout the leucine codons in the coding region encoding the hypothetical polypeptide. As will be understood by those of ordinary skill in the art, the distribution of codons in the sequence can vary significantly using this method; however, the sequence always encodes the same polypeptide.

When using the methods above, the term "about" is used precisely to account for fractional percentages of codon frequencies for a given amino acid. As used herein, "about" is defined as one amino acid more or one amino acid less than the value given. The whole number value of amino acids is rounded up if the fractional frequency of usage is 0.50 or greater, and is rounded down if the fractional frequency of use is 0.49 or less. Using again the example of the frequency of usage of leucine in human genes for a hypothetical polypeptide having 62 leucine residues, the fractional frequency of codon usage would be calculated by multiplying 62 by the frequencies for the various codons. Thus, 7.28 percent of 62 equals 4.51 UUA codons, or "about 5," i.e., 4, 5, or 6 UUA codons, 12.66 percent of 62 equals 7.85 UUG codons or "about 8," i.e., 7, 8, or 9 UUG codons, 12.87 percent of 62 equals 7.98 CUU codons, or "about 8," i.e., 7, 8, or 9 CUU codons, 19.56 percent of 62 equals 12.13 CUC codons or "about 12," i.e., 11, 12, or 13 CUC codons, 7.00 percent of 62 equals 4.34 CUA codons or "about 4," i.e., 3, 4, or 5 CUA codons, and 40.62 percent of 62 equals 25.19 CUG codons, or "about 25," i.e., 24, 25, or 26 CUG codons.

Randomly assigning codons at an optimized frequency to encode a given polypeptide sequence, can be done manually by calculating codon frequencies for each amino acid, and then assigning the codons to the polypeptide sequence randomly. Additionally, various algorithms and computer software programs are readily available to those of ordinary skill in the art. For example, the "FEditSeq" function in the Lasergene Package, available from DNAstar, Inc., Madison, Wis., the backtranslation function in the VectorNTI Suite, available from InforMax, Inc., Bethesda, Md., and the "backtranslate" function in the GCG—Wisconsin Package, available from Accelrys, Inc., San Diego, Calif. In addition, various resources are publicly available to codon-optimize coding region sequences, e.g., the "backtranslation" function at http://www.entelechon.com/bioinformatics/backtranslation.php?lang=eng (visited Dec. 18, 2009) and the "backtranseq" function available at http://emboss.bioinformatics.nl/cgi-bin/emboss/backtranseq (visited Oct. 5, 2011). Constructing a rudimentary algorithm to assign codons based on a given frequency can also easily be accomplished with basic mathematical functions by one of ordinary skill in the art.

A number of options are available for synthesizing codon optimized coding regions designed by any of the methods described above, using standard and routine molecular biological manipulations well known to those of ordinary skill in the art. In one approach, a series of complementary oligonucleotide pairs of 80-90 nucleotides each in length and spanning the length of the desired sequence is synthesized by standard methods. These oligonucleotide pairs are synthesized such that upon annealing, they form double stranded fragments of 80-90 base pairs, containing cohesive ends, e.g., each oligonucleotide in the pair is synthesized to extend 3, 4, 5, 6, 7, 8, 9, 10, or more bases beyond the region that is complementary to the other oligonucleotide in the pair. The single-stranded ends of each pair of oligonucleotides is designed to anneal with the single-stranded end of another pair of oligonucleotides. The oligonucleotide pairs are allowed to anneal, and approximately five to six of these double-stranded fragments are then allowed to anneal together via the cohesive single stranded ends, and then they ligated together and cloned into a standard bacterial cloning vector, for example, a TOPO® vector available from Invitrogen Corporation, Carlsbad, Calif. The construct is then sequenced by standard methods. Several of these constructs consisting of 5 to 6 fragments of 80 to 90 base pair fragments ligated together, i.e., fragments of about 500 base pairs, are prepared, such that the entire desired sequence is represented in a series of plasmid constructs. The inserts of these plasmids are then cut with appropriate restriction enzymes and ligated together to form the final construct. The final construct is then cloned into a standard bacterial cloning vector, and sequenced. Additional methods would be immediately apparent to the skilled artisan. In addition, gene synthesis is readily available commercially.

In additional embodiments, a full-length polypeptide sequence is codon-optimized for a given species resulting in a codon-optimized coding region encoding the entire polypeptide, and then nucleic acid fragments of the codon-optimized coding region, which encode fragments, variants, and derivatives of the polypeptide are made from the original codon-optimized coding region. As would be well understood by those of ordinary skill in the art, if codons have been randomly assigned to the full-length coding region based on their frequency of use in a given species, nucleic acid fragments encoding fragments, variants, and derivatives would not necessarily be fully codon optimized for the given species. However, such sequences are still much closer to the codon usage of the desired species than the native codon usage. The advantage of this approach is that synthesizing codon-optimized nucleic acid fragments encoding each fragment, variant, and derivative of a given polypeptide, although routine would be time consuming and would result in significant expense.

The codon-optimized coding regions can be, for example, versions encoding a xylose or arabinose metabolizing enzymes of the invention, or domains, fragments, variants, or derivatives thereof.

Codon optimization is carried out for a particular species by methods described herein, for example, in certain embodiments, codon-optimized coding regions encoding polypeptides disclosed in the present application or domains, fragments, variants, or derivatives thereof are optimized according to codon usage in yeast (e.g. *Saccharomyces cerevisiae*). In certain embodiments described herein, a codon-optimized coding region encoding any of SEQ ID NOs: 1-5 or domain, fragment, variant, or derivative thereof, is optimized according to codon usage in yeast (e.g. *Saccharomyces cerevisiae*). In some embodiments, the sequences are codon-optimized specifically for expression in *Saccharomyces cerevisiae*. Alternatively, a codon-optimized coding region encoding any of SEQ ID NOs: 1-5 may be optimized according to codon usage in any plant, animal, or microbial species.

Also provided are polynucleotides, vectors, and other expression constructs comprising codon-optimized coding regions encoding polypeptides disclosed herein, or domains, fragments, variants, or derivatives thereof, and various methods of using such polynucleotides, vectors and other expression constructs.

Vectors and Methods of Using Vectors in Host Cells

In another aspect, the present invention relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

The polynucleotides of the present invention can be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; and yeast plasmids. However, any other vector may be used as long as it is replicable and viable in the host.

The appropriate DNA sequence can be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively associated with an appropriate expression control sequence(s) (promoter) to direct mRNA synthesis. Any suitable promoter to drive gene expression in the host cells of the invention may be used.

In addition, the expression vectors may contain one or more selectable marker genes to provide a phenotypic trait for selection of transformed host cells such as URA3, HIS3, LEU2, TRP1, LYS2 or ADE2, dihydrofolate reductase, neomycin (G418) resistance or zeocin resistance for eukaryotic cell culture, or tetracycline or ampicillin resistance in prokaryotic cell culture, e.g., *Clostridium thermocellum*.

The expression vector may also contain a ribosome binding site for translation initiation and/or a transcription terminator. The vector may also include appropriate sequences for amplifying expression, or may include additional regulatory regions.

The vector containing the appropriate DNA sequence as herein, as well as an appropriate promoter or control sequence, may be employed to transform an appropriate host to permit the host to express the protein.

Thus, in certain aspects, the present invention relates to host cells containing the above-described constructs. The host cell can be a host cell as described elsewhere in the application. The host cell can be, for example, a lower eukaryotic cell, such as a yeast cell, e.g., *Saccharomyces cerevisiae* or *Kluyveromyces*, or the host cell can be a prokaryotic cell, such as a bacterial cell. e.g., *Clostridium thermocellum*.

The selection of an appropriate host is deemed to be within the scope of those skilled in the art from the teachings herein. In one embodiment, the vector is integrated into the genome of the host cell. In another embodiment, the vector is present in the host cell as an extrachromosomal plasmid.

To select for foreign DNA that has entered a host it is preferable that the DNA be stably maintained in the organism of interest. With regard to plasmids, there are two processes by which this can occur. One is through the use of replicative plasmids. These plasmids have origins of replication that are recognized by the host and allow the plasmids to replicate as stable, autonomous, extra chromosomal elements that are partitioned during cell division into daughter cells. The second process occurs through the integration of a plasmid onto the chromosome. This predominately happens by homologous recombination and results in the insertion of the entire plasmid, or parts of the plasmid, into the host chromosome. Thus, the plasmid and selectable marker(s) are replicated as an integral piece of the chromosome and segregated into daughter cells. Therefore, to ascertain if plasmid DNA is entering a cell during a transformation event through the use of selectable markers requires the use of a replicative plasmid or the ability to recombine the plasmid onto the chromosome. These qualifiers cannot always be met, especially when handling organisms that do not have a suite of genetic tools.

One way to avoid issues regarding plasmid-associated markers is through the use of transposons. A transposon is a mobile DNA element, defined by mosaic DNA sequences that are recognized by enzymatic machinery referred to as a transposase. The function of the transposase is to randomly insert the transposon DNA into host or target DNA. A selectable marker can be cloned onto a transposon by standard genetic engineering. The resulting DNA fragment can be coupled to the transposase machinery in an in vitro reaction and the complex can be introduced into target cells by electroporation. Stable insertion of the marker onto the chromosome requires only the function of the transposase machinery and alleviates the need for homologous recombination or replicative plasmids.

The random nature associated with the integration of transposons has the added advantage of acting as a form of mutagenesis. Libraries can be created that comprise amalgamations of transposon mutants. These libraries can be used in screens or selections to produce mutants with desired phenotypes. For instance, a transposon library of a CBP organism could be screened for the ability to produce less ethanol, or more lactic acid and/or more acetate.

Methods of Using Host Cells to Produce Ethanol or Other Fermentation Products

Microorganisms produce a diverse array of fermentation products, including organic acids, such as lactate (the salt form of lactic acid), acetate (the salt form of acetic acid), pyruvate, succinate, and butyrate, and neutral products, such as ethanol, butanol, acetone, and butanediol. End products of fermentation share to varying degrees several fundamental features, including: they are relatively nontoxic under the conditions in which they are initially produced, but become more toxic upon accumulation.

In one aspect, the present invention is directed to use of host cells and co-cultures to produce ethanol or other products from the xylose and/or the arabinose portion of lignocellulosic substrates. Such methods can be accomplished, for example, by contacting a pentose-containing lignocellulosic substrate with a host cell or a co-culture of the present invention. Fermentation products include, but are not limited to products such as ethanol, propanol, isoamyl alcohol, butanol, acetate, amino acids, and vitamins.

In one embodiment, the end products of pentose fermentation by the host strain comprise pyruvate, acetate, and ethanol. In another embodiment, the end products of pentose fermentation by the host strain comprise acetate, and ethanol. In one aspect, the ratio of acetate to ethanol formed can be at least about 10:1, at least about 5:1, at least about 2:1, at least about 1:1, at least about 1:2, at least about 1:5, or at least about 1:10. In one embodiment, the host cell is further engineered in order to increase ethanol production from pentose fermentation by the host cell. In one embodiment, the PTA gene is deleted in order to increase ethanol production from pentose fermentation by the host cell. In one aspect, the deletion of the PTA gene results in ethanol being the major end product of xylose fermentation by the host cell. In another aspect, the deletion of the PTA gene results in ethanol being the only end product of pentose fermentation by the host cell.

The production of ethanol can, according to the present invention, be performed at temperatures of at least about 25° C., about 28° C., about 30° C., about 31° C., about 32° C., about 33° C., about 34° C., about 35° C., about 36° C., about 37° C., about 38° C. about 39° C., about 40° C., about 41° C., about 42° C., or about 50° C. In some embodiments of the present invention, the thermotolerant host cell can produce ethanol from an arabinose-containing cellulosic substrate at temperatures above about 30° C., about 31° C., about 32° C., about 33° C., about 34° C., about 35° C., about 36° C., about 37° C., about 38° C., about 39° C., about 40° C., about 41° C., about 42° C., or about 50° C. In some embodiments of the present invention, the thermotolerant host cell can produce ethanol from an arabinose-containing cellulosic substrate at temperatures from about 30° C. to 60° C., about 30° C. to 55° C., about 30° C. to 50° C., about 40° C. to 60° C. about 40° C. to 55° C. or about 40° C. to 50° C.

In some embodiments, methods of producing ethanol can comprise contacting an arabinose-containing lignocellulosic substrate with a host cell or co-culture of the invention and additionally contacting the arabinose-containing lignocellulosic substrate with externally produced arabinose-metabolizing enzymes. Exemplary externally produced arabinose metabolizing enzymes are commercially available and are known to those of skill in the art.

The invention is also directed to methods of reducing the amount of externally produced arabinose-metabolizing enzymes required to produce a given amount of ethanol from a arabinose-containing cellulosic substrate comprising contacting the arabinose-containing cellulosic substrate with externally produced arabinose-metabolizing enzymes and with a host cell or co-culture of the invention. In some embodiments, the same amount of ethanol production can be achieved using at least about 5%, 10%, 15%, 20%, 25%, 30%, or 50% fewer externally produced arabinose-metabolizing enzymes. In other embodiments, ethanol production can be achieved without the addition of externally produced arabinose-metabolizing enzymes.

In some embodiments, the methods comprise producing ethanol at a particular rate. For example, in some embodiments, ethanol is produced at a rate of at least about 0.1 mg per hour per liter, at least about 0.25 mg per hour per liter, at least about 0.5 mg per hour per liter, at least about 0.75 mg per hour per liter, at least about 1.0 mg per hour per liter, at least about 2.0 mg per hour per liter, at least about 5.0 mg per hour per liter, at least about 10 mg per hour per liter, at least about 15 mg per hour per liter, at least about 20.0 mg per hour per liter, at least about 25 mg per hour per liter, at least about 30 mg per hour per liter, at least about 50 mg per hour per liter, at least about 100 mg per hour per liter, at least about 200 mg per hour per liter, or at least about 500 mg per hour per liter.

In some embodiments, the host cells of the present invention can produce ethanol at a rate of at least about 0.1 mg per hour per liter, at least about 0.25 mg per hour per liter, at least about 0.5 mg per hour per liter, at least about 0.75 mg per hour per liter, at least about 1.0 mg per hour per liter, at least about 2.0 mg per hour per liter, at least about 5.0 mg per hour per liter, at least about 10 mg per hour per liter, at least about 15 mg per hour per liter, at least about 20.0 mg per hour per liter, at least about 25 mg per hour per liter, at least about 30 mg per hour per liter, at least about 50 mg per hour per liter, at least about 100 mg per hour per liter, at least about 200 mg per hour per liter, or at least about 500 mg per hour per liter more than a control strain (lacking heterologous arabinose-metabolizing enzymes) and grown under the same conditions. In some embodiments, the ethanol can be produced in the absence of any externally added arabinose-metabolizing enzymes.

In some embodiments, a recombinant eukaryotic host cell of the invention produces an ethanol yield of at least about 5, at least about 7, at least about 10, at least about 13, at least about 15, or at least about 20 g/l ethanol after 24 hours of fermentation from a medium containing 20 g/l xylose and 21 g/l arabinose. In some embodiments, a recombinant eukaryotic host cell of the invention produces an ethanol yield of at least about 10, at least about 13, at least about 15, or at least about 20 g/l ethanol after 24 hours of fermentation from a medium containing 20 g/l glucose and 21 g/l arabinose. In some embodiments, a recombinant eukaryotic host cell of the invention produces an ethanol yield of at least about 10, at least about 13, at least about 15, or at least about 20 g/l ethanol after 24 hours of fermentation from a medium containing 10 g/l glucose, 10 g/l xylose and 21 g/l arabinose.

In some embodiments, organisms of the invention produce between about 5 and about 50, about 10 and about 50, about 20 and about 50, about 30 and about 50 g/l of ethanol after 24 hours of fermentation on arabinose-containing feedstock. In some embodiments, organisms of the invention produce between about 10 and about 50, about 15 and about 50, about 20 and about 50, about 25 and about 50, about 30 and about 50, about 35 and about 50 g/l of ethanol after 24 hours of fermentation on arabinose-containing feedstock. In some embodiments, the arabinose-containing feedstock contains about 2%, about 5%, about 10%, about 15%, about 20%, about 50%, or about 100% arabinose.

In some embodiments, cells of the invention are able to take up at least about 2, at least about 3, at least about 4, at least about 5, at least about 6 or at least about 7 g/l of arabinose from the external environment to the intracellular space per 24 hours. In some embodiments, cells of the invention are able to take up at least about 2, at least about 3, at least about 4, at least about 5, at least about 6 or at least about 7 g/l of arabinose from the external environment to the intracellular space per 72 hours.

In some embodiments, cells of the invention are able to take up at least about 0.1 nmol mg dry mass$^{-1}$ min$^{-1}$, about 0.2 nmol mg dry mass$^{-1}$ min$^{-1}$, about 0.3 nmol mg dry mass$^{-1}$ min$^{-1}$, about 0.4 nmol mg dry mass$^{-1}$ min$^{-1}$, about 0.6 nmol mg dry mass$^{-1}$ min$^{-1}$, about 0.8 nmol mg dry mass$^{-1}$ min$^{-1}$, about 1.0 nmol mg dry mass$^{-1}$ min$^{-1}$, about 1.5 nmol mg dry mass$^{-1}$ min$^{-1}$, about 2 nmol mg dry mass$^{-1}$ min$^{-1}$, about 3 nmol mg dry mass$^{-1}$ min$^{-1}$, about 5 nmol mg dry mass$^{-1}$ min$^{-1}$, about 7 nmol mg dry mass$^{-1}$ min$^{-1}$, or at least about 10 nmol mg dry mass$^{-1}$ min$^{-1}$ of arabinose.

Ethanol production can be measured using any method known in the art. For example, the quantity of ethanol in fermentation samples can be assessed using HPLC analysis. Many ethanol assay kits are commercially available that use, for example, alcohol oxidase enzyme based assays. Methods of determining ethanol production are within the scope of those skilled in the art from the teachings herein.

The U.S. Department of Energy (DOE) provides a method for calculating theoretical ethanol yield. Accordingly, if the weight percentages are known of C6 sugars (i.e., glucan, galactan, mannan), the theoretical yield of ethanol in gallons per dry ton of total C6 polymers can be determined by applying a conversion factor as follows:

> (1.11 pounds of C6 sugar/pound of polymeric sugar)×(0.51 pounds of ethanol/pound of sugar)×(2000 pounds of ethanol/ton of C6 polymeric sugar)×(1 gallon of ethanol/6.55 pounds of ethanol)×(1/100%), wherein the factor (1 gallon of ethanol/6.55 pounds of ethanol) is taken as the specific gravity of ethanol at 20° C.

And if the weight percentages are known of C5 sugars (i.e., xylan, arabinan), the theoretical yield of ethanol in gallons per dry ton of total C5 polymers can be determined by applying a conversion factor as follows:

> (1.136 pounds of C5 sugar/pound of C5 polymeric sugar)×(0.51 pounds of ethanol/pound of sugar)×(2000 pounds of ethanol/ton of C5 polymeric sugar)×(1 gallon of ethanol/6.55 pounds of ethanol)×(1/100%), wherein the factor (1 gallon of ethanol/6.55 pounds of ethanol) is taken as the specific gravity of ethanol at 20° C.

It follows that by adding the theoretical yield of ethanol in gallons per dry ton of the total C6 polymers to the theoretical yield of ethanol in gallons per dry ton of the total C5 polymers gives the total theoretical yield of ethanol in gallons per dry ton of feedstock.

EXAMPLES

Identification of Potential Arabinose Transporters

Figure 1:
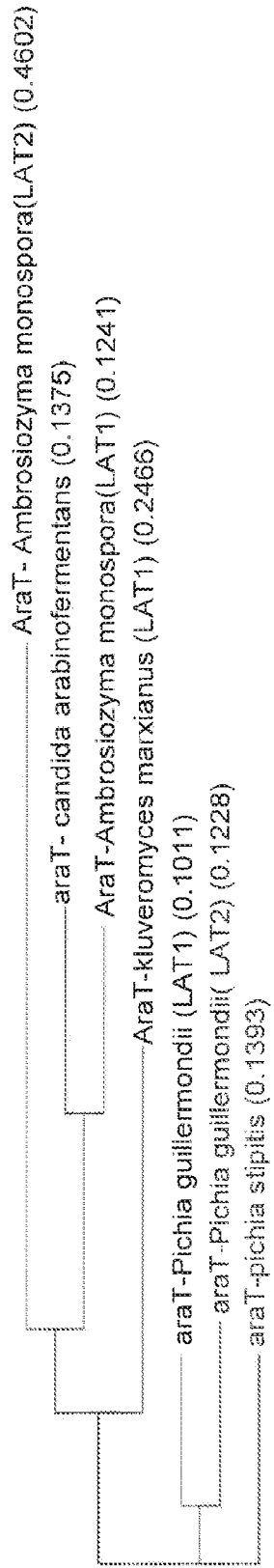
FIG. 1 depicts a phylogenetic representation of the similarity of protein sequences with arabinose transporter activity.
Figure 2:
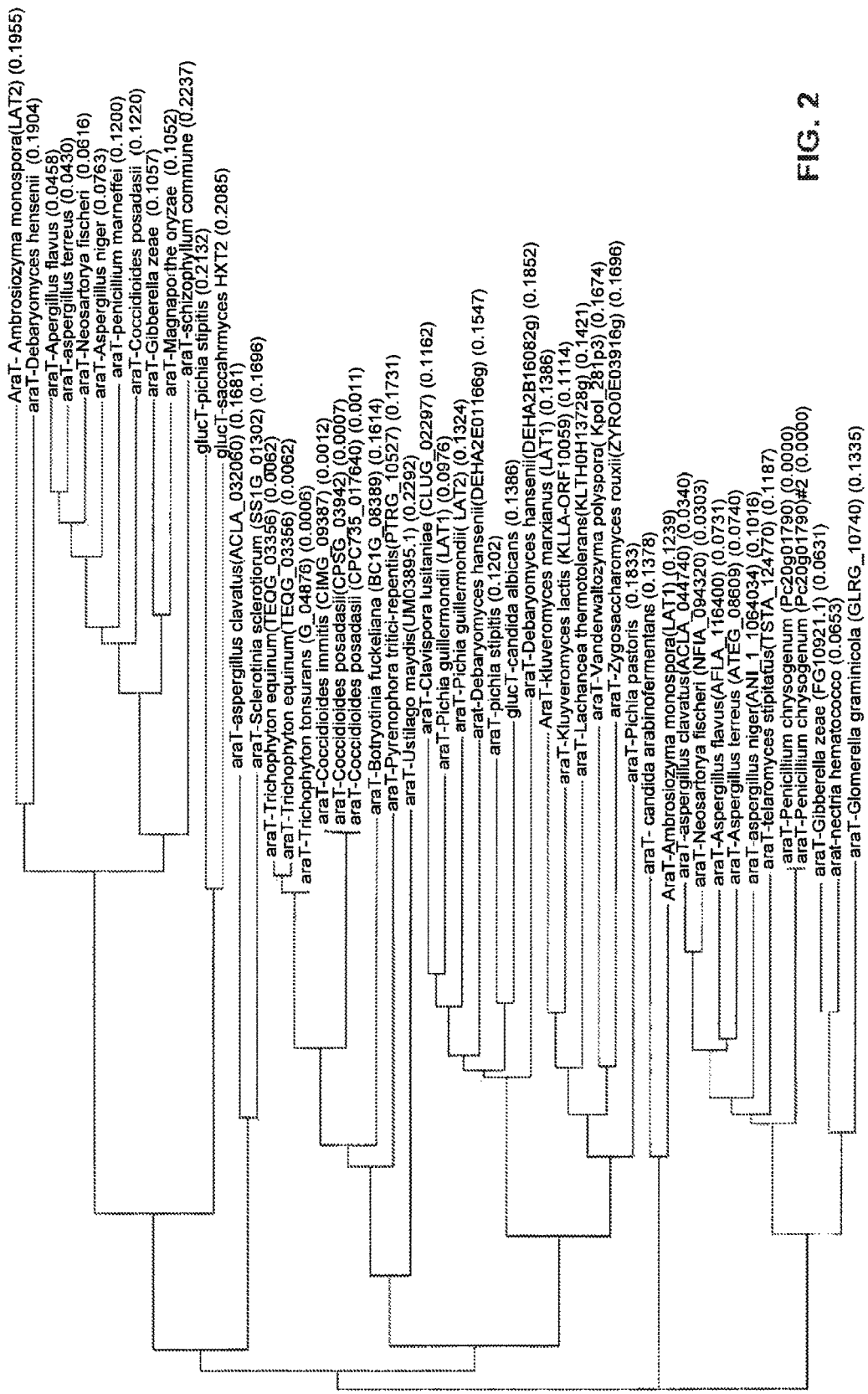
FIG. 2 depicts a phylogenetic representation of the similarity of protein sequences with possible arabinose transporter activity.

There are seven putative Arabinose transporters in the public and patent literature. The sequences of these seven proteins were aligned and determined to have only 10% identity with each other (FIG. 1). This indicates arabinose transport function may be encoded by a divergent set of enzymes. To identify potential arabinose transporters several of these published transporters were blasted against the fungal protein database. The phylogenetic relationship of the top 7-10 hits from these blasts is shown in FIG. 2. From this analysis, 15 enzymes were cloned into expression vectors and transformed into *S. cerevisiae*.

Arabinose Uptake Assay

To assay arabinose uptake an HPLC based assay was developed. Plasmid containing strains expressing arabinose transporters were grown overnight in YNB-uracil to maintain selection of the plasmid. These overnight cultures were subsequently diluted to normalize the optical density to OD1. From these, dilutions, 1 ML of culture was spun down and washed 2× in distilled H20. Following these washes, 50 ul of assay buffer (20 gl1 arabinose and 10 g/l glucose dissolved in $H_2O$) was added. After 72 hrs, 10 ul aliquots of these reactions were prepped for HPLC with dilution into 85 ul $H_2O$ and 5 ul 10% sulfuric acid. Results of this assay are shown in FIG. 3. Most of the transporters selected appeared to function with the exception of the protein selected from Z. rouxii. The protein from K. thermotolerans appears to function better than the three other transporters tested.

Strain Construction and Fermentation Analysis

The base S. cerevisiae strain used to demonstrate arabinose utilization was M2874 which contains upregulation—by containing multiple copies—of the pentose phosphate pathway genes (TAL1, TKL1 and RKI1), a deletion of GRE3 and multiple copies of XI and XKS. This strain has been shown to efficiently convert xylose to ethanol. To engineer M2874 with the arabinose pathway, an integration into S. cerevisiae rDNA sites was designed. A schematic illustrating the genomic integration design strategy known as arabinose assembly 1 (AA1) is indicated in FIG. 4. To create this assembly, purified PCR products amplified using primers listed in Table 3 were generated (FIG. 5) and transformed into M2874 (M2874+ara). As a control, a separate transformation was performed without addition of AA1 amplicons (M2874--noDNA). Both transformations were plated on YMA (yeast nitrogen base plus 20 g/l arabinose). After 48 hours of incubation several hundred colonies were clearly visible on the plates containing M2874+ara and zero colonies were observed on the no-DNA control (FIG. 6).

To confirm M2874+ara strains were able to convert arabinose into ethanol, several fermentations were conducted using either M2874 or a single colony isolated from the M2874+ara plate. Fermentations were run in 50 mls of medium which had been added to sealed aerobic pressure bottles.

TABLE 3

Primers used to amplify components of the arabinose-utilization construct.

| promoter/gene | Primer combination | Template 1 | Template 2 | Template 3 |
|---|---|---|---|---|
| ADHp/PDCt | X16757/ X17758 | pMU2712 (araA) | pMU2713 (araB) | pMU2714 (araD) |
| HXT7p/PMA1t | X16759/ X16760 | pMU2715 (araA) | pMU2716 (araB) | pMU2717 (araD) |
| TPIp/FBAt | X16761/ X16762 | pMU2718 (araA) | pMU2719 (araB) | pMU2720 (araD) |
| ENOp/ENOt | X16763/ X16764 | pMU3053 | pMU3118 | |
| rDNA 5' flank | X13185/ X13186 | M2390 genomic DNA | | |
| rDNA 3' flank | X13187/ X13188 | M2390 genomic DNA | | |

To create pMU2712, pMU2713 and pMU2714 the B. thetaiotamicron araA, araB and araD were cloned into a vector containing the S. cerevisiae ADH1 promoter and PDC1 terminator. To create pMU2715, pMU2716, and pMU2717 the B. thetaiotamicron araA, araB and araD were cloned into a vector containing the S. cerevisiae HXT7p promoter and PMA1 terminator. To create pMU2718, pMU2719, and pMU2720 the B. thetaiotamicron araA, araB and araD were cloned into a vector containing the S. cerevisiae TPI1 promoter and FBA1 terminator. To create pMU3053 and pMU3118, the K. lactis and K. thermotolerans AraT were cloned into a vector containing the ENO1 promoter and the ENO1 terminator.

Growth on Arabinose as the Sole Carbon Source (YP-21 g/l Arabinose)

The ability of the stain M2874 to convert arabinose into ethanol via fermentation was tested. ~9 g/l of arabinose was converted into ~4.0 g/l of ethanol in 48 hours. The parent strain is unable to consume any arabinose and no ethanol accumulation was observed.

Fermentation Analysis

To confirm M2874+ara strains were able to convert Arabinose into ethanol, several fermentations were conducted using either M2874 or a single colony isolated from the M2874+ara plate. M2874 and M2874+ara were grown up overnight to prepare the inoculums. Each strain was adjusted to an OD of 1.0 of which 100 ul was added to fermentation medium. Fermentations were run in sealed aerobic pressure bottles containing 50 mls of YP-medium containing either arabinose or a mixture of arabinose and xylose and/or glucose.

Growth on Arabinose as the Sole Carbon Source

FIG. 7 shows that M2874 is able to convert ~9 g/l of arabinose into ~4.0 g/l of ethanol in 48 hours, giving a yield of 0.44 g/ethanol per g/arabinose consumed in a medium containing YP-21 g/l arabinose. The parent strain was unable to consume any arabinose and no ethanol accumulation was observed.

Growth on Arabinose and Xylose as the Sole Carbon Sources

FIG. 8 shows that both M2874 and M2874+ara are able to consume all 20 grams of xylose by 48 hours when grown on YP-20 g/xylose/21 g/l arabinose. However, only M2874+ara is able to use arabinose, resulting in an extra 3.5 g/l ethanol from the ~7 g/l which was consumed, yielding ~0.5 g ethanol per gram of arabinose consumed.

Growth on Arabinose and Glucose

FIG. 9 shows that both M2874 and M2874+ara are able to consume all 20 g/l glucose by 48 hours when grown on YP-20 g/l glucose/21 g/l arabinose media. However, only M2874+ara was able to use arabinose, resulting in an extra 6.5 g/l ethanol from the ~13 g/l arabinose consumed, which yielded 0.5 g ethanol per gram of arabinose consumed.

Arabinose Consumption in Yeast Containing Piromyces XI

Yeast expressing a Pyromyces sp. xylose isomerase were transformed with the arabinose utilization construct of the invention. Transformants were selected on YNB+arabinose plates. Two single colony isolates were tested on various media, with the untransformed parental strain used as a control. The media tested included: 20% washate (pH 6)

with 20 g/l arabinose; YPA (20 g/l arabinose); YPAX (20 g/l arabinose, 20 g/l xylose); and, YPAXD (20 g/l arabinose, 10 g/l xylose, 10 g/l glucose).

The yeast strains were pregrown on YPX, washed, and used to inoculate 150 ml sealed bottles with 25 ml medium, which were flushed with $N_2$ and incubated at 35° C. at 250 RPM. Cultures were sampled for HPLC at 0, 24, 48 and 72 hours. No growth was observed on YPA. 3.7 g $l^{-1}$ arabinose was consumed for clone 1 in YPAXD. Over half of this (2.1 g $l^{-1}$) was consumed between 24 and 48 h, when xylose and glucose already had been depleted. FIGS. 11-13 depict the results of these assays.

Summary of Fermentation Data

The fermentation data depicted herein demonstrate that the arabinose assembly of the invention enables conversion of arabinose into ethanol by S. cerevisiae. The ethanol yields from arabinose are around 0.5 g/g in all fermentations in which combinations of sugars were tested. The ethanol yield was slightly lower when arabinose was used as the sole carbon source, which likely indicates an increase in biomass generated from consumption of arabinose.

EQUIVALENTS

Those skilled in the art will recognize, or be able to ascertain using no more than routine experimentation, many equivalents to the specific embodiments of the invention described herein. Such equivalents are intended to be encompassed by the following claims. Additionally, all references cited herein are incorporated herein by reference as though they were reproduced herein in their entirety.

What is claimed is:

1. A recombinant eukaryotic host cell comprising a heterologous polynucleotide encoding an arabinose transporter (AraT), a heterologous polynucleotide encoding an arabinose isomerase (AI), a heterologous polynucleotide encoding a ribulokinase (RK) and a heterologous polynucleotide encoding a ribulose 5-phosphate epimerase (R5PE), wherein the AraT is an AraT of an organism selected from the group consisting of Kluveromyces lactis, Kluyveromyces thermotolerans, Zygosaccharomyces rouxii, Vanderwaltozyma polyspora, Debaryomyces hansenii, Aspergillus niger, Penicillium chrysogenum, Pichia guillermondii, Aspergillus flavus, Candida lusitnaea, Candida albicans (SC5314), Kluveromyces marxianus, and Candida arabinofermentans.

2. The recombinant eukaryotic host cell of claim 1, wherein the AraT comprises an amino acid sequence at least 80% identical to any one of the amino acid sequences of SEQ ID NOs: 9, 10, 11, 12, 13, 14, 15, 16, 17, 18, 19, 20, or 22.

3. The recombinant eukaryotic host cell of claim 1, wherein one or more of the AI, RK and R5PE is an AI, RK and R5PE of B. thetaiotamicron.

4. The recombinant eukaryotic host cell of claim 1, wherein
   a) the AI comprises an amino acid sequence at least 80% identical to the amino acid sequence of SEQ ID NO: 6;
   b) the RK comprises an amino acid sequence at least 80% identical to the amino acid sequence of SEQ ID NO: 7; and
   c) the R5PE comprises an amino acid sequence at least 80% identical to the amino acid sequence of SEQ ID NO: 8.

5. The recombinant eukaryotic host cell of claim 1, wherein expression of the heterologous polynucleotide confers an ability to ferment arabinose to the recombinant host cell.

6. The recombinant eukaryotic host cell of claim 1, further comprising a heterologous polynucleotide encoding a xylose isomerase (XI).

7. The recombinant eukaryotic host cell of claim 6, wherein the XI is an XI of *B. thetaiotamicron*.

8. The recombinant eukaryotic host cell of claim 6, wherein the XI comprises an amino acid sequence at least 80% identical to the amino acid sequence of SEQ ID NO: 23 or SEQ ID NO: 25.

9. The recombinant eukaryotic host cell of claim 1, wherein the host cell is a yeast cell.

10. The recombinant eukaryotic host cell of claim 9, wherein the yeast cell is selected from the group consisting of *Saccharomyces cerevisiae, Schizzosaccharomyces pombe, Candida albicans, Pichia pastoris, Pichia slipitis, Yarrowia lipolytica, Hansenula polymorpha, Phaffia rhodozyma, Candida utilis, Arxula adeninivorans, Debaryomyces hansenii, Debaryomyces polymorphus, Schizosaccharomyces pombe* and *Schwanniomyces occidenialis*.

11. The recombinant eukaryotic host cell of claim 9, wherein the yeast cell comprises a heterologous sequence encoding a xylulokinase, ribulose 5-phosphate isomerase, ribulose 5-phophate epimerase, transketolase and transaldolase, and wherein the yeast cell does not express an aldose reductase that is capable of catalyzing the conversion of xylose to xylitol.

12. The recombinant eukaryotic host cell of claim 1, wherein the host cell is capable of fermenting xylose, arabinose, or a combination thereof.

13. The recombinant eukaryotic host cell of claim 1, wherein the host cell is capable of fermenting arabinose from a cellulosic substrate.

14. The recombinant eukaryotic host cell of claim 12, wherein the fermentation product is selected from the group consisting of ethanol, lactic acid, hydrogen, butyric acid, acetone, and butanol.

15. The recombinant eukaryotic host cell of claim 1, wherein the host cell is an industrial strain exhibiting high ethanol tolerance.

16. The recombinant eukaryotic host cell of claim 15, wherein the host cell further exhibits high temperature tolerance.

17. The recombinant eukaryotic host cell of claim 1, wherein the host cell produces an ethanol yield of at least about 10 g/l ethanol after 24 hours of fermentation from a medium containing 20 g/l xylose and 21 g/l arabinose.

18. The recombinant eukaryotic host cell of claim 1, wherein the host cell produces an ethanol yield of at least about 13 g/l ethanol after 24 hours of fermentation from a medium containing 20 g/l glucose and 21 g/l arabinose.

19. The recombinant eukaryotic host cell of claim 1, wherein the host cell produces an ethanol yield of at least about 15 g/l ethanol after 24 hours of fermentation from a medium containing 10 g/l glucose, 10 g/l xylose and 21 g/l arabinose.

20. The recombinant eukaryotic host cell of claim 1, wherein the host cell further comprises one or more heterologous polynucleotides encoding a cellulase.

21. The recombinant eukaryotic host cell of claim 20, wherein the one or more cellulases is selected from the group consisting of endoglucanases, exoglucanases, and β-glucosidases.

22. The recombinant eukaryotic host cell of claim 21, wherein the host cell comprises: (a) a first heterologous polynucleotide that encodes an endoglucanase; (b) a second heterologous polynucleotide that encodes a β-glucosidase; (c) a third heterologous polynucleotide that encodes a first cellobiohydrolase; and, (d) a fourth heterologous polynucleotide that encodes a second cellobiohydrolase.

23. The recombinant eukaryotic host cell of claim 22, wherein (a) the first heterologous polynucleotide that encodes an endoglucanase is *A. fumigatus*; (b) the second heterologous polynucleotide that encodes a β-glucosidase is *S. fibuligera*; (c) the third heterologous polynucleotide that encodes a first cellobiohydrolase is *T. emersonii*; and, (d) the fourth heterologous polynucleotide that encodes a second cellobiohydrolase is *C. lucknowense*.

24. The recombinant host cell of claim 1, wherein at least one of the heterologous polynucleotides is integrated into the genome of the host cell.

25. A composition comprising a carbon source and the recombinant eukaryotic host cell of claim 1, wherein the carbon source is a cellulosic substrate that contains at least about 1% arabinose.

* * * * *